(12) United States Patent
Hagen et al.

(10) Patent No.: US 10,760,069 B2
(45) Date of Patent: Sep. 1, 2020

(54) PRODUCING ADIPIC ACID AND RELATED COMPOUNDS USING HYBRID POLYKETIDE SYNTHASES

(71) Applicant: The Regents of the University of California, Oakland, CA (US)

(72) Inventors: Andrew R. Hagen, Oakland, CA (US); Sean Poust, El Cerrito, CA (US); Leonard Katz, Oakland, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/867,575

(22) Filed: Jan. 10, 2018

(65) Prior Publication Data

US 2018/0273930 A1 Sep. 27, 2018

Related U.S. Application Data

(63) Continuation of application No. PCT/US2016/041795, filed on Jul. 11, 2016.

(60) Provisional application No. 62/191,283, filed on Jul. 10, 2015.

(51) Int. Cl.
| | |
|---|---|
| *C12N 9/00* | (2006.01) |
| *C12N 9/10* | (2006.01) |
| *C08G 63/16* | (2006.01) |
| *C08G 63/78* | (2006.01) |
| *C08G 69/28* | (2006.01) |
| *C12P 7/44* | (2006.01) |

(52) U.S. Cl.
CPC .............. *C12N 9/93* (2013.01); *C08G 63/16* (2013.01); *C08G 63/78* (2013.01); *C08G 69/28* (2013.01); *C12N 9/1029* (2013.01); *C12P 7/44* (2013.01); *C12Y 203/01094* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,174,358 A | 11/1979 | Epstein | |
| 2009/0286291 A1 | 11/2009 | Salas et al. | |
| 2011/0021790 A1* | 1/2011 | Katz | C12P 7/40 549/266 |
| 2013/0267696 A1 | 10/2013 | Fortman et al. | |
| 2013/0280766 A1* | 10/2013 | Fortman | C12N 15/52 435/106 |

OTHER PUBLICATIONS

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36):11643-50.*
Patent Cooperation Treaty, PCT/US2016/041795 "PCT Notification of Transmittal of the International Search Report and the Written Opinion of the International Searching Authority, or the Declaration," ISA, including Forms PCT/ISA/220, 210 and 237 (2016).
Hagen et al., "Engineering a Polyketide Synthase for In Vitro Production of Adipic Acid." ACS Synthetic Biology, vol. 5, No. 1, pp. 21-27, (2015). DOI:10.1021/acssynbio.5b00153.
Alini et al., "Development of new catalysts for N2O-decomposition from adipic acid plant." Appl. Catal. B Environ., vol. 70, pp. 323-329 (2007).
Aparicio et al., "Limited proteolysis and active-site studies of the first multienzyme component of the erythromycinproducing polyketide synthase." J. Biol. Chem., vol. 269, pp. 8524-8528 (1994).
Clomburg et al., "Integrated engineering of β-oxidation reversal and ω-oxidation pathways for the synthesis of medium chain ω-functionalized carboxylic acids." Metab. Eng., vol. 28, pp. 202-212 (2015).
Donadio et al., "Modular organization of genes required for complex polyketide biosynthesis." Science, vol. 252, pp. 675-679 (1991).
Dutta et al., "Structure of a modular polyketide synthase." Nature, vol. 510, pp. 512-517 (2014).
Gaisser et al., "Direct production of ivermectin-like drugs after domain exchange in the avermectin polyketide synthase of Streptomyces avermitilis ATCC31272." Org. Biomol. Chem., vol. 1, 2840 (2003).
George et al., "Correlation analysis of targeted proteins and metabolites to assess and engineer microbial isopentenol production: Targeted Proteomics-Based Correlation Analysis." Biotechnol. Bioeng., vol. 111, pp. 1648-1658 (2014).
Hagen et al., "In Vitro Analysis of Carboxyacyl Substrate Tolerance in the Loading and First Extension Modules of Borrelidin Polyketide Synthase." Biochemistry (Mosc.) vol. 53, pp. 5975-5977 (2014).
Hong et al., "Chain initiation on type I modular polyketide synthases revealed by limited proteolysis and ion-trap mass spectrometry." Limited proteolysis and MS of modular PKSs FEBS J., vol. 272, pp. 2373-2387 (2005).
Kellenberger et al., "A Polylinker Approach to Reductive Loop Swaps in Modular Polyketide Synthases." ChemBioChem., vol. 9, pp. 2740-2749 (2008).
Khosla, "Structures and Mechanisms of Polyketide Synthases." J. Org. Chem., vol. 74, pp. 6416-6420 (2009).
McDaniel, et al., "Multiple genetic modifications of the erythromycin polyketide synthase to produce a library of novel "unnatural" natural products" Proc. Natl. Acad. Sci., vol. 96, pp. 1846-1851 (1999).
Meluzzi et al., "Top-down mass spectrometry on low-resolution instruments: characterization of phosphopantetheinylated carrier domains in polyketide and non-ribosomal biosynthetic pathways." Bioorg. Med. Chem. Lett., vol. 18, pp. 3107-3111 (2008).

(Continued)

*Primary Examiner* — Iqbal H Chowdhury
(74) *Attorney, Agent, or Firm* — Lawrence Berkeley National Laboratory; Robin C. Chiang

(57) ABSTRACT

The present invention provides for a polyketide synthase (PKS) capable of synthesizing a carboxylic acid, said PKS comprising a synthetic or hybrid module. The present invention also provides for a host cell comprising the PKS and when cultured produces the carboxylic acid. In some embodiments, the carboxylic acid is adipic acid.

5 Claims, 12 Drawing Sheets
Specification includes a Sequence Listing.

(56) References Cited

OTHER PUBLICATIONS

Tang et al., "The 2.7-Å crystal structure of a 194-kDa homodimeric fragment of the 6-deoxyerythronolide B synthase." Proc. Natl. Acad. Sci., vol. 103, pp. 11124-11129 (2006).

Vergnolle et al., "Stereoselectivity of Isolated Dehydratase Domains of the Borrelidin Polyketide Synthase: Implications for cis Double Bond Formation." ChemBioChem., vol. 12, pp. 1011-1014 (2011).

Williams, "Engineering polyketide synthases and nonribosomal peptide synthetases" Curr. Opin. Struct. Biol., vol. 23, pp. 603-612 (2013).

Yoon et al., "Generation of Multiple Bioactive Macrolides by Hybrid Modular Polyketide Synthases in Streptomyces venezuelae." Chem. Biol., vol. 9, pp. 203-214 (2002).

Yu et al., "Direct biosynthesis of adipic acid from a synthetic pathway in recombinant *Escherichia coli*: Adipic Acid Production From a Synthetic Pathway." Biotechnol. Bioeng., vol. 111, pp. 2580-2586 (2014).

Zheng et al., "Structural Studies of an A2-Type Modular Polyketide Synthase Ketoreductase Reveal Features Controlling α-Substituent Stereochemistry." ACS Chem. Biol., vol. 8, pp. 1964-1971 (2013).

Donadio et al., "An erythromycin analog produced by reprogramming of polyketide synthesis." Proc. Natl. Acad. Sci. 90, 7119-7123 (1993).

Dahl et al., "Engineering dynamic pathway regulation using stress-response promoters." Nat. Biotechnol. 31, 1039-1046 (2013).

Edgar, R.C. (2004). "MUSCLE: multiple sequence alignment with high accuracy and high throughput." Nucleic Acids Res. 32, 1792-1797 (2004).

Hagen et al., "In Vitro Analysis of Carboxyacyl Substrate Tolerance in the Loading and First Extension Modules of Borrelidin Polyketide Synthase." Biochemistry (Mosc.) 53, 5975-5977 (2014).

Hillson et al., "j5 DNA Assembly Design Automation Software." ACS Synth. Biol. 1, 14-21 (2012).

Maclean et al., "Effect of Collision Energy Optimization on the Measurement of Peptides by Selected Reaction Monitoring (SRM) Mass Spectrometry." Anal. Chem. 82, 10116-10124 (2010).

Sievers et al., "Fast, scalable generation of high-quality protein multiple sequence alignments using Clustal Omega." Mol. Syst. Biol. 7, 539-539 (2014).

Vernolle et al., "Stereoselectivity of Isolated Dehydratase Domains of the Borrelidin Polyketide Synthase: Implications for cis Double Bond Formation." ChemBioChem 12, 1011-1014 (2011).

\* cited by examiner

N-terminal junctions:

C-terminal junction:

SEQUENCE LISTING

```
<160> NUMBER OF SEQ ID NOS: 10

<210> SEQ ID NO 1
<211> LENGTH: 2132
<212> TYPE: PRT
<213> ORGANISM: Streptomyces parvulus

<400> SEQUENCE: 1

Met Ala His Glu Asp Lys Leu Arg His Leu Leu Lys Arg Val Ser Ala
1               5                   10                  15

Glu Leu Asp Asp Thr Gln Arg Arg Val Arg Glu Met Glu Glu Ser Glu
            20                  25                  30
```

-continued

```
Arg Glu Pro Ile Ala Ile Val Gly Met Ser Cys Arg Leu Pro Gly Gly
         35                  40                  45

Val Asn Ser Pro Gly Glu Phe Trp Ser Leu Leu Glu Ala Gly Thr Asp
 50                  55                  60

Ala Val Ser Glu Phe Pro Arg Asp Arg Gly Trp Asp Val Glu Asn Leu
 65                  70                  75                  80

Tyr Asp Pro Asp Pro Asp Ala Pro Gly Arg Ser Tyr Val Arg Glu Gly
                 85                  90                  95

Gly Phe Leu Asp Gly Ala Gly Gln Phe Asp Ala Ala Phe Phe Gly Ile
             100                 105                 110

Ser Pro Arg Glu Ala Leu Ala Met Asp Pro Gln Gln Arg Leu Leu Leu
         115                 120                 125

Glu Cys Ser Trp Glu Ala Ile Glu Arg Ser Arg Ile Asp Pro Lys Thr
130                 135                 140

Leu His Gly Ser Arg Thr Gly Val Phe Ala Gly Ser Asn Trp Gln Asp
145                 150                 155                 160

Tyr Asn Thr Leu Leu Leu Asn Ala Glu Glu Arg Ser Gln Ser Tyr Leu
                165                 170                 175

Ala Thr Gly Ala Ser Gly Ser Val Leu Ser Gly Arg Val Ser Tyr Thr
            180                 185                 190

Leu Gly Met Glu Gly Pro Ala Ile Thr Val Asn Thr Ala Cys Ser Ser
        195                 200                 205

Ser Leu Val Ala Val His Leu Ala Arg Ser Leu Arg Ala Gly Glu
    210                 215                 220

Cys Asp Leu Ala Leu Ala Gly Ala Val Thr Val Met Ser Thr Pro Gln
225                 230                 235                 240

Leu Pro Val Ala Phe Ser Arg Gln Arg Gly Leu Ala Pro Asp Gly Arg
                245                 250                 255

Ser Lys Ala Phe Ala Val Ser Ala Asp Gly Met Gly Phe Gly Glu Gly
            260                 265                 270

Val Gly Val Leu Val Leu Glu Arg Leu Ser Val Ala Arg Arg Asn Gly
        275                 280                 285

His Arg Val Leu Ala Val Arg Gly Ser Ala Val Asn Gln Asp Gly
290                 295                 300

Ala Ser Asn Gly Leu Thr Ala Pro Asn Gly Pro Ser Gln Gln Arg Val
305                 310                 315                 320

Ile Arg Ala Ala Leu Ala Ser Ala Gly Leu Gly Pro Ala Asp Val Asp
                325                 330                 335

Val Val Glu Ala His Gly Thr Gly Thr Arg Leu Gly Asp Pro Ile Glu
            340                 345                 350

Ala Gln Ala Leu Leu Ala Thr Tyr Gly Arg Gly Arg Asp Ala Glu Arg
        355                 360                 365

Pro Leu Trp Leu Gly Ser Val Lys Ser Asn Ile Gly His Ala Gln Ala
    370                 375                 380

Ala Ala Gly Val Ala Gly Val Ile Lys Met Val Leu Ala Met Glu Lys
385                 390                 395                 400

Gly Arg Leu Pro Arg Thr Leu His Val Asp Glu Pro Ser Gly Glu Val
                405                 410                 415

Asp Trp Asp Ser Gly Ala Val Arg Leu Leu Thr Glu Ala Arg Asp Trp
            420                 425                 430

Pro Ser Glu Glu Gly Arg Leu Arg Arg Ala Gly Val Ser Ser Phe Gly
        435                 440                 445
```

```
Ile Ser Gly Thr Asn Ala His Val Ile Glu Glu Ala Pro Glu Glu
    450                 455                 460

Gly Glu Glu Pro Glu Ser Asp Ala Gly Val Val Pro Trp Val Leu
465                 470                 475                 480

Ser Ala Arg Thr Glu Gly Ala Leu Gln Ala Gln Ala Val Gln Leu Ser
                485                 490                 495

Glu Phe Val Gly Glu Ser Ser Pro Val Asp Val Gly Trp Ser Leu Val
                500                 505                 510

Ser Thr Arg Ala Ala Phe Glu His Arg Ala Val Val Gly Arg Gly
                515                 520                 525

Arg Asp Glu Leu Val Arg Gly Leu Ser Glu Val Ala Gln Gly Arg Gly
530                 535                 540

Val Arg Gly Val Ala Ser Ser Ala Ser Gly Gly Leu Ala Phe Val Phe
545                 550                 555                 560

Ala Gly Gln Gly Ser Gln Arg Leu Gly Met Gly Arg Gly Leu Tyr Glu
                565                 570                 575

Arg Phe Pro Val Phe Ala Glu Ala Phe Asp Glu Val Cys Gly Arg Val
                580                 585                 590

Gly Pro Gly Val Arg Glu Val Val Phe Gly Ser Asp Ala Gly Glu Leu
                595                 600                 605

Asp Arg Thr Val Trp Ala Gln Ala Gly Leu Phe Ala Leu Glu Val Ala
                610                 615                 620

Leu Phe Arg Leu Leu Glu Ser Trp Gly Val Arg Pro Gly Cys Leu Ile
625                 630                 635                 640

Gly His Ser Val Gly Glu Leu Ser Ala Ala Cys Val Ala Gly Leu Trp
                645                 650                 655

Ser Leu Glu Asp Ala Cys Arg Val Val Ala Ala Arg Ala Arg Leu Met
                660                 665                 670

Gln Ala Leu Pro Ala Gly Gly Val Met Val Ala Val Arg Ala Glu Ala
                675                 680                 685

Gly Glu Leu Ala Gly Phe Leu Gly Glu Asp Val Val Ile Ala Ser Val
                690                 695                 700

Asn Ala Pro Gly Gln Val Val Ile Ala Gly Pro Glu Gly Gly Val Glu
705                 710                 715                 720

Arg Val Val Ala Ala Cys Gly Ala Arg Ser Arg Arg Leu Ala Val Ser
                725                 730                 735

His Ala Phe His Ser Pro Leu Val Glu Pro Met Leu Gly Glu Phe Arg
                740                 745                 750

Arg Val Val Glu Ser Val Ala Phe Gly Val Pro Ser Leu Arg Val Val
                755                 760                 765

Ser Asn Val Thr Gly Ala Trp Val Asp Pro Glu Glu Trp Gly Thr Pro
                770                 775                 780

Glu Tyr Trp Val Arg Gln Val Arg Glu Pro Val Arg Phe Ala Asp Gly
785                 790                 795                 800

Val Ala Thr Leu Leu Asp Ala Gly Val Arg Thr Phe Val Glu Leu Gly
                805                 810                 815

Pro Ala Gly Ala Leu Thr Ser Met Val Ser His Cys Ala Asp Ala Thr
                820                 825                 830

Ala Thr Ser Val Thr Ala Val Pro Thr Leu Arg Pro Asp His Asp Glu
                835                 840                 845

Ser Arg Thr Val Leu Ser Ala Ala Ser Leu Tyr Val Gln Gly His
                850                 855                 860
```

-continued

```
Pro Val Asp Trp Ala Pro Leu Phe Pro Arg Ala Arg Thr Val Asp Leu
865                 870                 875                 880

Pro Thr Tyr Pro Phe Gln His Gln His Tyr Trp Met Met Asn Thr Gly
            885                 890                 895

Ser Ala Ala Glu Pro Ala Glu Leu Gly Leu Gly Asp Ala Arg His Pro
            900                 905                 910

Leu Leu Gly Ser Val Val Thr Val Ala Gly Asp Asp Lys Val Val Phe
            915                 920                 925

Ala Gly Arg Leu Ala Leu Arg Thr His Pro Trp Leu Ala Asp His Thr
            930                 935                 940

Val Leu Asp Ala Val Leu Leu Pro Ala Thr Ala Phe Leu Glu Leu Ala
945                 950                 955                 960

Val Arg Ala Gly Glu Glu Val Ser Cys Pro Val Val His Asp Leu Thr
                965                 970                 975

Leu His Arg Pro Leu Val Val Pro Glu Arg Gly Ala Val Gln Val Gln
                980                 985                 990

Met Ala Val Gly Ala Pro Glu Ala Asp Gly Arg Arg Glu Val Arg Val
                995                 1000                1005

Tyr Ser Arg Pro Asp Asp Asp Ala Glu His Glu Trp Thr Leu His
    1010                1015                1020

Ala Ala Gly Leu Leu Ala Ser Ala Ala Thr Ala Glu Pro Ala Val
    1025                1030                1035

Ala Ala Gly Ala Trp Pro Pro Glu Ala Gln Ala Val Asp Leu
    1040                1045                1050

Asp Gly Phe Tyr Ala Gly Leu Ala Glu His Gly Tyr His Tyr Gly
    1055                1060                1065

Pro Leu Phe Gln Gly Val Arg Ala Ala Trp Arg Leu Gly Asp Asp
    1070                1075                1080

Val Leu Ala Glu Ile Val Leu Pro Glu Ala Ala Gly Ala Asp Ala
    1085                1090                1095

Ala Arg Tyr Gly Met His Pro Ala Leu Leu Asp Ala Val Leu His
    1100                1105                1110

Ala Ala Arg Leu Gly Ala Phe Arg Glu Arg Ser Glu Glu Lys Tyr
    1115                1120                1125

Leu Pro Phe Ala Trp Glu Gly Val Thr Leu Arg Thr Arg Gly Ala
    1130                1135                1140

Thr Ala Val Arg Ala Arg Ile Ser Arg Ala Gly Thr Asp Ala Ile
    1145                1150                1155

Arg Leu Asp Val Thr Asp Thr Ala Asp Arg Pro Val Leu Thr Ala
    1160                1165                1170

Glu Ser Leu Val Leu Arg Ser Ala Ala Ala Arg Thr Gly Ala
    1175                1180                1185

Arg Arg Gln Ala His Gln Ala Arg Leu Tyr Arg Leu Ser Trp Pro
    1190                1195                1200

Thr Val Gln Leu Pro Thr Ser Ala Gln Pro Ser Cys Val Leu
    1205                1210                1215

Leu Gly Thr Ser Glu Val Ser Ala Asp Ile Gln Val Tyr Pro Asp
    1220                1225                1230

Leu Arg Ser Leu Thr Ala Ala Leu Asp Ala Gly Ala Glu Pro Pro
    1235                1240                1245

Gly Val Val Ile Ala Pro Thr Pro Pro Gly Gly Gly Arg Thr Ala
    1250                1255                1260
```

Asp Val Arg Glu Thr Thr Arg His Ala Leu Asp Leu Val Gln Gly
1265                    1270                1275

Trp Leu Ser Asp Gln Arg Leu Asn Glu Ser Arg Leu Leu Leu Val
1280                    1285                1290

Thr Gln Gly Ala Val Ala Val Glu Pro Gly Pro Val Thr Asp
1295                    1300                1305

Leu Ala Gln Ala Ala Leu Trp Gly Leu Leu Arg Ser Thr Gln Thr
1310                    1315                1320

Glu His Pro Asp Arg Phe Val Leu Val Asp Val Pro Glu Pro Ala
1325                    1330                1335

Gln Leu Leu Pro Ala Leu Pro Gly Val Leu Ala Cys Gly Glu Pro
1340                    1345                1350

Gln Leu Ala Leu Arg Arg Gly Gly Ala His Ala Pro Arg Leu Ala
1355                    1360                1365

Gly Leu Gly Ser Asp Asp Val Leu Pro Val Pro Asp Gly Thr Gly
1370                    1375                1380

Trp Arg Leu Glu Ala Thr Arg Pro Gly Ser Leu Asp Gly Leu Ala
1385                    1390                1395

Leu Val Asp Glu Pro Thr Ala Thr Ala Pro Leu Gly Asp Gly Glu
1400                    1405                1410

Val Arg Ile Ala Met Arg Ala Ala Gly Val Asn Phe Arg Asp Ala
1415                    1420                1425

Leu Ile Ala Leu Gly Met Tyr Pro Gly Val Ala Ser Leu Gly Ser
1430                    1435                1440

Glu Gly Ala Gly Val Val Val Glu Thr Gly Pro Gly Val Thr Gly
1445                    1450                1455

Leu Ala Pro Gly Asp Arg Val Met Gly Met Ile Pro Lys Ala Phe
1460                    1465                1470

Gly Pro Leu Ala Val Ala Asp His Arg Met Val Thr Arg Ile Pro
1475                    1480                1485

Ala Gly Trp Ser Phe Ala Arg Ala Ala Ser Val Pro Ile Val Phe
1490                    1495                1500

Leu Thr Ala Tyr Tyr Ala Leu Val Asp Leu Ala Gly Leu Arg Pro
1505                    1510                1515

Gly Glu Ser Leu Leu Val His Ser Ala Ala Gly Gly Val Gly Met
1520                    1525                1530

Ala Ala Ile Gln Leu Ala Arg His Leu Gly Ala Glu Val Tyr Ala
1535                    1540                1545

Thr Ala Ser Glu Asp Lys Trp Gln Ala Val Glu Leu Ser Arg Glu
1550                    1555                1560

His Leu Ala Ser Ser Arg Thr Cys Asp Phe Glu Gln Gln Phe Leu
1565                    1570                1575

Gly Ala Thr Gly Gly Arg Gly Val Asp Val Val Leu Asn Ser Leu
1580                    1585                1590

Ala Gly Glu Phe Ala Asp Ala Ser Leu Arg Met Leu Pro Arg Gly
1595                    1600                1605

Gly Arg Phe Leu Glu Leu Gly Lys Thr Asp Val Arg Asp Pro Val
1610                    1615                1620

Glu Val Ala Asp Ala His Pro Gly Val Ser Tyr Gln Ala Phe Asp
1625                    1630                1635

Thr Val Glu Ala Gly Pro Gln Arg Ile Gly Glu Met Leu His Glu
1640                    1645                1650

-continued

Leu Val Glu Leu Phe Glu Gly Arg Val Leu Glu Pro Leu Pro Val
1655                    1660                1665

Thr Ala Trp Asp Val Arg Gln Ala Pro Glu Ala Leu Arg His Leu
1670                    1675                1680

Ser Gln Ala Arg His Val Gly Lys Leu Val Leu Thr Met Pro Pro
1685                    1690                1695

Val Trp Asp Ala Ala Gly Thr Val Leu Val Thr Gly Gly Thr Gly
1700                    1705                1710

Ala Leu Gly Ala Glu Val Ala Arg His Leu Val Ile Glu Arg Gly
1715                    1720                1725

Val Arg Asn Leu Val Leu Val Ser Arg Arg Gly Pro Ala Ala Ser
1730                    1735                1740

Gly Ala Ala Glu Leu Val Ala Gln Leu Thr Ala Tyr Gly Ala Glu
1745                    1750                1755

Val Ser Leu Gln Ala Cys Asp Val Ala Asp Arg Glu Thr Leu Ala
1760                    1765                1770

Lys Val Leu Ala Ser Ile Pro Asp Glu His Pro Leu Thr Ala Val
1775                    1780                1785

Val His Ala Ala Gly Val Leu Asp Asp Gly Val Ser Glu Ser Leu
1790                    1795                1800

Thr Val Glu Arg Leu Asp Gln Val Leu Arg Pro Lys Val Asp Gly
1805                    1810                1815

Ala Arg Asn Leu Leu Glu Leu Ile Asp Pro Asp Val Ala Leu Val
1820                    1825                1830

Leu Phe Ser Ser Val Ser Gly Val Leu Gly Ser Gly Gly Gln Gly
1835                    1840                1845

Asn Tyr Ala Ala Ala Asn Ser Phe Leu Asp Ala Leu Ala Gln Gln
1850                    1855                1860

Arg Gln Ser Arg Gly Leu Pro Thr Arg Ser Leu Ala Trp Gly Pro
1865                    1870                1875

Trp Ala Glu His Gly Met Ala Ser Thr Leu Arg Glu Ala Glu Gln
1880                    1885                1890

Asp Arg Leu Ala Arg Ser Gly Leu Leu Pro Ile Ser Thr Glu Glu
1895                    1900                1905

Gly Leu Ser Gln Phe Asp Ala Ala Cys Gly Gly Ala His Thr Val
1910                    1915                1920

Val Ala Pro Val Arg Phe Ser Arg Leu Ser Asp Gly Asn Ala Ile
1925                    1930                1935

Lys Phe Ser Val Leu Gln Gly Leu Val Gly Pro His Arg Val Asn
1940                    1945                1950

Lys Ala Ala Thr Ala Asp Asp Ala Glu Ser Leu Arg Lys Arg Leu
1955                    1960                1965

Ala Ala Leu Pro Glu Ala Asp Arg Arg Arg Ala Val Leu Asp Leu
1970                    1975                1980

Val Glu Glu Leu Val Leu Gly Val Leu Gly His Glu Thr Arg Ala
1985                    1990                1995

Ala Ile Gly Pro Asp Ser Ser Phe His Ala Ile Gly Phe Asp Ser
2000                    2005                2010

Leu Thr Ala Val Glu Leu Arg Asn Leu Leu Thr Val Arg Leu Gly
2015                    2020                2025

Met Lys Leu Pro Ala Thr Leu Val Tyr Asp His Pro Thr Leu Ser
2030                    2035                2040

```
Ser Leu Ala Asp His Leu His Glu Gln Leu Val Ile Asp Gly Thr
    2045            2050                2055

Pro Met Thr Asp Thr Ala Ala Asp Leu Leu Ala Glu Leu Asp Ala
    2060            2065                2070

Leu Ala Ala Arg Leu Ala Ala Val Gly Leu Glu Pro Glu Ala Arg
    2075            2080                2085

Ala Arg Ile Gly Arg Arg Leu Lys Asp Met Gln Thr Ala Cys Glu
    2090            2095                2100

Pro Arg Ser Glu Ser Ser Arg Asp Leu Lys Ser Ala Ser Arg Thr
    2105            2110                2115

Glu Val Leu Asp Phe Leu Thr Asn Glu Leu Gly Ile Ser Arg
    2120            2125                2130

<210> SEQ ID NO 2
<211> LENGTH: 2331
<212> TYPE: PRT
<213> ORGANISM: Streptomyces parvulus

<400> SEQUENCE: 2

Met Ala His Glu Asp Lys Leu Arg His Leu Leu Lys Arg Val Ser Ala
1               5                   10                  15

Glu Leu Asp Asp Thr Gln Arg Arg Val Arg Glu Met Glu Glu Ser Glu
                20                  25                  30

Arg Glu Pro Ile Ala Ile Val Gly Met Ser Cys Arg Leu Pro Gly Gly
            35                  40                  45

Val Asn Ser Pro Gly Glu Phe Trp Ser Leu Leu Glu Ala Gly Thr Asp
        50                  55                  60

Ala Val Ser Glu Phe Pro Arg Asp Arg Gly Trp Asp Val Glu Asn Leu
65                  70                  75                  80

Tyr Asp Pro Asp Pro Asp Ala Pro Gly Arg Ser Tyr Val Arg Glu Gly
                85                  90                  95

Gly Phe Leu Asp Gly Ala Gly Gln Phe Asp Ala Ala Phe Phe Gly Ile
            100                 105                 110

Ser Pro Arg Glu Ala Leu Ala Met Asp Pro Gln Gln Arg Leu Leu Leu
        115                 120                 125

Glu Cys Ser Trp Glu Ala Ile Glu Arg Ser Arg Ile Asp Pro Lys Thr
    130                 135                 140

Leu His Gly Ser Arg Thr Gly Val Phe Ala Gly Ser Asn Trp Gln Asp
145                 150                 155                 160

Tyr Asn Thr Leu Leu Leu Asn Ala Glu Glu Arg Ser Gln Ser Tyr Leu
                165                 170                 175

Ala Thr Gly Ala Ser Gly Ser Val Leu Ser Gly Arg Val Ser Tyr Thr
            180                 185                 190

Leu Gly Met Glu Gly Pro Ala Ile Thr Val Asn Thr Ala Cys Ser Ser
        195                 200                 205

Ser Leu Val Ala Val His Leu Ala Ala Arg Ser Leu Arg Ala Gly Glu
    210                 215                 220

Cys Asp Leu Ala Leu Ala Gly Ala Val Thr Val Met Ser Thr Pro Gln
225                 230                 235                 240

Leu Pro Val Ala Phe Ser Arg Gln Arg Gly Leu Ala Pro Asp Gly Arg
                245                 250                 255

Ser Lys Ala Phe Ala Val Ser Ala Asp Gly Met Gly Phe Gly Glu Gly
            260                 265                 270

Val Gly Val Leu Val Leu Glu Arg Leu Ser Val Ala Arg Arg Asn Gly
        275                 280                 285
```

-continued

His Arg Val Leu Ala Val Val Arg Gly Ser Ala Val Asn Gln Asp Gly
290                 295                 300

Ala Ser Asn Gly Leu Thr Ala Pro Asn Gly Pro Ser Gln Gln Arg Val
305                 310                 315                 320

Ile Arg Ala Ala Leu Ala Ser Ala Gly Leu Gly Pro Ala Asp Val Asp
            325                 330                 335

Val Val Glu Ala His Gly Thr Gly Thr Arg Leu Gly Asp Pro Ile Glu
            340                 345                 350

Ala Gln Ala Leu Leu Ala Thr Tyr Gly Arg Gly Arg Asp Ala Glu Arg
            355                 360                 365

Pro Leu Trp Leu Gly Ser Val Lys Ser Asn Ile Gly His Ala Gln Ala
370                 375                 380

Ala Ala Gly Val Ala Gly Val Ile Lys Met Val Leu Ala Met Glu Lys
385                 390                 395                 400

Gly Arg Leu Pro Arg Thr Leu His Val Asp Glu Pro Ser Gly Glu Val
            405                 410                 415

Asp Trp Asp Ser Gly Ala Val Arg Leu Leu Thr Glu Ala Arg Asp Trp
            420                 425                 430

Pro Ser Glu Glu Gly Arg Leu Arg Arg Ala Gly Val Ser Ser Phe Gly
            435                 440                 445

Ile Ser Gly Thr Asn Ala His Val Ile Ile Glu Glu Ala Pro Glu Glu
450                 455                 460

Gly Glu Glu Pro Glu Ser Asp Ala Gly Gly Val Val Pro Trp Val Leu
465                 470                 475                 480

Ser Ala Arg Thr Glu Gly Ala Leu Gln Ala Gln Ala Val Gln Leu Ser
            485                 490                 495

Glu Phe Val Gly Glu Ser Ser Pro Val Asp Val Gly Trp Ser Leu Val
            500                 505                 510

Ser Thr Arg Ala Ala Phe Glu His Arg Ala Val Val Gly Arg Gly
            515                 520                 525

Arg Asp Glu Leu Val Arg Gly Leu Ser Glu Val Ala Gln Gly Arg Gly
530                 535                 540

Val Arg Gly Val Ala Ser Ser Ala Ser Gly Gly Leu Ala Phe Val Phe
545                 550                 555                 560

Ala Gly Gln Gly Ser Gln Arg Leu Gly Met Gly Arg Gly Leu Tyr Glu
            565                 570                 575

Arg Phe Pro Val Phe Ala Glu Ala Phe Asp Glu Val Cys Gly Arg Val
            580                 585                 590

Gly Pro Gly Val Arg Glu Val Val Phe Gly Ser Asp Ala Gly Glu Leu
            595                 600                 605

Asp Arg Thr Val Trp Ala Gln Ala Gly Leu Phe Ala Leu Glu Val Ala
610                 615                 620

Leu Phe Arg Leu Leu Glu Ser Trp Gly Val Arg Pro Gly Cys Leu Ile
625                 630                 635                 640

Gly His Ser Val Gly Glu Leu Ser Ala Ala Cys Val Ala Gly Leu Trp
            645                 650                 655

Ser Leu Glu Asp Ala Cys Arg Val Ala Ala Arg Ala Arg Leu Met
            660                 665                 670

Gln Ala Leu Pro Ala Gly Gly Val Met Val Ala Val Arg Ala Glu Ala
            675                 680                 685

Gly Glu Leu Ala Gly Phe Leu Gly Glu Asp Val Val Ile Ala Ser Val
690                 695                 700

```
Asn Ala Pro Gly Gln Val Val Ile Ala Gly Pro Glu Gly Gly Val Glu
705                 710                 715                 720

Arg Val Val Ala Ala Cys Gly Ala Arg Ser Arg Leu Ala Val Ser
                725                 730                 735

His Ala Phe His Ser Pro Leu Val Glu Pro Met Leu Gly Glu Phe Arg
            740                 745                 750

Arg Val Val Glu Ser Val Ala Phe Gly Val Pro Ser Leu Arg Val Val
            755                 760                 765

Ser Asn Val Thr Gly Ala Trp Val Asp Pro Glu Glu Trp Gly Thr Pro
770                 775                 780

Glu Tyr Trp Val Arg Gln Val Arg Glu Pro Val Arg Phe Ala Asp Gly
785                 790                 795                 800

Val Ala Thr Leu Leu Asp Ala Gly Val Arg Thr Phe Val Glu Leu Gly
                805                 810                 815

Pro Ala Gly Ala Leu Thr Ser Met Val Ser His Cys Ala Asp Ala Thr
                820                 825                 830

Ala Thr Ser Val Thr Ala Val Pro Thr Leu Arg Pro Asp His Asp Glu
            835                 840                 845

Ser Arg Thr Val Leu Ser Ala Ala Ser Leu Tyr Val Gln Gly His
850                 855                 860

Pro Val Asp Trp Ala Pro Leu Phe Pro Arg Ala Arg Thr Val Asp Leu
865                 870                 875                 880

Pro Thr Tyr Pro Phe Gln His Gln His Tyr Trp Met Met Asn Thr Gly
                885                 890                 895

Ser Ala Ala Glu Pro Ala Glu Leu Gly Leu Gly Asp Ala Arg His Pro
                900                 905                 910

Leu Leu Gly Ser Val Val Thr Val Ala Gly Asp Asp Lys Val Val Phe
            915                 920                 925

Ala Gly Arg Leu Ala Leu Arg Thr His Pro Trp Leu Ala Asp His Thr
            930                 935                 940

Val Leu Asp Ala Val Leu Leu Pro Ala Thr Ala Phe Leu Glu Leu Ala
945                 950                 955                 960

Val Arg Ala Gly Glu Glu Val Ser Cys Pro Val Val His Asp Leu Thr
                965                 970                 975

Leu His Arg Pro Leu Val Val Pro Glu Arg Gly Ala Val Gln Val Gln
            980                 985                 990

Met Ala Val Gly Ala Pro Glu Ala Asp Gly Arg Arg Glu Val Arg Val
                995                 1000                1005

Tyr Ser Arg Pro Asp Asp Ala Glu His Glu Trp Thr Leu His
1010                1015                1020

Ala Ala Gly Leu Leu Ala Ser Ala Ala Thr Ala Glu Pro Ala Val
1025                1030                1035

Ala Ala Gly Ala Trp Pro Pro Glu Ala Gln Ala Val Asp Leu
1040                1045                1050

Asp Gly Phe Tyr Ala Gly Leu Ala Glu His Gly Tyr His Tyr Gly
1055                1060                1065

Pro Leu Phe Gln Gly Val Arg Ala Ala Trp Arg Leu Gly Asp Asp
1070                1075                1080

Val Leu Ala Glu Ile Val Leu Pro Glu Ala Ala Gly Ala Asp Ala
1085                1090                1095

Ala Arg Tyr Gly Met His Pro Ala Leu Leu Asp Ala Val Leu His
1100                1105                1110

Ala Ala Arg Leu Gly Ala Phe Arg Glu Arg Ser Glu Glu Lys Tyr
1115                1120                1125
```

-continued

Leu Pro Phe Ala Trp Glu Gly Val Thr Leu Arg Thr Arg Gly Ala
1130            1135                1140

Thr Ala Val Arg Ala Arg Ile Ser Arg Ala Gly Thr Asp Ala Ile
1145            1150                1155

Arg Leu Asp Val Thr Asp Thr Ala Asp Arg Pro Val Leu Thr Ala
1160            1165                1170

Glu Ser Leu Val Leu Arg Ser Ala Ala Arg Arg Thr Gly Ala
1175            1180                1185

Arg Arg Gln Ala His Gln Ala Arg Leu Tyr Arg Leu Ser Trp Pro
1190            1195                1200

Thr Val Gln Leu Pro Thr Ser Ala Gln Pro Pro Ser Cys Val Leu
1205            1210                1215

Leu Gly Thr Ser Glu Val Ser Ala Asp Ile Gln Val Tyr Pro Asp
1220            1225                1230

Leu Arg Ser Leu Thr Ala Ala Leu Asp Ala Gly Ala Glu Pro Pro
1235            1240                1245

Gly Val Val Ile Ala Pro Thr Pro Pro Gly Gly Gly Arg Thr Ala
1250            1255                1260

Asp Val Arg Glu Thr Thr Arg His Ala Leu Asp Leu Val Gln Gly
1265            1270                1275

Trp Leu Ser Asp Gln Arg Leu Asn Glu Ser Arg Leu Leu Leu Val
1280            1285                1290

Thr Gln Gly Ala Val Ala Val Glu Pro Gly Glu Pro Val Thr Asp
1295            1300                1305

Leu Ala Gln Ala Ala Leu Trp Gly Leu Leu Arg Ser Thr Gln Thr
1310            1315                1320

Glu His Pro Asp Arg Phe Val Leu Val Asp Val Pro Glu Pro Ala
1325            1330                1335

Gln Leu Leu Pro Ala Leu Pro Gly Val Leu Ala Cys Gly Glu Pro
1340            1345                1350

Gln Leu Ala Leu Arg Arg Gly Gly Ala His Ala Pro Arg Leu Ala
1355            1360                1365

Gly Leu Gly Ser Asp Asp Val Leu Pro Val Pro Asp Gly Thr Gly
1370            1375                1380

Trp Arg Leu Glu Ala Thr Arg Pro Gly Ser Leu Asp Gly Leu Ala
1385            1390                1395

Leu Val Asp Glu Pro Thr Ala Thr Ala Pro Leu Gly Asp Gly Glu
1400            1405                1410

Val Arg Ile Ala Met Arg Ala Ala Gly Val Asn Phe Arg Asp Ala
1415            1420                1425

Leu Ile Ala Leu Gly Met Tyr Pro Gly Val Ala Ser Leu Gly Ser
1430            1435                1440

Glu Gly Ala Gly Val Val Val Glu Thr Gly Pro Gly Val Thr Gly
1445            1450                1455

Leu Ala Pro Gly Asp Arg Val Met Gly Met Ile Pro Lys Ala Phe
1460            1465                1470

Gly Pro Leu Ala Val Ala Asp His Arg Met Val Thr Arg Ile Pro
1475            1480                1485

Ala Gly Trp Ser Phe Ala Arg Ala Ala Ser Val Pro Ile Val Phe
1490            1495                1500

Leu Thr Ala Tyr Tyr Ala Leu Val Asp Leu Ala Gly Leu Arg Pro
1505            1510                1515

```
Gly Glu Ser Leu Leu Val His Ser Ala Gly Gly Val Gly Met
1520                1525                1530

Ala Ala Ile Gln Leu Ala Arg His Leu Gly Ala Glu Val Tyr Ala
1535                1540                1545

Thr Ala Ser Glu Asp Lys Trp Gln Ala Val Glu Leu Ser Arg Glu
1550                1555                1560

His Leu Ala Ser Ser Arg Thr Cys Asp Phe Glu Gln Gln Phe Leu
1565                1570                1575

Gly Ala Thr Gly Gly Arg Gly Val Asp Val Val Leu Asn Ser Leu
1580                1585                1590

Ala Gly Glu Phe Ala Asp Ala Ser Leu Arg Met Leu Pro Arg Gly
1595                1600                1605

Gly Arg Phe Leu Glu Leu Gly Lys Thr Asp Val Arg Asp Pro Val
1610                1615                1620

Glu Val Ala Asp Ala His Pro Gly Val Ser Tyr Gln Ala Phe Asp
1625                1630                1635

Thr Val Glu Ala Gly Pro Gln Arg Ile Gly Glu Met Leu His Glu
1640                1645                1650

Leu Val Glu Leu Phe Glu Gly Arg Val Leu Glu Pro Leu Pro Val
1655                1660                1665

Thr Ala Trp Asp Val Arg Gln Ala Pro Glu Ala Leu Arg His Leu
1670                1675                1680

Ser Gln Ala Arg His Val Gly Lys Leu Val Leu Thr Met Pro Pro
1685                1690                1695

Val Trp Asp Ala Ala Gly Thr Val Leu Val Thr Gly Gly Thr Gly
1700                1705                1710

Ala Leu Gly Ala Glu Val Ala Arg His Leu Val Ile Glu Arg Gly
1715                1720                1725

Val Arg Asn Leu Val Leu Val Ser Arg Arg Gly Pro Ala Ala Ser
1730                1735                1740

Gly Ala Ala Glu Leu Val Ala Gln Leu Thr Ala Tyr Gly Ala Glu
1745                1750                1755

Val Ser Leu Gln Ala Cys Asp Val Ala Asp Arg Glu Thr Leu Ala
1760                1765                1770

Lys Val Leu Ala Ser Ile Pro Asp Glu His Pro Leu Thr Ala Val
1775                1780                1785

Val His Ala Ala Gly Val Leu Asp Asp Gly Val Ser Glu Ser Leu
1790                1795                1800

Thr Val Glu Arg Leu Asp Gln Val Leu Arg Pro Lys Val Asp Gly
1805                1810                1815

Ala Arg Asn Leu Leu Glu Leu Ile Asp Pro Asp Val Ala Leu Val
1820                1825                1830

Leu Phe Ser Ser Val Ser Gly Val Leu Gly Ser Gly Gly Gln Gly
1835                1840                1845

Asn Tyr Ala Ala Ala Asn Ser Phe Leu Asp Ala Leu Ala Gln Gln
1850                1855                1860

Arg Gln Ser Arg Gly Leu Pro Thr Arg Ser Leu Ala Trp Gly Pro
1865                1870                1875

Trp Ala Glu His Gly Met Ala Ser Thr Leu Arg Glu Ala Glu Gln
1880                1885                1890

Asp Arg Leu Ala Arg Ser Gly Leu Leu Pro Ile Ser Thr Glu Glu
1895                1900                1905
```

-continued

```
Gly Leu Ser Gln Phe Asp Ala Ala Cys Gly Gly Ala His Thr Val
    1910                1915                1920

Val Ala Pro Val Arg Phe Ser Arg Leu Ser Asp Gly Asn Ala Ile
    1925                1930                1935

Lys Phe Ser Val Leu Gln Gly Leu Val Gly Pro His Arg Val Asn
    1940                1945                1950

Lys Ala Ala Thr Ala Asp Asp Ala Glu Ser Leu Arg Lys Arg Leu
    1955                1960                1965

Ala Ala Leu Pro Glu Ala Asp Arg Arg Arg Ala Val Leu Asp Leu
    1970                1975                1980

Val Glu Glu Leu Val Leu Gly Val Leu Gly His Glu Thr Arg Ala
    1985                1990                1995

Ala Ile Gly Pro Asp Ser Ser Phe His Ala Ile Gly Phe Asp Ser
    2000                2005                2010

Leu Thr Ala Val Glu Leu Arg Asn Leu Leu Thr Val Arg Leu Gly
    2015                2020                2025

Met Lys Leu Pro Ala Thr Leu Val Tyr Asp His Pro Thr Leu Ser
    2030                2035                2040

Ser Leu Ala Asp His Leu His Glu Gln Leu Glu Ser Gly Thr Pro
    2045                2050                2055

Ala Arg Glu Ala Ser Ser Ala Leu Arg Asp Gly Tyr Arg Gln Ala
    2060                2065                2070

Gly Val Ser Gly Arg Val Arg Ser Tyr Leu Asp Leu Leu Ala Gly
    2075                2080                2085

Leu Ser Asp Phe Arg Glu His Phe Asp Gly Ser Asp Gly Phe Ser
    2090                2095                2100

Leu Asp Leu Val Asp Met Ala Asp Gly Pro Gly Glu Val Thr Val
    2105                2110                2115

Ile Cys Cys Ala Gly Thr Ala Ala Ile Ser Gly Pro His Glu Phe
    2120                2125                2130

Thr Arg Leu Ala Gly Ala Leu Arg Gly Ile Ala Pro Val Arg Ala
    2135                2140                2145

Val Pro Gln Pro Gly Tyr Glu Glu Gly Glu Pro Leu Pro Ser Ser
    2150                2155                2160

Met Ala Ala Val Ala Ala Val Gln Ala Asp Ala Val Ile Arg Thr
    2165                2170                2175

Gln Gly Asp Lys Pro Phe Val Val Ala Gly His Ser Ala Gly Ala
    2180                2185                2190

Leu Met Ala Tyr Ala Leu Ala Thr Glu Leu Leu Asp Arg Gly His
    2195                2200                2205

Pro Pro Arg Gly Val Val Leu Ile Asp Val Tyr Pro Pro Gly His
    2210                2215                2220

Gln Asp Ala Met Asn Ala Trp Leu Glu Glu Leu Thr Ala Thr Leu
    2225                2230                2235

Phe Asp Arg Glu Thr Val Arg Met Asp Asp Thr Arg Leu Thr Ala
    2240                2245                2250

Leu Gly Ala Tyr Asp Arg Leu Thr Gly Gln Trp Arg Pro Arg Glu
    2255                2260                2265

Thr Gly Leu Pro Thr Leu Leu Val Ser Ala Gly Glu Pro Met Gly
    2270                2275                2280

Pro Trp Pro Asp Asp Ser Trp Lys Pro Thr Trp Pro Phe Glu His
    2285                2290                2295
```

```
Asp Thr Val Ala Val Pro Gly Asp His Phe Thr Met Val Gln Glu
    2300                2305                2310

His Ala Asp Ala Ile Ala Arg His Ile Asp Ala Trp Leu Gly Gly
    2315                2320                2325

Gly Asn Ser
    2330

<210> SEQ ID NO 3
<211> LENGTH: 13
<212> TYPE: PRT
<213> ORGANISM: Streptomyces parvulus

<400> SEQUENCE: 3

Val Val Glu Ser Val Ala Phe Gly Val Pro Ser Leu Arg
1               5                   10

<210> SEQ ID NO 4
<211> LENGTH: 23
<212> TYPE: PRT
<213> ORGANISM: Streptomyces parvulus

<400> SEQUENCE: 4

Ala Ala Ile Gly Pro Asp Ser Ser Phe His Ala Ile Gly Phe Asp Ser
1               5                   10                  15

Leu Thr Ala Val Glu Leu Arg
            20

<210> SEQ ID NO 5
<211> LENGTH: 876
<212> TYPE: PRT
<213> ORGANISM: Streptomyces parvulus

<400> SEQUENCE: 5

Met Thr Gly Ser Ala Val Ser Ala Pro Phe Leu Gln Pro Pro Glu Pro
1               5                   10                  15

Val Ser Gly His Ser Glu Arg Lys Ser Asp Pro Val Leu Leu Val Gly
            20                  25                  30

Ala Gly Arg Arg Ala Arg Met Ala Asp Ala Val Arg Ala Ala Gly Ala
        35                  40                  45

Gln Ala Gly Ile Asp Pro Ala Val Leu Arg Arg Thr Arg Ala Thr Leu
    50                  55                  60

Ile Thr Ala Gly Ser Ala Gly Ala Gly Arg Leu Ala Ala Ala Leu
65              70                  75                  80

Arg Leu Thr Gly Ala Thr Ile Ser Leu Asp Thr Arg Glu Thr Pro Thr
                85                  90                  95

Leu Leu Ala Leu His Leu Ala Ala Gln Ala Leu Arg Ala Gly Asp Thr
            100                 105                 110

Ser Tyr Ala Val Val Gly Ala Glu Leu Pro Asp Gly Asn Cys Ala Leu
        115                 120                 125

Ile Leu Ala Arg Gln Ser Ala Ala Thr Ala Glu Gly Ala Val Pro Gln
    130                 135                 140

Ala Ile Val Arg Thr Thr Thr Ala Asp Arg Thr Thr Ala Asp His
145                 150                 155                 160

Ala Pro Ala Pro Asp Asp His Gly Ser Pro Ala Arg Glu Ala Pro His
                165                 170                 175

Ala Thr Arg Thr Leu Ser Pro Gly Ile Thr Gln Ala Pro Ala Glu Gly
            180                 185                 190
```

```
Phe Pro Gly Leu Leu Ala Thr Leu His Asp Asp Thr Pro Leu Arg Pro
            195                 200                 205

Thr Ala Val Thr Glu His Gly Ser Asp Ala Thr Thr Val Leu Val Leu
    210                 215                 220

Leu Asp Gln Pro Gln Asp Ala Ala Pro Ala Ala Pro Leu Pro Trp Val
225                 230                 235                 240

Val Ser Ala Pro His Thr Arg Ala Leu Arg Ala Thr Ala Ala Thr Leu
                245                 250                 255

Ala Val His Leu Asp Thr Thr Pro Ala Pro Ala Asp Val Ala His
            260                 265                 270

Thr Leu Leu Thr Ala Arg Pro Asp Arg His Arg Ala Ala Val Val Gly
        275                 280                 285

Ala Asp Arg Ala Thr Leu Thr Asp Gly Leu Arg Ala Leu Ala Thr Gly
    290                 295                 300

Gly Asp Ala Pro His Leu Val His Gly Thr Ala Thr Gly Ser Pro Arg
305                 310                 315                 320

Pro Val Phe Val Phe Pro Gly Gln Gly Ser Gln Trp Pro Gly Met Ala
                325                 330                 335

Ala Glu Leu Leu Glu Thr Ser Glu Pro Phe His Asp Ser Val His Ala
            340                 345                 350

Cys Ala Asp Ala Leu Ala Glu Phe Val Asp Trp Ser Val Leu Asp Val
        355                 360                 365

Leu Arg Gln Ala Pro Asp Ala Pro Pro Leu Arg Arg Val Asp Val Leu
    370                 375                 380

Gln Pro Thr Leu Trp Ala Thr Met Val Ser Leu Ala Glu Val Trp Arg
385                 390                 395                 400

Ser Tyr Gly Val Glu Pro Ala Ala Val Gly His Cys Cys Gly Glu
                405                 410                 415

Ile Ala Ala Ala Gln Val Ala Gly Ala Leu Asp Met Arg Asp Ala Ala
            420                 425                 430

Arg Leu Leu Ala His Arg Ser Arg Ala Trp Leu Arg Leu Val Gly Lys
        435                 440                 445

Gly Thr Val Ile Ser Val Ala Thr Ser Gly Gln Asp Ile Thr Arg Arg
    450                 455                 460

Met Ala Ala Trp Pro Asp Ser Val Glu Leu Ala Ala Leu Asn Gly Pro
465                 470                 475                 480

Arg Ser Val Ala Leu Ala Gly Pro Pro Asp Val Leu Asp Gly Ile Val
                485                 490                 495

Asn Asp Leu Thr Asp Gln Gly Ile His Ala Lys Arg Ile Pro Gly Val
            500                 505                 510

Asp Thr Val Gly His Cys Ser Gln Val Glu Val Leu Arg Asp His Leu
        515                 520                 525

Leu Asp Val Leu Arg Pro Val Ser Pro Arg Pro Ala Ala Val Pro Phe
    530                 535                 540

Tyr Ser Thr Val Asp Gly Thr Glu Arg Asp Thr Thr Leu Asp Thr
545                 550                 555                 560

Asp Tyr Trp Tyr Leu Asn Thr Arg Ser Gln Val Arg Phe His Gln Ala
                565                 570                 575

Val Arg Asn Leu Leu Ala Ala Gly His Arg Ser Phe Val Glu Val Ser
            580                 585                 590

Pro His Pro Leu Leu Gly Ala Ser Ile Glu Asp Thr Ala Ala Glu Phe
        595                 600                 605
```

```
Gly Leu Asp Asp Val Ala Ala Val Gly Thr Leu Arg Arg Gly Gln Gly
    610                 615                 620

Gly Thr Arg Arg Val Leu Thr Ser Val Ala Glu Ala Tyr Val His Gly
625                 630                 635                 640

Ile Asp Ile Asp Phe Thr Pro Ala Phe Thr Gly Thr Thr Pro Asn Arg
                645                 650                 655

Ile Asp Leu Pro Thr Val Glu Asp His Gly Ile Glu Gly His Gly Asp
            660                 665                 670

Asp Gly Gly Glu Thr Trp Thr Asp Arg Val Arg Thr Leu Pro Asp Glu
        675                 680                 685

Gln Arg Glu Glu Ala Leu Leu Asp Leu Val Cys Arg Thr Val Ala Ala
    690                 695                 700

Val Leu Glu Ala Asp Pro Ala Gly Thr Ala Asp Ala Val Ala Pro Asp
705                 710                 715                 720

Thr Ala Phe Lys Glu Met Gly Leu Gly Ser Leu Ser Ala Val Arg Leu
                725                 730                 735

Arg Asn Gly Leu Arg Glu Ala Thr Gly Ala His Leu Pro Ala Thr Ile
            740                 745                 750

Ala Tyr Asp His Pro Thr Pro Ala Ala Leu Ala Arg His Leu Ala Met
        755                 760                 765

Thr Leu Phe Asp Ala Thr Gly Ala Ala Pro Val Pro Ala Pro Ser
    770                 775                 780

Arg Asp Asp Glu Pro Ile Asp Ala Glu Thr Ala Val Leu Thr Ala Leu
785                 790                 795                 800

Glu Arg Ala Asp Glu Ala Leu Glu Arg Leu Arg Ala Pro His Ala Arg
                805                 810                 815

Thr Pro Arg Gln Glu Thr Gly Arg Arg Ile Asp Glu Leu Leu Arg Ser
            820                 825                 830

Leu Thr Asp Lys Ala Arg Arg Met Arg Gln Ala Asp Ala Val Asp Asp
        835                 840                 845

Val Asp Asp Pro Ala Thr Asp Arg Phe Ala Ala Ala Thr Asp Asp Glu
    850                 855                 860

Met Phe Glu Leu Leu Glu Lys Arg Phe Gly Ile Ser
865                 870                 875

<210> SEQ ID NO 6
<211> LENGTH: 1571
<212> TYPE: PRT
<213> ORGANISM: Streptomyces parvulus

<400> SEQUENCE: 6

Met Ala His Glu Asp Lys Leu Arg His Leu Leu Lys Arg Val Ser Ala
1               5                   10                  15

Glu Leu Asp Asp Thr Gln Arg Arg Val Arg Glu Met Glu Glu Ser Glu
            20                  25                  30

Arg Glu Pro Ile Ala Ile Val Gly Met Ser Cys Arg Leu Pro Gly Gly
        35                  40                  45

Val Asn Ser Pro Gly Glu Phe Trp Ser Leu Leu Glu Ala Gly Thr Asp
    50                  55                  60

Ala Val Ser Glu Phe Pro Arg Asp Arg Gly Trp Asp Val Glu Asn Leu
65                  70                  75                  80

Tyr Asp Pro Asp Pro Asp Ala Pro Gly Arg Ser Tyr Val Arg Glu Gly
                85                  90                  95

Gly Phe Leu Asp Gly Ala Gly Gln Phe Asp Ala Ala Phe Phe Gly Ile
            100                 105                 110
```

```
Ser Pro Arg Glu Ala Leu Ala Met Asp Pro Gln Gln Arg Leu Leu Leu
            115                 120                 125

Glu Cys Ser Trp Glu Ala Ile Glu Arg Ser Arg Ile Asp Pro Lys Thr
130                 135                 140

Leu His Gly Ser Arg Thr Gly Val Phe Ala Gly Ser Asn Trp Gln Asp
145                 150                 155                 160

Tyr Asn Thr Leu Leu Leu Asn Ala Glu Glu Arg Ser Gln Ser Tyr Leu
                165                 170                 175

Ala Thr Gly Ala Ser Gly Ser Val Leu Ser Gly Arg Val Ser Tyr Thr
            180                 185                 190

Leu Gly Met Glu Gly Pro Ala Ile Thr Val Asn Thr Ala Cys Ser Ser
        195                 200                 205

Ser Leu Val Ala Val His Leu Ala Ala Arg Ser Leu Arg Ala Gly Glu
    210                 215                 220

Cys Asp Leu Ala Leu Ala Gly Ala Val Thr Val Met Ser Thr Pro Gln
225                 230                 235                 240

Leu Pro Val Ala Phe Ser Arg Gln Arg Gly Leu Ala Pro Asp Gly Arg
                245                 250                 255

Ser Lys Ala Phe Ala Val Ser Ala Asp Gly Met Gly Phe Gly Glu Gly
            260                 265                 270

Val Gly Val Leu Val Leu Glu Arg Leu Ser Val Ala Arg Arg Asn Gly
        275                 280                 285

His Arg Val Leu Ala Val Arg Gly Ser Ala Val Asn Gln Asp Gly
    290                 295                 300

Ala Ser Asn Gly Leu Thr Ala Pro Asn Gly Pro Ser Gln Gln Arg Val
305                 310                 315                 320

Ile Arg Ala Ala Leu Ala Ser Ala Gly Leu Gly Pro Ala Asp Val Asp
                325                 330                 335

Val Val Glu Ala His Gly Thr Gly Thr Arg Leu Gly Asp Pro Ile Glu
            340                 345                 350

Ala Gln Ala Leu Leu Ala Thr Tyr Gly Arg Gly Arg Asp Ala Glu Arg
        355                 360                 365

Pro Leu Trp Leu Gly Ser Val Lys Ser Asn Ile Gly His Ala Gln Ala
    370                 375                 380

Ala Ala Gly Val Ala Gly Val Ile Lys Met Val Leu Ala Met Glu Lys
385                 390                 395                 400

Gly Arg Leu Pro Arg Thr Leu His Val Asp Glu Pro Ser Gly Glu Val
                405                 410                 415

Asp Trp Asp Ser Gly Ala Val Arg Leu Leu Thr Glu Ala Arg Asp Trp
            420                 425                 430

Pro Ser Glu Glu Gly Arg Leu Arg Arg Ala Gly Val Ser Ser Phe Gly
        435                 440                 445

Ile Ser Gly Thr Asn Ala His Val Ile Ile Glu Glu Ala Pro Glu Glu
    450                 455                 460

Gly Glu Glu Pro Glu Ser Asp Ala Gly Gly Val Val Pro Trp Val Leu
465                 470                 475                 480

Ser Ala Arg Thr Glu Gly Ala Leu Gln Ala Gln Ala Val Gln Leu Ser
                485                 490                 495

Glu Phe Val Gly Glu Ser Ser Pro Val Asp Val Gly Trp Ser Leu Val
            500                 505                 510

Ser Thr Arg Ala Ala Phe Glu His Arg Ala Val Val Val Gly Arg Gly
        515                 520                 525
```

```
Arg Asp Glu Leu Val Arg Gly Leu Ser Glu Val Ala Gln Gly Arg Gly
530                 535                 540

Val Arg Gly Val Ala Ser Ser Ala Ser Gly Gly Leu Ala Phe Val Phe
545                 550                 555                 560

Ala Gly Gln Gly Ser Gln Arg Leu Gly Met Gly Arg Gly Leu Tyr Glu
                565                 570                 575

Arg Phe Pro Val Phe Ala Glu Ala Phe Asp Glu Val Cys Gly Arg Val
                580                 585                 590

Gly Pro Gly Val Arg Glu Val Val Phe Gly Ser Asp Ala Gly Glu Leu
            595                 600                 605

Asp Arg Thr Val Trp Ala Gln Ala Gly Leu Phe Ala Leu Glu Val Ala
610                 615                 620

Leu Phe Arg Leu Leu Glu Ser Trp Gly Val Arg Pro Gly Cys Leu Ile
625                 630                 635                 640

Gly His Ser Val Gly Glu Leu Ser Ala Ala Cys Val Ala Gly Leu Trp
                645                 650                 655

Ser Leu Glu Asp Ala Cys Arg Val Val Ala Ala Arg Ala Arg Leu Met
                660                 665                 670

Gln Ala Leu Pro Ala Gly Gly Val Met Val Ala Val Arg Ala Glu Ala
            675                 680                 685

Gly Glu Leu Ala Gly Phe Leu Gly Glu Asp Val Val Ile Ala Ser Val
690                 695                 700

Asn Ala Pro Gly Gln Val Val Ile Ala Gly Pro Glu Gly Gly Val Glu
705                 710                 715                 720

Arg Val Val Ala Ala Cys Gly Ala Arg Ser Arg Arg Leu Ala Val Ser
                725                 730                 735

His Ala Phe His Ser Pro Leu Val Glu Pro Met Leu Gly Glu Phe Arg
                740                 745                 750

Arg Val Val Glu Ser Val Ala Phe Gly Val Pro Ser Leu Arg Val Val
            755                 760                 765

Ser Asn Val Thr Gly Ala Trp Val Asp Pro Glu Glu Trp Gly Thr Pro
770                 775                 780

Glu Tyr Trp Val Arg Gln Val Arg Glu Pro Val Arg Phe Ala Asp Gly
785                 790                 795                 800

Val Ala Thr Leu Leu Asp Ala Gly Val Arg Thr Phe Val Glu Leu Gly
                805                 810                 815

Pro Ala Gly Ala Leu Thr Ser Met Val Ser His Cys Ala Asp Ala Thr
                820                 825                 830

Ala Thr Ser Val Thr Ala Val Pro Thr Leu Arg Pro Asp His Asp Glu
            835                 840                 845

Ser Arg Thr Val Leu Ser Ala Ala Ser Leu Tyr Val Gln Gly His
850                 855                 860

Pro Val Asp Trp Ala Pro Leu Phe Pro Arg Ala Arg Thr Val Asp Leu
865                 870                 875                 880

Pro Thr Tyr Pro Phe Gln His Gln His Tyr Trp Leu Asp Val Pro Pro
                885                 890                 895

Leu Phe Thr Ala Ser Ser Ala Ala Gln Asp Gly Gly Arg Tyr Arg
                900                 905                 910

Ile His Trp Arg Arg Leu Gly Thr Arg Asp Ser Gly Asp Arg Leu Ser
            915                 920                 925

Gly Arg Trp Leu Leu Leu Val Pro Glu Ser Asp Gly Thr Glu Pro Trp
930                 935                 940
```

-continued

Val Glu Gly Ala Glu Lys Met Leu Ala Glu Arg Gly Cys Glu Val Val
945                 950                 955                 960

His Val Pro Ile Ala Ala Thr Ala Asp Arg Asp Ala Met Val Gly Ala
            965                 970                 975

Val Arg Glu Ser Val Glu Asp Gly Arg Val Asp Gly Val Leu Ser Leu
        980                 985                 990

Leu Ala Leu Asp Gly Arg Pro His Pro Asp Ala Ala Ala Val Pro Thr
        995                 1000                1005

Gly Leu Val Ala Thr Ala Gln Val Val Gln Val Ser Asp Glu Leu
    1010                1015                1020

Gly Ile Gly Pro Leu Trp Val Ala Thr Arg Gln Ala Val Ser Val
    1025                1030                1035

Asp Gly Ala Asp Glu Ala Asp Gly Ala Gly Arg Thr Arg Lys Ala
    1040                1045                1050

Asp Asp Pro Ala Asp Val Ala Gln Ala Ala Val Trp Gly Leu Gly
    1055                1060                1065

Arg Val Ala Ala Leu Glu Lys Pro Arg Leu Trp Gly Gly Leu Val
    1070                1075                1080

Asp Leu Pro Ala Arg Ala Asp Glu Arg Met Arg Asp Leu Val Ala
    1085                1090                1095

Gln Ala Leu Thr Ala Pro Asp Ala Glu Asp Gln Leu Ala Val Arg
    1100                1105                1110

Ala Asp Gly Ile Ala Val Arg Arg Leu Val Arg Ser Ala Ala Ser
    1115                1120                1125

Ala Pro Ala Asp Asp Trp Gln Pro Ser Gly Thr Val Leu Val Thr
    1130                1135                1140

Gly Gly Thr Gly Gly Val Gly Ala Asn Val Ala Arg Trp Leu Val
    1145                1150                1155

Thr Gln Asp Ile Gln His Leu Leu Leu Val Ser Arg Arg Gly Pro
    1160                1165                1170

Asp Ala Pro Gly Ala Ala Glu Leu Leu Ala Glu Leu Ser Ala Ser
    1175                1180                1185

Gly Thr Ser Val Thr Ile Glu Pro Cys Asp Val Thr Asp Ala Asp
    1190                1195                1200

Ala Val Arg Arg Leu Ile Gly Ala Val Pro Ala Glu Arg Pro Leu
    1205                1210                1215

Ser Thr Val Val His Ala Ala Gly Val Leu Asp Asp Cys Leu Ile
    1220                1225                1230

Asp Ala Leu Thr Pro Gln Arg Leu Ala Ala Ala Leu Glu Val Lys
    1235                1240                1245

Ala Lys Gly Ala Leu Asn Leu His Glu Ala Ala Gly Glu Ala His
    1250                1255                1260

Leu Val Leu Phe Ser Ser Leu Ala Gly Thr Thr Gly Thr Lys Gly
    1265                1270                1275

Gln Gly Asn Tyr Ala Ala Ala Asn Ala Tyr Leu Asp Ala Leu Ala
    1280                1285                1290

Glu Arg Arg Arg Ala Asp Gly Leu Pro Ala Thr Ser Val Ala Trp
    1295                1300                1305

Gly Ala Trp Gln Gly Ala Gly Met Val Ala Asp Ala Ala Val Ala
    1310                1315                1320

His Arg Thr Arg Arg Tyr Gly Leu Pro Leu Met Ser Pro Asp Arg
    1325                1330                1335

Ala Val Ala Thr Leu Arg Gln Val Met Ala Glu Pro Val Ala Thr
1340                1345                1350

Gln Val Val Ala Asp Val Asp Trp Gln Arg Phe Val Ala Asp Phe
1355                1360                1365

Thr Ala Val Arg Pro Ser Arg Leu Leu Ala Asp Leu Pro Glu Val
1370                1375                1380

Arg Ser Leu Gly Glu Gln Arg Lys Asp Gly Pro Gly Gly Gln Gly
1385                1390                1395

Glu Glu Asp Gly Leu Ala Ser Lys Leu Ala Ala Leu Pro Glu Ala
1400                1405                1410

Asp Arg Arg Arg Ala Val Leu Asp Leu Val Glu Glu Leu Val Leu
1415                1420                1425

Gly Val Leu Gly His Glu Thr Arg Ala Ala Ile Gly Pro Asp Ser
1430                1435                1440

Ser Phe His Ala Ile Gly Phe Asp Ser Leu Thr Ala Val Glu Leu
1445                1450                1455

Arg Asn Leu Leu Thr Val Arg Leu Gly Met Lys Leu Pro Ala Thr
1460                1465                1470

Leu Val Tyr Asp His Pro Thr Leu Ser Ser Leu Ala Asp His Leu
1475                1480                1485

His Glu Gln Leu Val Ile Asp Gly Thr Pro Met Thr Asp Thr Ala
1490                1495                1500

Ala Asp Leu Leu Ala Glu Leu Asp Ala Leu Ala Ala Arg Leu Ala
1505                1510                1515

Ala Val Gly Leu Glu Pro Glu Ala Arg Ala Arg Ile Gly Arg Arg
1520                1525                1530

Leu Lys Asp Met Gln Thr Ala Cys Glu Pro Arg Ser Glu Ser Ser
1535                1540                1545

Arg Asp Leu Lys Ser Ala Ser Arg Thr Glu Val Leu Asp Phe Leu
1550                1555                1560

Thr Asn Glu Leu Gly Ile Ser Arg
1565                1570

<210> SEQ ID NO 7
<211> LENGTH: 2164
<212> TYPE: PRT
<213> ORGANISM: Streptomyces thioluteus

<400> SEQUENCE: 7

Met Thr Asn Asp Ala Lys Thr Leu Glu Tyr Leu Lys Arg Leu Thr Ala
1               5                   10                  15

Glu Leu Leu Glu Thr Arg Glu Arg Leu Arg Thr Ala Glu Ala Ala Asp
                20                  25                  30

Gln Glu Pro Val Ala Val Val Ser Met Gly Cys Arg Tyr Pro Gly Gly
            35                  40                  45

Val Ser Ser Pro Glu Asp Leu Trp Arg Leu Val Thr Asp Gly Thr Asp
        50                  55                  60

Ala Ile Ala Pro Phe Pro Ala Asp Arg Gly Trp Asn Val Asp Asp Leu
65                  70                  75                  80

Phe Asp Pro Asp Pro Asp Arg Pro Gly Arg Thr Tyr Thr Leu Glu Gly
                85                  90                  95

Gly Phe Val Asp Gly Ala Ala Glu Phe Asp Ala Asp Leu Phe Gly Ile
            100                 105                 110

Ser Pro Arg Glu Ala Thr Ala Met Asp Pro Gln Gln Arg Leu Leu Leu
        115                 120                 125

```
Glu Thr Ala Trp Glu Thr Phe Glu Arg Ala Gly Thr Asp Pro Gly Ser
130                 135                 140

Leu Arg Gly Arg Pro Val Gly Val Phe Val Gly Ser Leu Phe Val Ala
145                 150                 155                 160

Gly Gly Ser Gly Val Gly Val Ala Glu Gly Ala Glu Gly Tyr His Met
                165                 170                 175

Thr Gly Asn Ala Ala Ser Val Leu Ser Gly Arg Leu Ala Tyr Ala Phe
            180                 185                 190

Gly Leu Glu Gly Pro Ala Val Thr Val Asp Thr Ala Cys Ser Ala Ser
                195                 200                 205

Leu Val Ala Val His Gln Ala Val Gln Ala Leu Arg Gln Gly Glu Cys
210                 215                 220

Ala Leu Ala Leu Ala Gly Gly Ser Thr Val Met Thr Thr Pro Gly Val
225                 230                 235                 240

Phe Thr Glu Phe Ser Arg Gln Arg Gly Leu Ala Pro Asp Gly Arg Cys
                245                 250                 255

Lys Ala Phe Ala Thr Ala Ala Asp Gly Thr Gly Phe Gly Glu Gly Val
            260                 265                 270

Gly Leu Val Leu Leu Glu Lys Leu Ser Asp Ala Arg Lys Asn Gly His
            275                 280                 285

Pro Val Leu Ala Val Ile Arg Gly Ser Ala Val Asn Gln Asp Gly Ala
290                 295                 300

Ser Asn Gly Leu Thr Ala Pro Asn Gly Pro Ser Gln Gln Arg Val Ile
305                 310                 315                 320

Arg Gln Ala Leu Ala Ala Arg Val Ser Ala Asp Glu Val Asp Val
                325                 330                 335

Val Glu Ala His Gly Thr Gly Thr Gly Leu Gly Asp Pro Val Glu Ala
                340                 345                 350

Gln Ala Leu Leu Ala Thr Tyr Gly Gln Gly Arg Pro Asp Asp Arg Pro
                355                 360                 365

Leu Trp Leu Gly Ser Ile Lys Ser Asn Leu Gly His Thr Gln Gly Ala
370                 375                 380

Ala Gly Val Ala Gly Leu Ile Lys Met Val Met Ala Val Arg His Gly
385                 390                 395                 400

Val Leu Pro Met Thr Leu His Val Asp Glu Pro Ser Ala His Val Asp
                405                 410                 415

Trp Asp Ser Gly Ala Val Arg Leu Leu Thr Gly Asn His Asp Trp Pro
            420                 425                 430

Glu Thr Gly Arg Pro Arg Arg Ala Gly Val Ser Ser Phe Gly Ile Ser
            435                 440                 445

Gly Thr Asn Ala His Leu Ile Leu Glu Gln Ala Pro Asp Ala Glu Glu
            450                 455                 460

Ser Asp Ala Glu Pro Ala Ser Gly Ala Pro Ala Arg Ile Pro Trp Val
465                 470                 475                 480

Leu Ala Ala Arg Gly Glu Glu Ala Leu Arg Ala Gln Ala Glu Arg Leu
                485                 490                 495

Leu Thr Glu Val Arg Asp Arg Pro Glu Leu Arg Pro Val Asp Val Gly
            500                 505                 510

His Ala Leu Ala Thr Ser Arg Ala Ala Leu Asp Gln Arg Ala Val Val
            515                 520                 525

Trp Ala Asp Gly Arg Asp Gly Leu Leu Ala Ala Leu Thr Ala Leu Ala
530                 535                 540
```

-continued

Glu Glu Arg Pro Ala Pro Gly Val Val His Gly Thr Val Ala Asp Gly
545                 550                 555                 560

Arg Leu Ala Phe Leu Phe Ser Gly Gln Gly Ser Gln Arg Pro Gly Met
            565                 570                 575

Gly His Glu Leu Thr Glu Ser Phe Pro Val Phe Ala Glu Lys Leu Asp
            580                 585                 590

Glu Val Cys Gly His Leu Asp Arg His Leu Asp Arg Pro Leu Arg Glu
        595                 600                 605

Leu Leu Phe Ala Ala Glu Gly Thr Pro Glu Ala Ala Leu Leu Glu Gln
        610                 615                 620

Thr Gly Tyr Thr Gln Ala Ala Leu Phe Ala His Glu Val Ala Leu His
625                 630                 635                 640

His Leu Leu Thr His Trp Gly Ile Thr Pro Asp Leu Leu Gly His
                645                 650                 655

Ser Ile Gly Glu Leu Thr Ala Ala His Val Ala Gly Val Leu Ser Leu
                660                 665                 670

Glu Asp Ala Cys Ala Leu Val Ala Ala Arg Gly Arg Leu Met Gln Gln
            675                 680                 685

Leu Pro Gly Ala Gly Ala Met Leu Ser Val Gln Ala Thr Glu Ala Glu
            690                 695                 700

Val Leu Pro Trp Val Thr Glu His Ala His Glu Met Ser Ile Ala Ala
705                 710                 715                 720

Val Asn Gly Pro Arg Ser Val Val Ser Gly Ala Glu Ser Ala Val
                725                 730                 735

Leu Glu Phe Ala Glu His Trp Lys Asn Glu Gly Arg Lys Thr Lys Arg
            740                 745                 750

Leu Arg Val Ser His Ala Phe His Ser Pro Gln Met Asp Gly Met Leu
            755                 760                 765

Gln Glu Phe Ala Arg Val Ala Glu Lys Leu Ala Phe His Pro Pro Arg
            770                 775                 780

Ile Pro Val Val Ser Asn Val Thr Gly Glu Val Ala Thr Ala Glu Gln
785                 790                 795                 800

Leu Cys Ser Pro Ala Tyr Trp Val Arg His Ala Arg Glu Ala Val Arg
                805                 810                 815

Phe His Asp Gly Ile Arg Arg Leu Val Ala Glu Gly Ala His Val Phe
            820                 825                 830

Leu Glu Val Gly Pro Ser Gly Val Leu Thr Ala Met Ala Gln Asp Cys
            835                 840                 845

Leu Ala Asp Glu Pro Gly Thr Val Thr Ala Ala Val Ser Arg Gly Gly
850                 855                 860

Arg Pro Glu Ala Asp Ala Ala Leu Ala Ala Val Ala Glu Ala Tyr Val
865                 870                 875                 880

His Gly Val Arg Val Asp Trp Asp Arg Phe Phe Ala Gly Thr Gly Ala
                885                 890                 895

Arg Arg Ile Asp Leu Pro Thr Tyr Ala Phe Arg Arg Ser Phe Pro
            900                 905                 910

Trp Ile Gln Ala Ala Pro Asp Ala Asp Val Thr Thr Ala Gly Leu Ala
            915                 920                 925

Gly Leu Gly His Pro Leu Leu Gly Ala Ser Leu Glu Leu Ala Asp Ala
    930                 935                 940

Gln Gly Ala Ala Leu Ser Gly Arg Leu Ser Ala Arg Thr Glu Ser Trp
945                 950                 955                 960

-continued

```
Leu Ala Asp His Val Val Leu Gly Ser Thr Leu Val Pro Gly Thr Ala
                965                 970                 975
Val Val Glu Met Ala Val Arg Ala Gly Ala Glu Thr Gly Cys Gly Arg
            980                 985                 990
Leu Ala Glu Leu Thr Gln Glu Ala Pro Leu Ala Val Pro Glu Arg Gly
        995                 1000                1005
Ala Val His Leu Gln Val Arg Val Gly Pro Ala Gly Glu Gln Gly
    1010                1015                1020
His Arg Pro Val Gly Val Tyr Ser Arg Pro Glu Asp Ala Glu Pro
    1025                1030                1035
Asp Glu Pro Trp Ala Cys His Ala Arg Gly Val Leu Ala Pro Glu
    1040                1045                1050
Ala Ala Pro Val Pro Ala Gly Thr Gly Gly Ala Trp Pro Pro Ser
    1055                1060                1065
Gly Ala Glu Pro Val Pro Leu Asp Gly Phe Tyr Glu Arg Leu Ala
    1070                1075                1080
Ala Glu Gly Phe Ala Tyr Gly Pro Ala Phe Gln Gly Leu Thr Arg
    1085                1090                1095
Ala Trp Arg Leu Gly Asp Glu Val Leu Ala Glu Ile Thr Leu Pro
    1100                1105                1110
Glu Gly Ala Cys Ser Gly Ala Asp Arg Tyr Gly Val His Pro Ala
    1115                1120                1125
Leu Leu Asp Ala Ala Leu His Thr Ala Leu Leu Lys Glu Glu Ala
    1130                1135                1140
Ser Asp Thr Ser Gln Val Arg Ile Pro Phe Ala Trp His Glu Val
    1145                1150                1155
Ser Phe His Gly Gly Ser Ala Pro Val Leu Arg Ala Arg Leu Thr
    1160                1165                1170
Pro Ser Gly Thr Asp Thr Val Ser Leu Ala Leu Trp Asp Glu His
    1175                1180                1185
Gly Thr Pro Val Ala Ser Val Gly Ser Leu Val Ser Arg Pro Val
    1190                1195                1200
Ser Ala Arg Gln Leu Arg Ala Thr Arg Thr His Asp Thr Leu Phe
    1205                1210                1215
Arg Leu Asp Trp Val Glu Thr Thr Ile Thr Pro Ala Ala Ala Arg
    1220                1225                1230
Cys Ala Val Leu Gly Asp Asp Glu Leu Ala Gly Ala Leu Ser Val
    1235                1240                1245
Pro Ala Phe Ala Asp Leu Ala Ala Leu Glu Ser Ala Asp Pro Val
    1250                1255                1260
Pro Glu Leu Val Leu Tyr Pro Cys Leu Gly Asp Asp Ala Glu Asp
    1265                1270                1275
Asp Arg Ala Asp Ala Ala Arg Ser Leu Thr Ala Arg Val Leu Gly
    1280                1285                1290
Val Leu Gln Ala Trp Val Ala Asp Glu Arg Trp Ala Thr Thr Arg
    1295                1300                1305
Leu Ala Leu Val Thr Arg Gly Ala Met Ser Val Thr Asp Arg Glu
    1310                1315                1320
Gln Val Thr Asp Leu Pro Ala Ala Ala Val Trp Gly Leu Val Arg
    1325                1330                1335
Ser Ala Gln Ala Glu His Pro Gly Arg Phe Val Leu Ala Asp Leu
    1340                1345                1350
```

```
Asp Gly Asp Thr Ala Ser Ala Ala Ala Leu Pro Gly Ile Leu Ala
    1355                1360                1365

Ala Ser Gly Asp Glu Pro Gln Leu Ala Leu Arg Glu Gly Ala Val
    1370                1375                1380

Leu Val Pro Arg Leu Ala Arg Gly Val Pro Ser Gly Thr Leu Val
    1385                1390                1395

Pro Pro Pro Gly Thr Arg Asp Trp His Leu Glu Leu Thr Gly Gly
    1400                1405                1410

Gly Thr Val Asp Asp Leu Ala Leu Thr Pro Phe Pro Glu Ala Ala
    1415                1420                1425

Ala Pro Leu Ala Pro Gly Gln Val Arg Val Ala Val Arg Ala Ala
    1430                1435                1440

Gly Leu Asn Phe Arg Asp Val Val Met Ala Leu Gly Met Val Asp
    1445                1450                1455

Asp Arg Arg Ala Leu Gly Gly Glu Ile Ala Gly Ile Val Thr Glu
    1460                1465                1470

Ala Gly Pro Gly Val Thr Gly Phe Ala Pro Gly Asp Arg Val Phe
    1475                1480                1485

Gly Leu Ala Asp Gly Cys Ile Gly Pro Val Ala Val Val Asp His
    1490                1495                1500

Arg Leu Ile Ala Arg Ile Pro Glu Gly Trp Ser Phe Pro Gln Ala
    1505                1510                1515

Ala Ser Val Pro Val Thr Phe Leu Thr Ala Tyr Tyr Gly Leu Val
    1520                1525                1530

Asp Leu Ala Gly Val Arg Pro Gly Asp Arg Val Leu Val His Ala
    1535                1540                1545

Ala Ala Gly Gly Val Gly Met Ala Ala Val Gln Leu Ala Arg His
    1550                1555                1560

Leu Gly Ala Glu Val Phe Ala Thr Ala Gly Pro Ala Lys Trp Asp
    1565                1570                1575

Thr Val Arg Ala Leu Gly Ile Asp Asp Asp His Leu Ala Ser Ser
    1580                1585                1590

Arg Thr Asp Glu Phe Glu Thr Arg Phe Ala Ala Glu Asp Gly Gly
    1595                1600                1605

Arg Gly Ile Asp Val Val Leu Asn Ser Leu Ala Gly Glu Met Ala
    1610                1615                1620

Asp Ala Ser Leu Arg Leu Val Arg Pro Gly Gly Arg Phe Ile Glu
    1625                1630                1635

Met Gly Lys Thr Asp Ile Arg Asp Ala Asp Glu Val Ala Ala Ala
    1640                1645                1650

Tyr Glu Gly Val Val Tyr Arg Ala Phe Asp Leu Met Asp Gly Gly
    1655                1660                1665

Ala Glu Cys Ile Ala Arg Ile Phe Ala Glu Leu Leu Ala Leu Phe
    1670                1675                1680

Glu Gly Gly Lys Ile Gln Leu Val Pro Val Thr Thr Trp Asp Val
    1685                1690                1695

Arg Gln Ala Pro Glu Ala Phe Arg Tyr Phe Ala Gln Ala Arg His
    1700                1705                1710

Val Gly Lys Ile Val Leu Thr Val Pro Pro Ala Trp Asp Pro Glu
    1715                1720                1725

Gly Thr Val Leu Val Thr Gly Ala Ser Gly Gly Val Ala Ala His
    1730                1735                1740
```

```
Leu Val Arg His Leu Val Arg Thr His Asp Val Arg His Leu Leu
    1745                1750                1755
Leu Ala Ser Arg Arg Gly Pro Asp Ala Glu Gly Met Asp Glu Leu
    1760                1765                1770
Ile Ala Glu Leu Arg Glu Ser Gly Ala His Ser Val Arg Ala Val
    1775                1780                1785
Ala Cys Asp Cys Val Asp Arg Thr Ala Val Ala Asp Leu Leu Ala
    1790                1795                1800
Ser Ile Pro Asp Glu His Pro Leu Thr Ala Val Val His Thr Val
    1805                1810                1815
Gly Val Val Asp Asp Gly Val Leu Glu Thr Met Thr Pro Glu Arg
    1820                1825                1830
Ile Asp Ala Val Phe Arg Pro Lys Ala Asp Gly Ala Trp His Leu
    1835                1840                1845
His Glu Leu Thr Arg Asp Arg Asp Leu Ala Ala Phe Ala Val Cys
    1850                1855                1860
Ser Ser Val Ala Gly Thr Leu Gly Ser Ala Ala Gln Ala Asn Tyr
    1865                1870                1875
Ala Ala Ala Asn Ala Phe Leu Asp Ala Leu Ala Ala His Arg Arg
    1880                1885                1890
Asp His Gly Leu Pro Ala Thr Ser Leu Ala Trp Gly Met Trp Ala
    1895                1900                1905
Gly Thr Gly Gly Met Ala Ala Asn Leu Ser Arg Ala Asp Leu Asp
    1910                1915                1920
Arg Met Gln Arg Ser Gly Ile Ser Gly Leu Ser Thr Glu Glu Gly
    1925                1930                1935
Leu Ala Leu Phe Asp Ala Ala Leu Ala Ala Gly Arg Pro Val Trp
    1940                1945                1950
Leu Pro Ala Arg Leu Asp Ala Lys Ala Leu Arg Thr Ala Ala Gly
    1955                1960                1965
Gly Gly Ser Leu Pro Ala Pro Leu Arg Gly Leu Val His Val Pro
    1970                1975                1980
Ala Ala Asp Ala Gly Pro Leu Pro Ala Asp Ala Leu Arg Gly
    1985                1990                1995
Arg Leu Ala Ser Leu Ala Pro Glu Glu Arg His Glu Ala Val Leu
    2000                2005                2010
Asp Val Val Arg Ala Gln Val Ala Val Val Leu Gly His Gly Ala
    2015                2020                2025
Pro Glu Gly Ile Asp Pro Gln Arg Ala Phe Lys Asp Leu Gly Phe
    2030                2035                2040
Asp Ser Leu Thr Ala Val Glu Leu Arg Asn Arg Leu Asn Ala Ala
    2045                2050                2055
Ala Gly Leu Thr Leu Pro Ala Thr Leu Val Phe Asp His Pro Thr
    2060                2065                2070
Pro Ala Ala Leu Thr Asp His Ile Glu Ser Val Leu Leu Ala Gly
    2075                2080                2085
Leu Gly Ser Pro Ala Asp Pro Leu Leu Ala Arg Leu Asp Asp Trp
    2090                2095                2100
Ala Ala Gly Leu Ala Ala Thr Ala Leu Asp Asp Asp Glu Arg Glu
    2105                2110                2115
Arg Val Ala Ala Arg Leu Arg Ala Leu Ala Gly Gln Trp Gly Ala
    2120                2125                2130
```

```
Pro Asp Asp Gly Ala Thr Ser Ile Ala Asp Glu Leu Asp Gly Ala
    2135                2140                2145

Thr Asp Asp Glu Val Leu Asp Phe Ile Ser Asn Glu Leu Gly Ile
    2150                2155                2160

Ser

<210> SEQ ID NO 8
<211> LENGTH: 2175
<212> TYPE: PRT
<213> ORGANISM: Streptomyces antibioticus

<400> SEQUENCE: 8

Met His Met Val Gly Val Glu Glu Lys Leu Arg Asp Tyr Leu Arg Arg
1               5                   10                  15

Val Thr Gly Glu Leu Ser Glu Thr Arg Gln Arg Leu Lys Glu Ala Glu
            20                  25                  30

Ala Glu Ser Arg Glu Pro Ile Ala Ile Val Ser Met Ala Cys Arg Phe
        35                  40                  45

Pro Gly Gly Ile Glu Ser Pro Gln Asp Tyr Trp Arg Leu Leu Ala Glu
    50                  55                  60

Gly Arg Asp Ala Val Ala Gly Phe Pro Asp Asp Arg Gly Trp Asp Leu
65                  70                  75                  80

Asp Asn Leu Phe Asp Pro Asp Pro Asp Ala Pro Gly Lys Ser Tyr Ala
                85                  90                  95

Arg Glu Gly Ala Phe Val His Gly Ala Ser Glu Phe Asp Ala Glu Leu
            100                 105                 110

Phe Gly Ile Ser Pro Arg Glu Ala Leu Ser Met Asp Pro Gln Gln Arg
        115                 120                 125

Leu Leu Leu Glu Ala Ala Trp Glu Val Phe Glu Arg Ala Gly Leu Asp
    130                 135                 140

Pro Gly Ala Leu Lys Gly Arg Asp Ile Gly Val Phe Ala Gly Ala Ala
145                 150                 155                 160

Trp Ser Asp Tyr Val Ser Gly Ser Arg Lys Val Pro Asp Ser Ala Glu
                165                 170                 175

Gly Tyr Ala Ile Thr Gly Gly Ser Ser Val Leu Ser Gly Arg Val
            180                 185                 190

Ala Tyr Thr Phe Gly Leu Glu Gly Pro Ala Val Thr Val Asp Thr Ala
        195                 200                 205

Cys Ser Ser Ser Leu Val Ala Met His Leu Ala Ser Gln Ala Leu Arg
    210                 215                 220

Ser Gly Glu Cys Ser Met Ala Leu Ala Gly Gly Val Ser Val Leu Val
225                 230                 235                 240

Ser Pro Tyr Pro Phe Val Gly Phe Ser Arg Gln Arg Gly Leu Ala Pro
                245                 250                 255

Asp Gly Arg Cys Lys Pro Phe Ala Asp Arg Ala Asp Gly Thr Gly Trp
            260                 265                 270

Gly Glu Gly Val Gly Met Leu Leu Leu Glu Arg Leu Ser Asp Ala Arg
        275                 280                 285

Arg Asn Gly His Glu Val Leu Ala Val Leu Arg Gly Ser Ala Val Asn
    290                 295                 300

Gln Asp Gly Ala Ser Ser Gly Leu Thr Ala Pro Asn Gly Pro Ser Gln
305                 310                 315                 320

Gln Arg Val Ile Arg Ala Ala Leu Ala Asn Ala Gly Leu Thr Ala Ser
                325                 330                 335
```

```
Asp Val Asp Ala Val Glu Ala His Gly Thr Gly Thr Ser Leu Gly Asp
                340                 345                 350

Pro Ile Glu Ala Gln Ala Leu Leu Ala Thr Tyr Gly Gln Gly Arg Pro
            355                 360                 365

Glu Gly Arg Pro Leu Trp Leu Gly Ser Val Lys Ser Asn Ile Ala His
        370                 375                 380

Thr Gln Ala Thr Ala Gly Ala Ala Gly Val Ile Lys Met Val Leu Ala
385                 390                 395                 400

Met Arg His Gly Leu Leu Pro Lys Ser Leu His Val Asp Ala Pro Ser
                405                 410                 415

Thr Asn Val Asp Trp Ser Ala Gly Ala Val Glu Leu Leu Thr Val Ala
            420                 425                 430

Arg Glu Trp Pro Glu Val Asp Arg Pro Trp Arg Ala Gly Val Ser Ser
        435                 440                 445

Phe Gly Val Ser Gly Thr Asn Ala His Val Ile Val Glu Glu Ala Pro
    450                 455                 460

Glu Ser Ser Ala Asp Ala Val Ala Glu Ser Gly Val Arg Val Pro Val
465                 470                 475                 480

Pro Val Val Pro Trp Val Val Ser Ala Arg Ser Ala Glu Gly Leu Ala
                485                 490                 495

Ala Gln Ala Glu Arg Leu Ala Arg Phe Val Gly Glu Arg Ser Asp Gln
            500                 505                 510

Asp Pro Val Asp Ile Gly Phe Ser Leu Val Arg Ser Arg Ser Leu Leu
        515                 520                 525

Glu His Arg Ala Val Val Leu Gly Lys Gly Arg Asp Asp Leu Val Ala
    530                 535                 540

Gly Leu Ala Ser Leu Ala Ser Asp Gly Ser Ala Thr Gly Val Val Ser
545                 550                 555                 560

Gly Val Ala Arg Gly Arg Ala Arg Val Ala Phe Gly Phe Ser Gly Gln
                565                 570                 575

Gly Ala Gln Arg Val Gly Met Gly Ala Glu Leu Ala Ser Val Tyr Pro
            580                 585                 590

Val Phe Ala Glu Ala Leu Ala Glu Val Thr Gly Ala Leu Gly Leu Asp
        595                 600                 605

Pro Glu Val Phe Gly Asp Val Asp Arg Leu Gly Arg Thr Glu Val Thr
    610                 615                 620

Gln Ala Ala Leu Phe Ala Phe Glu Val Ala Val Arg Leu Leu Glu
625                 630                 635                 640

Ser Phe Gly Val Arg Pro Asp Val Leu Ile Gly His Ser Ile Gly Glu
                645                 650                 655

Ile Ala Ala Ala Tyr Val Ala Gly Val Phe Ser Leu Gly Asp Ala Ala
            660                 665                 670

Ala Leu Val Gly Ala Arg Gly Arg Leu Met Gln Ala Leu Pro Ala Gly
        675                 680                 685

Gly Val Met Val Ala Val Gln Ala Gly Glu Ala Glu Val Ala Ala
    690                 695                 700

Leu Glu Gly Phe Ala Asp Arg Val Ser Leu Ala Ala Val Asn Gly Pro
705                 710                 715                 720

Ser Ser Val Val Val Ser Gly Glu Ala Glu Ala Val Glu Gln Val Val
                725                 730                 735

Ala Arg Leu Gly Lys Val Lys Ser Lys Arg Leu Arg Val Ser His Ala
            740                 745                 750
```

-continued

```
Phe His Ser Pro Leu Met Glu Pro Met Leu Ala Asp Phe Arg Gln Val
            755                 760                 765

Ala Glu Gln Ile Thr Tyr Asn Glu Pro Gln Leu Pro Val Val Ser Asn
770                 775                 780

Val Ser Gly Arg Leu Ala Glu Pro Gly Glu Leu Thr Thr Pro Asp Tyr
785                 790                 795                 800

Trp Val Arg His Val Arg Glu Ala Val Arg Phe Gly Asp Gly Val Arg
                805                 810                 815

Ala Leu Ala Ala Asp Gly Val Gly Val Leu Val Glu Val Gly Pro Asp
                820                 825                 830

Ser Val Leu Thr Ala Leu Ala Arg Glu Ser Leu Asp Gly Glu Asp Gly
            835                 840                 845

Leu Arg Ala Val Pro Leu Leu Arg Lys Asp Arg Pro Glu Pro Glu Thr
850                 855                 860

Leu Leu Thr Gly Val Ala Gln Ala Phe Thr His Gly Val Gln Val Asp
865                 870                 875                 880

Trp Pro Ala Leu Leu Pro Gly Gly Arg Val Glu Leu Pro Thr Tyr
                885                 890                 895

Ala Phe Gln Arg Arg Arg Tyr Trp Leu Glu Asp Ala Asp Pro Thr Gly
                900                 905                 910

Gly Asp Pro Ala Ala Leu Gly Leu Thr Ala Ala Asp His Pro Leu Leu
            915                 920                 925

Gly Ala Ala Val Pro Leu Ala Glu Asp Gln Gly Ile Val Ile Thr Ser
            930                 935                 940

Arg Leu Ser Leu Arg Thr His Pro Trp Leu Ala Asp His Glu Ile Gly
945                 950                 955                 960

Gly Thr Val Leu Leu Pro Gly Ala Gly Leu Val Glu Ile Ala Leu Arg
                965                 970                 975

Ala Gly Asp Glu Val Gly Cys Gly Arg Val Glu Glu Leu Thr Leu Glu
            980                 985                 990

Ile Pro Leu Val Val Pro Gln Glu  Gly Gly Val Thr Val  Gln Ile Arg
            995                 1000                1005

Val Gly  Ala Pro Asp Glu Ser  Gly Trp Arg Pro Met   Thr Val His
    1010                1015                1020

Ser Arg  Thr Asp Pro Glu Glu  Glu Trp Thr Arg His   Val Ser Gly
    1025                1030                1035

Val Leu  Ser Pro Asp Val Pro  Thr Glu Arg Tyr Asp  Leu Gly Ala
    1040                1045                1050

Trp Pro  Pro Ala Gly Ala Thr  Pro Val Glu Leu Asp  Gly Phe Tyr
    1055                1060                1065

Glu Ala  Tyr Ala Arg Leu Gly  Tyr Ala Tyr Gly Pro  Ser Phe Gln
    1070                1075                1080

Gly Leu  Arg Ala Ala Trp Arg  Arg Gly Asp Glu Val  Phe Ala Glu
    1085                1090                1095

Val Ser  Leu Pro Val Glu Glu  Gln Glu Thr Ala Gly  Arg Phe Thr
    1100                1105                1110

Leu His  Pro Ala Leu Leu Asp  Ala Ala Leu Gln Ser  Ala Gly Ala
    1115                1120                1125

Gly Ala  Phe Phe Asp Ser Gly  Gly Ser Met Arg Leu  Pro Phe Ala
    1130                1135                1140

Trp Ser  Gly Val Ser Val Phe  Ala Ala Gly Ala Ser   Thr Val Arg
    1145                1150                1155
```

-continued

```
Val Arg Leu Ser Pro Ala Gly Pro Asp Ala Val Thr Val Ala Leu
1160                1165                1170
Ala Asp Pro Thr Gly Ala Pro Val Ala Leu Val Glu Arg Leu Leu
1175                1180                1185
Ile Pro Glu Met Ser Pro Glu Gln Leu Glu Arg Val Arg Gly Glu
1190                1195                1200
Glu Lys Glu Ala Pro Tyr Val Leu Asp Trp Val Pro Val Glu Val
1205                1210                1215
Pro Ala Asp Asp Leu Val Arg Pro Glu Arg Trp Thr Leu Leu Gly
1220                1225                1230
Gly Ala Asp Ala Gly Val Gly Leu Asp Val Ala Gly Ala Phe Ala
1235                1240                1245
Ser Leu Glu Pro Ser Asp Gly Ala Pro Glu Phe Val Val Leu Pro
1250                1255                1260
Cys Val Pro Pro Thr Ser Pro Thr Arg Ala Ala Asp Val Arg Gln
1265                1270                1275
Ser Thr Leu Gln Ala Leu Thr Val Leu Gln Asn Trp Val Thr Asp
1280                1285                1290
Glu Arg His Ala Asp Ser Arg Leu Val Leu Val Thr Arg Arg Ala
1295                1300                1305
Val Gly Val Gly Ala His Asp Asp Val Pro Asp Leu Thr His Ala
1310                1315                1320
Ala Leu Trp Gly Leu Val Arg Ser Ala Gln Thr Glu Asn Pro Gly
1325                1330                1335
Arg Phe Leu Leu Val Asp Leu Asp Glu Gly Ala Glu Leu Ala Glu
1340                1345                1350
Val Leu Pro Gly Ala Leu Gly Ser Gly Glu Ser Gln Val Ala Val
1355                1360                1365
Arg Ala Gly Arg Val Leu Ala Ala Arg Leu Ala Arg Ser Gly Ser
1370                1375                1380
Gly Gly Ala Glu Leu Val Pro Pro Ala Gly Ala Pro Trp Arg Leu
1385                1390                1395
Asp Thr Thr Ser Pro Gly Thr Leu Glu Asn Leu Ala Leu Val Pro
1400                1405                1410
Ser Ala Glu Glu Pro Leu Gly Pro Leu Asp Val Arg Val Ser Val
1415                1420                1425
Arg Ala Ala Gly Leu Asn Phe Arg Asp Val Leu Ile Ala Leu Gly
1430                1435                1440
Met Tyr Pro Gly Asp Ala Arg Met Gly Gly Glu Gly Ala Gly Val
1445                1450                1455
Val Thr Asp Val Gly Ser Glu Val Thr Thr Leu Ala Pro Gly Asp
1460                1465                1470
Arg Val Met Gly Met Leu Ser Ser Ala Phe Gly Pro Thr Ala Val
1475                1480                1485
Ser Asp His Arg Ala Leu Val Arg Val Pro Asp Trp Ser Phe
1490                1495                1500
Glu Gln Ala Ala Ser Val Pro Thr Val Phe Ala Thr Ala Tyr Tyr
1505                1510                1515
Gly Leu Val Asp Leu Ala Glu Leu Arg Ala Gly Gln Ser Val Leu
1520                1525                1530
Val His Ala Ala Ala Gly Gly Val Gly Met Ala Ala Val Gln Leu
1535                1540                1545
```

```
Ala Arg His Leu Gly Ala Glu Val Phe Gly Thr Ala Ser Thr Gly
1550             1555                 1560

Lys Trp Asp Ser Leu Arg Ala Gly Gly Leu Asp Ala Glu His Ile
1565             1570                 1575

Ala Ser Ser Arg Thr Val Glu Phe Glu Glu Thr Phe Leu Ala Ala
1580             1585                 1590

Thr Ala Gly Arg Gly Val Asp Val Val Leu Asp Ser Leu Ala Gly
1595             1600                 1605

Glu Phe Val Asp Ala Ser Leu Arg Leu Leu Pro Arg Gly Gly Arg
1610             1615                 1620

Phe Val Glu Met Gly Lys Ala Asp Ile Arg Asp Ala Glu Arg Val
1625             1630                 1635

Ala Ala Asp His Pro Gly Val Thr Tyr Arg Ser Phe Asp Leu Leu
1640             1645                 1650

Glu Ala Gly Leu Asp Arg Phe Gln Glu Ile Leu Thr Glu Val Val
1655             1660                 1665

Arg Leu Phe Glu Arg Gly Val Leu Arg His Leu Pro Val Thr Ala
1670             1675                 1680

Trp Asp Val Arg Arg Ala Ala Glu Ala Phe Arg Phe Val Ser Gln
1685             1690                 1695

Ala Arg His Val Gly Lys Asn Val Leu Val Met Pro Arg Val Trp
1700             1705                 1710

Asp Arg Asp Gly Thr Val Leu Ile Thr Gly Gly Thr Gly Ala Leu
1715             1720                 1725

Gly Ala Leu Val Ala Arg His Leu Val Ala Glu His Gly Met Arg
1730             1735                 1740

Asn Val Leu Leu Ala Gly Arg Arg Gly Val Asp Ala Pro Gly Ala
1745             1750                 1755

Arg Glu Leu Leu Ala Glu Leu Glu Thr Ala Gly Ala Gln Val Ser
1760             1765                 1770

Val Val Ala Cys Asp Val Ala Asp Arg Asp Ala Val Ala Glu Leu
1775             1780                 1785

Ile Ala Lys Val Pro Val Glu His Pro Leu Thr Ala Val Val His
1790             1795                 1800

Thr Ala Gly Val Val Ala Asp Ala Thr Leu Thr Ala Leu Asp Ala
1805             1810                 1815

Glu Arg Val Asp Thr Val Leu Arg Ala Lys Val Asp Ala Val Leu
1820             1825                 1830

His Leu His Glu Ala Thr Arg Gly Leu Asp Leu Ala Gly Phe Val
1835             1840                 1845

Leu Phe Ser Ser Ala Ser Gly Ile Phe Gly Ser Pro Gly Gln Gly
1850             1855                 1860

Asn Tyr Ala Ala Ala Asn Ser Phe Ile Asp Ala Phe Ala His His
1865             1870                 1875

Arg Arg Ala Gln Gly Leu Pro Ala Leu Ser Leu Ala Trp Gly Leu
1880             1885                 1890

Trp Ala Arg Thr Ser Gly Met Ala Gly Gln Leu Gly His Asp Asp
1895             1900                 1905

Val Ala Arg Ile Ser Arg Thr Gly Leu Ala Pro Ile Thr Asp Asp
1910             1915                 1920

Gln Gly Met Ala Leu Leu Asp Ala Ala Leu Gly Ala Gly Arg Pro
1925             1930                 1935
```

```
Leu Leu Val Pro Val Arg Leu Asp Arg Ala Ala Leu Arg Ser Gln
    1940                1945                1950

Ala Thr Ala Gly Thr Leu Pro Pro Ile Leu Arg Gly Leu Val Arg
    1955                1960                1965

Ala Thr Val Arg Arg Ala Ala Ser Thr Ala Ala Ala Gln Gly Pro
    1970                1975                1980

Ser Leu Ala Glu Arg Leu Ala Gly Leu Pro Val Thr Glu His Glu
    1985                1990                1995

Arg Ile Val Val Glu Leu Val Arg Ala Asp Leu Ala Ala Val Leu
    2000                2005                2010

Gly His Ser Ser Ala Gly Ile Asp Pro Gly Arg Ala Phe Gln
    2015                2020                2025

Asp Met Gly Ile Asp Ser Leu Thr Ala Val Glu Leu Arg Asn Arg
    2030                2035                2040

Leu Asn Gly Ala Thr Gly Leu Arg Leu Ala Ala Ser Leu Val Phe
    2045                2050                2055

Asp Tyr Pro Thr Pro Asn Ala Leu Ala Thr His Ile Leu Asp Glu
    2060                2065                2070

Leu Ala Leu Asp Thr Ala Gly Ala Gly Ala Ala Gly Glu Pro Asp
    2075                2080                2085

Gly Pro Ala Pro Ala Pro Ala Asp Glu Ala Arg Phe Arg Arg Val
    2090                2095                2100

Ile Asn Ser Ile Pro Leu Asp Arg Ile Arg Arg Ala Gly Leu Leu
    2105                2110                2115

Asp Ala Leu Leu Gly Leu Ala Gly Thr Ser Ala Asp Thr Ala Ala
    2120                2125                2130

Ser Asp Asp Phe Asp Gln Glu Glu Asp Gly Pro Ala Ile Ala Ser
    2135                2140                2145

Met Asp Val Asp Asp Leu Val Arg Ile Ala Leu Gly Glu Ser Asp
    2150                2155                2160

Thr Thr Ala Asp Ile Thr Glu Gly Thr Asp Arg Ser
    2165                2170                2175

<210> SEQ ID NO 9
<211> LENGTH: 2223
<212> TYPE: PRT
<213> ORGANISM: Streptomyces nanchangensis

<400> SEQUENCE: 9

Met Val Ser Glu Glu Lys Leu Val Glu Tyr Leu Arg Arg Val Thr Thr
1               5                   10                  15

Glu Leu His Asp Ala Arg Thr Arg Leu Arg Glu Leu Glu Glu Gly Glu
                20                  25                  30

Gln Glu Pro Val Ala Val Val Gly Met Ala Cys Arg Phe Pro Gly Gly
            35                  40                  45

Val Arg Ser Pro Glu Asp Leu Arg Arg Leu Val Leu Ser Gly Gly Asp
        50                  55                  60

Ala Ile Gly Asp Phe Pro Thr Asp Arg Gly Trp Asp Leu Asp Gly Leu
65                  70                  75                  80

Phe His Pro Asp Pro Ala His Phe Gly Thr Ser Tyr Val Ser Gln Gly
                85                  90                  95

Gly Phe Leu Tyr Asp Val Asp Arg Phe Asp Ala Gly Phe Phe Gly Ile
                100                 105                 110

Ser Pro Arg Glu Ala Leu Ala Met Asp Pro Gln Gln Arg Leu Leu Leu
            115                 120                 125
```

```
Glu Leu Ser Trp Glu Ala Leu Glu Ser Ala Gly Val Pro Gly Ala
    130                 135                 140

Leu Arg Ala Ser Arg Thr Gly Val Tyr Val Gly Val Ser Ser Glu Asp
145                 150                 155                 160

Tyr Ile Ser Gly Leu Pro Gln Ile Pro Glu Gly Phe Glu Gly Tyr Ala
                165                 170                 175

Thr Thr Gly Ser Leu Thr Ser Val Ile Ser Gly Arg Val Ala Tyr Thr
            180                 185                 190

Phe Gly Phe Glu Gly Pro Ala Val Thr Val Asp Thr Ala Cys Ser Ser
        195                 200                 205

Ser Met Val Ala Ile His Leu Ala Gly Gln Ala Leu Arg Gln Gly Glu
    210                 215                 220

Cys Ser Leu Ala Leu Ala Gly Gly Val Thr Val Leu Ser Thr Pro Leu
225                 230                 235                 240

Met Phe Thr Glu Phe Cys Arg Gln Arg Ala Leu Thr Pro Asp Ala Arg
                245                 250                 255

Cys Lys Pro Phe Ala Ala Ala Asp Gly Thr Gly Phe Ser Glu Gly
                260                 265                 270

Ala Gly Leu Leu Leu Leu Glu Arg Leu Ser Asp Ala Arg Arg Asn Gly
            275                 280                 285

His Glu Val Leu Ala Val Leu Arg Gly Ser Ala Ile Asn Gln Asp Gly
    290                 295                 300

Ala Ser Asn Gly Leu Thr Ala Pro Asn Asp Val Ala Gln Glu Ser Val
305                 310                 315                 320

Ile Arg Asp Ala Leu Ala Arg Ala Gly Leu Ser Gly Ala Asp Val Asp
                325                 330                 335

Met Val Glu Ala His Gly Thr Gly Thr Arg Leu Gly Asp Pro Ile Glu
            340                 345                 350

Ala Glu Ala Leu Ile Ala Thr Tyr Gly Ala Asp Arg Pro Ala Asp Arg
        355                 360                 365

Pro Leu Tyr Leu Gly Ser Ile Lys Ser Asn Ile Gly His Thr His Ala
    370                 375                 380

Ala Ala Gly Val Ala Gly Ala Ile Asn Thr Val Met Ala Leu Arg Asp
385                 390                 395                 400

Gly Lys Leu Ala Arg Thr Leu His Ile Asp Glu Pro Thr Arg His Val
                405                 410                 415

Asp Trp Ser Ala Gly Thr Val Arg Leu Leu Thr Asp Pro Tyr Asp Trp
            420                 425                 430

Pro Val Ala Asp Arg Pro Arg Arg Ala Ala Val Ser Ser Phe Gly Val
        435                 440                 445

Ser Gly Thr Asn Ala His Val Ile Leu Glu Gln Ala Pro Asp Ala Gly
    450                 455                 460

Ala Gln Gln Asp Ala Arg Gln Arg Gly Asp Thr Phe His Gly Val
465                 470                 475                 480

Val Pro Trp Pro Val Ser Gly Arg Thr Glu Ala Ala Leu Arg Asp Gln
                485                 490                 495

Ala Ala Arg Leu Gly Ala Phe Leu Thr Ala Asp Gly Ala Thr Ala Asn
            500                 505                 510

Gly Ala Ala Thr Gly Gly Val Ala Asp Val Gly Trp Ser Leu Ala Met
        515                 520                 525

Arg Arg Thr Ala Phe Glu His Arg Ala Val Val Gly Arg Asp Arg
    530                 535                 540
```

```
Ser Asp Leu Leu Ala Ala Leu Glu Gly Leu Ala Ala Asp Glu Pro Gly
545                 550                 555                 560

Pro Ala Val Val Arg Gly Val Ala Ala Asp Val Gly Ala Gly Pro Val
                565                 570                 575

Met Val Phe Pro Gly Gln Gly Ser Gln Trp Leu Gly Met Gly Val Glu
            580                 585                 590

Leu Leu Asp Ser Ser Pro Val Phe Ala Ala Arg Ile Ala Ala Cys Glu
        595                 600                 605

Arg Ala Leu Ala Ala His Val Asp Trp Ser Leu Thr Asp Val Leu Arg
610                 615                 620

Gly Ala Arg Gly Ala Ala Asp Ile Gly Arg Val Asp Val Val Gln Pro
625                 630                 635                 640

Val Leu Trp Ala Val Met Val Ser Leu Ala Ala Val Trp Glu Ala His
                645                 650                 655

Gly Val Arg Pro Ser Ala Val Val Gly His Ser Gln Gly Glu Ile Ala
            660                 665                 670

Ala Ala Cys Val Ala Gly Ala Met Thr Leu Glu Asp Gly Ala Arg Val
        675                 680                 685

Val Ala Leu Arg Ala Arg Ala Leu Arg Ala Leu Ala Gly Tyr Gly Ala
690                 695                 700

Met Ala Ser Leu Gly Cys Gly Val Glu Glu Thr Glu Arg Leu Thr Ala
705                 710                 715                 720

Val His Ala Pro Asp Val Ala Val Ala Ala Val Asn Gly Pro Ser Ser
                725                 730                 735

Thr Val Val Ser Gly Pro Ser Glu Gln Val Glu Lys Leu Val Ala Ala
            740                 745                 750

Val Arg Ala Asp Gly Leu Arg Ala Arg Ala Ile Asp Val Asp Tyr Ala
        755                 760                 765

Ser His Gly Pro Gln Val Asp Arg Ile Ala Asp Glu Leu Ala Asp Val
770                 775                 780

Leu Ala Gly Val Ser Gly Ala Ala Thr Asp Thr Ala Phe Tyr Ser Thr
785                 790                 795                 800

Val Thr Gly Ala Arg Met Asp Ala Ser Gly Leu Asp Ala Gly Tyr Trp
                805                 810                 815

Phe Thr Asn Leu Arg Gln Pro Val Arg Phe Ala Glu Ala Val Gln Ala
            820                 825                 830

Leu Leu Asp Ala Asp Tyr Arg Val Phe Ile Glu Val Ser Ala His Pro
        835                 840                 845

Val Leu Leu Leu Gly Leu Gln Glu Cys Phe Glu Ala Ala Gly Arg Pro
850                 855                 860

Ala Val Ala Ile Gly Thr Leu Arg Arg Asp Glu Gly Gly Pro Glu Arg
865                 870                 875                 880

Leu Cys Arg Ala Leu Ala Glu Ala His Val Ala Gly Val Ala Val Asp
                885                 890                 895

Trp Ala Ser Trp Tyr Ala Asp Gly Pro Ala Pro Ala Ala Val Pro Leu
            900                 905                 910

Pro Ala Tyr Ala Phe Gln Arg Glu Arg Tyr Trp Leu Pro Ala Gly Ala
        915                 920                 925

Gly Ser Gly Pro Gly Asp Val Ala Gly Ala Gly Leu Thr Ala Val Gly
930                 935                 940

His Ala Leu Leu Pro Val Ser Val Arg Leu Ala Asp Gly Ser Leu Val
945                 950                 955                 960
```

```
Leu Thr Gly Arg Leu Pro Glu Ala Ala Arg Ala Gly Trp Leu Ala Glu
            965                 970                 975

His Leu Val Ala Asp Leu Pro Leu Pro Gly Thr Val Leu Val Glu
        980                 985                 990

Trp Val Leu Arg Ala Ala Asp Glu Ala Gly Cys Gly Gly Val Glu Glu
        995                 1000                1005

Leu Ala Leu Gln Val Pro Val Ala Leu Pro Val Ser Gly Gly Leu
        1010                1015                1020

Val Ile Gln Val Val Val Asp Ala Ala Glu Gly Asp Gly Arg Arg
        1025                1030                1035

Pro Val Arg Val His Ser Arg Pro Glu Glu Asp Ser Gly Ala Pro
        1040                1045                1050

Asp Ala Trp Val Cys His Val Ser Gly Thr Leu Leu Pro Gly Val
        1055                1060                1065

Ala Gly Pro Val Pro Pro Ser Gly Pro Gly Ala Trp Pro Pro
        1070                1075                1080

Pro Gly Ala Arg Pro Ala Ala Ile Asp Gly Phe Tyr Glu Arg Ala
        1085                1090                1095

Glu Ala Ala Gly Tyr Gly Tyr Gly Ala Phe Phe Arg Gly Leu Thr
        1100                1105                1110

Asn Val Trp His Asp Gly Glu Asp Thr Leu Ala Glu Val Val Leu
        1115                1120                1125

Pro Lys Glu Ala Ala Glu Gln Ala Gly Gly Phe Gly Ile His Pro
        1130                1135                1140

Ala Leu Leu Asp Ala Ala Met Gln Pro Val Leu Leu Ala Gly Gln
        1145                1150                1155

Leu Arg Gln Cys Ala Ala Ala Ala Gly Ala Asp Thr Ala Ser Gly
        1160                1165                1170

Thr Val Leu Leu Pro Phe Thr Trp Ser Gly Val Arg Leu Trp Ala
        1175                1180                1185

Gly Gly Ala Thr Arg Leu Arg Val Arg Leu Ser Pro Arg Pro Glu
        1190                1195                1200

Gly Leu Arg Val Leu Leu Ala Asp Ala Thr Gly Ala Pro Val Leu
        1205                1210                1215

Thr Ala Asp Ala Val Ala Leu Arg Glu Thr Gly Val Gln Gln Leu
        1220                1225                1230

Arg Ala Ser Ser Arg Val Arg Gly Ser His Gly Leu Phe Ala Val
        1235                1240                1245

Glu Trp Val Pro Pro Leu Ser Ala Thr Ala Gly Gly Thr Ala Pro
        1250                1255                1260

Ala Thr Leu Ala Val Leu Gly Asp Asp Ala Pro Asp Leu Ala Asp
        1265                1270                1275

Ala Asp Arg Tyr Pro Asp Leu Asp Ala Leu Phe Arg Ala Val Ala
        1280                1285                1290

Asp Gly Ala Pro Ala Pro Asp Val Val Ile Ala Ser Val Arg Thr
        1295                1300                1305

Gly Asn Asp Pro Ala Gly Ser Asp Thr Gly Leu Ala Thr Ala Arg
        1310                1315                1320

Arg Thr Leu Thr Leu Ala Gln Glu Trp Leu Ala Gly Ser Gly Ala
        1325                1330                1335

Asp Gly Ala Arg Leu Ala Val Val Thr Arg Ser Ala Ile Arg Thr
        1340                1345                1350
```

```
Gly Asp Asp Gly Gln Glu Arg Val Val Pro Ser Ala Ala Ala Val
1355                1360                1365

Trp Gly Leu Met Arg Ser Ala Gln Thr Glu His Pro Gly Arg Phe
1370                1375                1380

Val Leu Ile Asp Glu Asp Thr Asp Ser Thr Glu Asn Ile Leu Glu
1385                1390                1395

Ala Val Arg Thr Asp Glu Pro Gln Leu Ala Leu Arg Gly Gly Arg
1400                1405                1410

Ala Leu Val Pro Arg Met Ala Arg Val Asp Ala Glu Pro Glu Leu
1415                1420                1425

Thr Ala Pro Ser Gly Glu Arg Ala Trp His Val Ala Ala Gly Lys
1430                1435                1440

Thr Gly Pro Asp Asp Leu Thr Ala Val Pro Ser Pro Arg Ala Ser
1445                1450                1455

Ala Pro Leu Ala Pro Gly Gln Val Arg Ile Ala Val Arg Ala Ala
1460                1465                1470

Gly Leu Asn Phe Arg Asp Ala Leu Ile Ala Leu Asp Met Tyr Pro
1475                1480                1485

Asp Ala Ser Ala Ser Ile Gly Ser Glu Gly Ala Gly Val Val Leu
1490                1495                1500

Glu Val Ser Glu Gly Val Ala Gly Val Ala Val Gly Asp Arg Val
1505                1510                1515

Met Gly Leu Phe Asn Asp Ala Phe Gly Pro Val Ala Val Ala Asp
1520                1525                1530

Ala Arg Met Val Ala Pro Val Pro Asp Gly Trp Ser Phe Arg Glu
1535                1540                1545

Ala Ala Ala Ala Pro Val Ala Phe Leu Thr Ala Trp Tyr Gly Leu
1550                1555                1560

Val Asp Leu Gly Gly Leu Ser Ser Gly Glu Thr Val Val Ile His
1565                1570                1575

Gly Ala Ala Gly Gly Val Gly Met Ala Ala Val Gln Val Ala Arg
1580                1585                1590

His Leu Gly Ala Glu Val Phe Ala Thr Ala Ser Pro Ala Lys His
1595                1600                1605

Pro Val Leu Glu Gly Met Gly Val Asp Ala Ala His Arg Ala Ser
1610                1615                1620

Ser Arg Asp Leu Gly Phe Glu Ala Ala Phe Ser Ser Ala Thr Gly
1625                1630                1635

Gly Arg Gly Val Asp Val Val Leu Asn Ser Leu Ala Gly Glu Phe
1640                1645                1650

Thr Asp Ala Ser Leu Arg Leu Leu Ala Pro Gly Gly Arg Leu Ile
1655                1660                1665

Glu Met Gly Lys Thr Asp Val Arg Asp Pro Asp Gln Val Ala Arg
1670                1675                1680

Glu His Ser Val Ala Tyr Arg Ala Phe Asp Leu Ile Ala Asp Ala
1685                1690                1695

Gly Pro Glu Arg Ile Gly Gln Leu Leu Ala Ala Leu Gly Glu Arg
1700                1705                1710

Phe Ala Asp Gly Ala Phe Thr Pro Leu Pro Val Thr Gly Trp Arg
1715                1720                1725

Leu Gly Gln Ala Arg Gln Ala Leu Arg Gln Leu Ser Gln Ala Arg
1730                1735                1740
```

His Thr Gly Lys Leu Val Leu Asp Val Asp Pro Ala Pro Asp Pro
1745                1750                1755

Asp Gly Thr Val Leu Ile Thr Gly Gly Thr Gly Thr Leu Gly Gly
1760                1765                1770

Leu Ile Ala Glu His Leu Val Arg Ser Arg Gly Val Arg His Leu
1775                1780                1785

Leu Leu Leu Ser Arg Arg Gly Pro Asp Ala Pro Gly Ala Glu Glu
1790                1795                1800

Leu Thr Ala Arg Leu Thr Glu Leu Gly Ala Arg Val Arg Val Ala
1805                1810                1815

Ala Val Asp Val Gly Asp Ala Thr Ala Leu Gly Glu Ala Val Ala
1820                1825                1830

Gly Val Asp Pro Ala His Pro Leu Thr Gly Val Val His Ala Ala
1835                1840                1845

Gly Val Val Ala Asp Ala Met Leu Pro Ser Gln Asp Asp Glu Arg
1850                1855                1860

Leu Val Ala Ala Trp Ser Ala Lys Ala Ala Ala Ala Arg Leu
1865                1870                1875

His Asp Ala Thr Ala Gly Leu Pro Leu Gly Met Phe Val Leu Phe
1880                1885                1890

Ser Ser Phe Ala Ser Thr Leu Gly Thr Ala Gly Gln Ala Asn Tyr
1895                1900                1905

Ala Ala Ala Asn Ala Tyr Cys Asp Ala Leu Val Glu Arg Arg His
1910                1915                1920

Ala Glu Gly Leu Pro Gly Val Ser Val Ser Trp Gly Leu Trp Ser
1925                1930                1935

Ala Ala Ser Gly Leu Thr Gly Gly Leu Thr Glu Ala Asp Val Ala
1940                1945                1950

Arg Ile Ala Arg Gln Gly Ile Val Pro Asn Ser Thr Glu Gln Gly
1955                1960                1965

Tyr Asp Leu Phe Asp Ala Ala Leu Gly His Gly Arg Pro Ala Leu
1970                1975                1980

Leu Ala Leu Asn Leu Asp Thr Arg Ala Leu Ala Ala Gln Pro Val
1985                1990                1995

Ala Ala Leu Pro Ala Pro Leu Arg Ala Leu Ala Ala Asp Ala Gln
2000                2005                2010

Ala Ala Gly Ala Arg Ser Gly Gly Ala Ala Ala Arg Pro Thr Ala
2015                2020                2025

Ala Ala Ala Glu Glu Pro Ala Asp Trp Ala Ala Arg Leu Arg Ala
2030                2035                2040

Leu Ala Pro Ala Glu Gln Arg Arg Leu Leu Thr Asp Leu Val Arg
2045                2050                2055

Arg His Ala Ala Thr Val Leu Gly His Ala Asp Pro Glu Ala Val
2060                2065                2070

Pro Ala Asp Ala Ala Phe Lys Glu Leu Gly Phe Asp Ser Leu Thr
2075                2080                2085

Ala Val Glu Leu Arg Asn Arg Val Thr Ala Ala Thr Gly Leu Arg
2090                2095                2100

Leu Pro Ala Thr Val Ile Phe Asp Tyr Pro Glu Pro Gly Ala Leu
2105                2110                2115

Ala Glu Arg Leu Arg Thr Glu Leu Ala Pro Glu Glu Gly Ala Ser
2120                2125                2130

```
Ala Thr Ala Pro Asp Leu Tyr Ala Pro Val Leu Ser Arg Leu Thr
    2135                2140                2145

Gly Leu Glu Glu Thr Leu Ala Ala Leu Ala Ser Ser Gly Val Asn
    2150                2155                2160

Gly Gly Val Asn Gly Gly Val Ala Asp Pro Gly Ala Val Thr Ala
    2165                2170                2175

Arg Leu Glu Ser Leu Leu Ala Asp Trp Lys Ala Ala His Ala Pro
    2180                2185                2190

Ser Arg Asn Gly Gly Thr Ala Ala Glu Arg Leu Glu Ala Ala Thr
    2195                2200                2205

Thr Asp Gln Val Leu Asp Phe Ile Asp Lys Glu Leu Gly Val Gln
    2210                2215                2220

<210> SEQ ID NO 10
<211> LENGTH: 2152
<212> TYPE: PRT
<213> ORGANISM: Saccharopolyspora spinosa

<400> SEQUENCE: 10

Met Thr Val Thr Thr Ser Tyr Glu Glu Val Val Glu Ala Leu Arg Ala
1               5                   10                  15

Ser Leu Lys Glu Asn Glu Arg Leu Arg Arg Gly Arg Asp Arg Phe Ser
                20                  25                  30

Ala Glu Lys Asp Asp Pro Ile Ala Ile Val Ala Met Ser Cys Arg Tyr
            35                  40                  45

Pro Gly Gln Val Ser Ser Pro Glu Asp Leu Trp Gln Leu Ala Ala Gly
        50                  55                  60

Gly Val Asp Ala Ile Ser Glu Val Pro Gly Asp Arg Gly Trp Asp Leu
65                  70                  75                  80

Asp Gly Val Phe Val Pro Asp Ser Asp Arg Pro Gly Thr Ser Tyr Ala
                85                  90                  95

Cys Ala Gly Gly Phe Leu Gln Gly Val Ser Glu Phe Asp Ala Gly Phe
            100                 105                 110

Phe Gly Ile Ser Pro Arg Glu Ala Leu Ala Met Asp Pro Gln Gln Arg
        115                 120                 125

Leu Leu Leu Glu Val Ala Trp Glu Val Phe Glu Arg Ala Gly Leu Glu
    130                 135                 140

Gln Arg Ser Thr Arg Gly Ser Arg Val Gly Val Phe Val Gly Thr Asn
145                 150                 155                 160

Gly Gln Asp Tyr Ala Ser Trp Leu Arg Thr Pro Pro Ala Val Ala
                165                 170                 175

Gly His Val Leu Thr Gly Gly Ala Ala Val Leu Ser Gly Arg Val
            180                 185                 190

Ala Tyr Ser Phe Gly Phe Glu Gly Pro Ala Val Thr Val Asp Thr Ala
        195                 200                 205

Cys Ser Ser Ser Leu Val Ala Leu His Leu Ala Gly Gln Ala Leu Arg
    210                 215                 220

Ala Gly Glu Cys Asp Leu Ala Leu Ala Gly Gly Val Thr Val Met Ser
225                 230                 235                 240

Thr Pro Lys Val Phe Leu Glu Phe Ser Arg Gln Arg Gly Leu Ala Pro
                245                 250                 255

Asp Gly Arg Cys Lys Ser Phe Ala Ala Gly Ala Asp Gly Thr Gly Trp
            260                 265                 270

Gly Glu Gly Ala Gly Leu Leu Leu Leu Glu Arg Leu Ser Asp Ala Arg
        275                 280                 285
```

-continued

Arg Asn Gly His Glu Val Leu Ala Val Val Arg Gly Ser Ala Val Asn
290                 295                 300

Gln Asp Gly Ala Ser Asn Gly Leu Thr Ala Pro Asn Gly Ser Ser Gln
305                 310                 315                 320

Gln Arg Val Ile Thr Gln Ala Leu Ala Ser Ala Gly Leu Ser Val Ser
            325                 330                 335

Asp Val Asp Ala Val Glu Ala His Gly Thr Gly Thr Arg Leu Gly Asp
            340                 345                 350

Pro Ile Glu Ala Gln Ala Leu Ile Ala Thr Tyr Gly Arg Asp Arg Asp
            355                 360                 365

Pro Gly Arg Pro Leu Trp Leu Gly Ser Val Lys Ser Asn Ile Gly His
370                 375                 380

Thr Gln Ala Ala Ala Gly Val Ala Gly Val Ile Lys Met Val Met Ala
385                 390                 395                 400

Met Arg His Gly Gln Leu Pro Arg Thr Leu His Val Glu Ser Pro Ser
                405                 410                 415

Pro Glu Val Asp Trp Ser Ala Gly Thr Val Gln Leu Leu Thr Glu Asn
            420                 425                 430

Thr Pro Trp Pro Arg Ser Gly Arg Val Arg Arg Val Gly Val Ser Ser
            435                 440                 445

Phe Gly Ile Ser Gly Thr Asn Ala His Val Ile Leu Glu Gln Pro Pro
450                 455                 460

Gly Val Pro Ser Gln Ser Ala Gly Pro Gly Ser Gly Val Val Asp
465                 470                 475                 480

Val Pro Val Val Pro Trp Met Val Ser Gly Lys Thr Pro Glu Ala Leu
            485                 490                 495

Ser Ala Gln Ala Thr Ala Leu Met Thr Tyr Leu Asp Glu Arg Pro Asp
            500                 505                 510

Val Ser Ser Leu Asp Val Gly Tyr Ser Leu Ala Leu Thr Arg Ser Ala
            515                 520                 525

Leu Asp Glu Arg Ala Val Val Leu Gly Ser Asp Arg Glu Thr Leu Leu
530                 535                 540

Cys Gly Val Lys Ala Leu Ser Ala Gly His Glu Ala Ser Gly Leu Val
545                 550                 555                 560

Thr Gly Ser Val Gly Ala Gly Arg Ile Gly Phe Val Phe Ser Gly
            565                 570                 575

Gln Gly Gly Gln Trp Leu Gly Met Gly Arg Gly Leu Tyr Arg Ala Phe
            580                 585                 590

Pro Val Phe Ala Ala Ala Phe Asp Glu Ala Cys Ala Glu Leu Asp Ala
            595                 600                 605

His Leu Gly Gln Glu Ile Gly Val Arg Glu Val Val Ser Gly Ser Asp
            610                 615                 620

Ala Gln Leu Leu Asp Arg Thr Leu Trp Ala Gln Ser Gly Leu Phe Ala
625                 630                 635                 640

Leu Gln Val Gly Leu Leu Lys Leu Leu Asp Ser Trp Gly Val Arg Pro
            645                 650                 655

Ser Val Val Leu Gly His Ser Val Gly Glu Leu Ala Ala Ala Phe Ala
            660                 665                 670

Ala Gly Val Val Ser Leu Ser Gly Ala Ala Arg Leu Val Ala Gly Arg
            675                 680                 685

Ala Arg Leu Met Gln Ala Leu Pro Ser Gly Gly Met Leu Ala Val
690                 695                 700

```
Pro Ala Gly Glu Glu Leu Leu Trp Ser Leu Leu Ala Asp Gln Gly Asp
705                 710                 715                 720

Arg Val Gly Ile Ala Ala Val Asn Ala Ala Gly Ser Val Val Leu Ser
            725                 730                 735

Gly Asp Arg Asp Val Leu Asp Asp Leu Ala Gly Arg Leu Asp Gly Gln
        740                 745                 750

Gly Ile Arg Ser Arg Trp Leu Arg Val Ser His Ala Phe His Ser Tyr
    755                 760                 765

Arg Met Asp Pro Met Leu Ala Glu Phe Ala Glu Leu Ala Arg Thr Val
770                 775                 780

Asp Tyr Arg Arg Cys Glu Val Pro Ile Val Ser Thr Leu Thr Gly Asp
785                 790                 795                 800

Leu Asp Asp Ala Gly Arg Met Ser Gly Pro Asp Tyr Trp Val Arg Gln
                805                 810                 815

Val Arg Glu Pro Val Arg Phe Ala Asp Gly Val Gln Ala Leu Val Glu
            820                 825                 830

His Asp Val Ala Thr Val Val Glu Leu Gly Pro Asp Gly Ala Leu Ser
        835                 840                 845

Ala Leu Ile Gln Glu Cys Val Ala Ala Ser Asp His Ala Gly Arg Leu
    850                 855                 860

Ser Ala Val Pro Ala Met Arg Arg Asn Gln Asp Glu Ala Gln Lys Val
865                 870                 875                 880

Met Thr Ala Leu Ala His Val His Val Arg Gly Gly Ala Val Asp Trp
                885                 890                 895

Arg Ser Phe Phe Ala Gly Thr Gly Ala Lys Gln Ile Glu Leu Pro Thr
            900                 905                 910

Tyr Ala Phe Gln Arg Gln Arg Tyr Trp Leu Val Pro Ser Asp Ser Gly
        915                 920                 925

Asp Val Thr Gly Ala Gly Leu Ala Gly Ala Glu His Pro Leu Leu Gly
    930                 935                 940

Ala Val Val Pro Val Ala Gly Gly Asp Glu Val Leu Leu Thr Gly Arg
945                 950                 955                 960

Ile Ser Val Arg Thr His Pro Trp Leu Ala Glu His Arg Val Leu Gly
                965                 970                 975

Glu Val Ile Val Ala Gly Thr Ala Leu Leu Glu Ile Ala Leu His Ala
            980                 985                 990

Gly Glu Arg Leu Gly Cys Glu Arg Val Glu Glu Leu Thr Leu Glu Ala
        995                 1000                1005

Pro Leu Val Leu Pro Glu Arg Gly Ala Ile Gln Val Gln Leu Arg
    1010                1015                1020

Val Gly Ala Pro Glu Asn Ser Gly Arg Arg Pro Met Ala Leu Tyr
    1025                1030                1035

Ser Arg Pro Glu Gly Ala Ala Glu His Asp Trp Thr Arg His Ala
    1040                1045                1050

Thr Gly Arg Leu Ala Pro Gly Arg Gly Glu Ala Ala Gly Asp Leu
    1055                1060                1065

Ala Asp Trp Pro Ala Pro Gly Ala Leu Pro Val Asp Leu Asp Glu
    1070                1075                1080

Phe Tyr Arg Asp Leu Ala Glu Leu Gly Leu Glu Tyr Gly Pro Ile
    1085                1090                1095

Phe Gln Gly Leu Lys Ala Ala Trp Arg Gln Gly Asp Glu Val Tyr
    1100                1105                1110
```

| | | | | | | | | | | | |
|---|---|---|---|---|---|---|---|---|---|---|---|
| Ala | Glu | Ala | Ala | Leu | Pro | Gly | Thr | Glu | Asp | Ser | Gly | Phe | Gly | Val |
| | 1115 | | | | 1120 | | | | 1125 | | |
| His | Pro | Ala | Leu | Leu | Asp | Ala | Ala | Leu | His | Ala | Thr | Ala | Val | Arg |
| | 1130 | | | | 1135 | | | | 1140 | | |
| Asp | Met | Asp | Asp | Ala | Arg | Leu | Pro | Phe | Gln | Trp | Glu | Gly | Val | Ser |
| | 1145 | | | | 1150 | | | | 1155 | | |
| Leu | His | Ala | Lys | Ala | Ala | Pro | Ala | Leu | Arg | Val | Arg | Val | Val | Pro |
| | 1160 | | | | 1165 | | | | 1170 | | |
| Ala | Gly | Asp | Asp | Ala | Lys | Ser | Leu | Leu | Val | Cys | Asp | Gly | Thr | Gly |
| | 1175 | | | | 1180 | | | | 1185 | | |
| Arg | Pro | Val | Ile | Ser | Val | Asp | Arg | Leu | Val | Leu | Arg | Ser | Ala | Ala |
| | 1190 | | | | 1195 | | | | 1200 | | |
| Ala | Arg | Arg | Thr | Gly | Ala | Arg | Arg | Gln | Ala | His | Gln | Ala | Arg | Leu |
| | 1205 | | | | 1210 | | | | 1215 | | |
| Tyr | Arg | Leu | Ser | Trp | Pro | Thr | Val | Gln | Leu | Pro | Thr | Ser | Ala | Gln |
| | 1220 | | | | 1225 | | | | 1230 | | |
| Pro | Pro | Ser | Cys | Val | Leu | Leu | Gly | Thr | Ser | Glu | Val | Ser | Ala | Asp |
| | 1235 | | | | 1240 | | | | 1245 | | |
| Ile | Gln | Val | Tyr | Pro | Asp | Leu | Arg | Ser | Leu | Thr | Ala | Ala | Leu | Asp |
| | 1250 | | | | 1255 | | | | 1260 | | |
| Ala | Gly | Ala | Glu | Pro | Pro | Gly | Val | Val | Ile | Ala | Pro | Thr | Pro | Pro |
| | 1265 | | | | 1270 | | | | 1275 | | |
| Gly | Gly | Gly | Arg | Thr | Ala | Asp | Val | Arg | Glu | Thr | Thr | Arg | His | Ala |
| | 1280 | | | | 1285 | | | | 1290 | | |
| Leu | Asp | Leu | Val | Gln | Gly | Trp | Leu | Ser | Asp | Gln | Arg | Leu | Asn | Glu |
| | 1295 | | | | 1300 | | | | 1305 | | |
| Ser | Arg | Leu | Leu | Leu | Val | Thr | Gln | Gly | Ala | Val | Ala | Val | Glu | Pro |
| | 1310 | | | | 1315 | | | | 1320 | | |
| Gly | Glu | Pro | Val | Thr | Asp | Leu | Ala | Gln | Ala | Ala | Leu | Trp | Gly | Leu |
| | 1325 | | | | 1330 | | | | 1335 | | |
| Leu | Arg | Ser | Thr | Gln | Thr | Glu | His | Pro | Asp | Arg | Phe | Val | Leu | Val |
| | 1340 | | | | 1345 | | | | 1350 | | |
| Asp | Val | Pro | Glu | Pro | Ala | Gln | Leu | Leu | Pro | Ala | Leu | Pro | Gly | Val |
| | 1355 | | | | 1360 | | | | 1365 | | |
| Leu | Ala | Cys | Gly | Glu | Pro | Gln | Leu | Ala | Leu | Arg | Arg | Gly | Gly | Ala |
| | 1370 | | | | 1375 | | | | 1380 | | |
| His | Ala | Pro | Arg | Leu | Ala | Gly | Leu | Gly | Ser | Asp | Asp | Val | Leu | Pro |
| | 1385 | | | | 1390 | | | | 1395 | | |
| Val | Pro | Asp | Gly | Thr | Gly | Trp | Arg | Leu | Glu | Ala | Thr | Arg | Pro | Gly |
| | 1400 | | | | 1405 | | | | 1410 | | |
| Ser | Leu | Asp | Gly | Leu | Ala | Leu | Val | Asp | Glu | Pro | Thr | Ala | Thr | Ala |
| | 1415 | | | | 1420 | | | | 1425 | | |
| Pro | Leu | Gly | Asp | Gly | Glu | Val | Arg | Ile | Ala | Met | Arg | Ala | Ala | Gly |
| | 1430 | | | | 1435 | | | | 1440 | | |
| Val | Asn | Phe | Arg | Asp | Ala | Leu | Ile | Ala | Leu | Gly | Met | Tyr | Pro | Gly |
| | 1445 | | | | 1450 | | | | 1455 | | |
| Val | Ala | Ser | Leu | Gly | Ser | Glu | Gly | Ala | Gly | Val | Val | Val | Glu | Thr |
| | 1460 | | | | 1465 | | | | 1470 | | |
| Gly | Pro | Gly | Val | Thr | Gly | Leu | Ala | Pro | Gly | Asp | Arg | Val | Met | Gly |
| | 1475 | | | | 1480 | | | | 1485 | | |
| Met | Ile | Pro | Lys | Ala | Phe | Gly | Pro | Leu | Ala | Val | Ala | Asp | His | Arg |
| | 1490 | | | | 1495 | | | | 1500 | | |

```
Met Val Thr Arg Ile Pro Ala Gly Trp Ser Phe Ala Arg Ala Ala
1505                1510                1515

Ser Val Pro Ile Val Phe Leu Thr Ala Tyr Tyr Ala Leu Val Asp
1520                1525                1530

Leu Ala Gly Leu Arg Pro Gly Glu Ser Leu Leu Val His Ser Ala
1535                1540                1545

Ala Gly Gly Val Gly Met Ala Ala Ile Gln Leu Ala Arg His Leu
1550                1555                1560

Gly Ala Glu Val Tyr Ala Thr Ala Ser Glu Asp Lys Trp Gln Ala
1565                1570                1575

Val Glu Leu Ser Arg Glu His Leu Ala Ser Ser Arg Thr Cys Asp
1580                1585                1590

Phe Glu Gln Gln Phe Leu Gly Ala Thr Gly Gly Arg Gly Val Asp
1595                1600                1605

Val Val Leu Asn Ser Leu Ala Gly Glu Phe Ala Asp Ala Ser Leu
1610                1615                1620

Arg Met Leu Pro Arg Gly Gly Arg Phe Leu Glu Leu Gly Lys Thr
1625                1630                1635

Asp Val Arg Asp Pro Val Glu Val Ala Asp Ala His Pro Gly Val
1640                1645                1650

Ser Tyr Gln Ala Phe Asp Thr Val Glu Ala Gly Pro Gln Arg Ile
1655                1660                1665

Gly Glu Met Leu His Glu Leu Val Glu Leu Phe Glu Gly Arg Val
1670                1675                1680

Leu Glu Pro Leu Pro Val Thr Ala Trp Asp Val Arg Gln Ala Pro
1685                1690                1695

Glu Ala Leu Arg His Leu Ser Gln Ala Arg His Val Gly Lys Leu
1700                1705                1710

Val Leu Thr Met Pro Pro Val Trp Asp Ala Ala Gly Thr Val Leu
1715                1720                1725

Val Thr Gly Gly Thr Gly Ala Leu Gly Ala Glu Val Ala Arg His
1730                1735                1740

Leu Val Ile Glu Arg Gly Val Arg Asn Leu Val Leu Val Ser Arg
1745                1750                1755

Arg Gly Pro Ala Ala Ser Gly Ala Ala Glu Leu Val Ala Gln Leu
1760                1765                1770

Thr Ala Tyr Gly Ala Glu Val Ser Leu Gln Ala Cys Asp Val Ala
1775                1780                1785

Asp Arg Glu Thr Leu Ala Lys Val Leu Ala Ser Ile Pro Asp Glu
1790                1795                1800

His Pro Leu Thr Ala Val Val His Ala Ala Gly Val Leu Asp Asp
1805                1810                1815

Gly Val Ser Glu Ser Leu Thr Val Glu Arg Leu Asp Gln Val Leu
1820                1825                1830

Arg Pro Lys Val Asp Gly Ala Arg Asn Leu Leu Glu Leu Ile Asp
1835                1840                1845

Pro Asp Val Ala Leu Val Leu Phe Ser Ser Val Ser Gly Val Leu
1850                1855                1860

Gly Ser Gly Gly Gln Gly Asn Tyr Ala Ala Ala Asn Ser Phe Leu
1865                1870                1875

Asp Ala Leu Ala Gln Gln Arg Gln Ser Arg Gly Leu Pro Thr Arg
1880                1885                1890
```

| | | | | | | | | | | | |
|---|---|---|---|---|---|---|---|---|---|---|---|
|Ser|Leu 1895|Ala|Trp|Gly|Pro 1900|Trp|Ala|Glu|His 1905|Gly|Met|Ala|Ser|Thr|
|Leu|Arg 1910|Glu|Ala|Glu|Gln 1915|Asp|Arg|Leu|Ala 1920|Arg|Ser|Gly|Leu|Leu|
|Pro|Ile 1925|Ser|Thr|Glu|Glu 1930|Gly|Leu|Ser|Gln 1935|Phe|Asp|Ala|Ala|Cys|
|Gly|Gly 1940|Ala|His|Thr|Val 1945|Val|Ala|Pro|Val 1950|Arg|Phe|Ser|Arg|Leu|
|Ser|Asp 1955|Gly|Asn|Ala|Ile 1960|Lys|Phe|Ser|Val 1965|Leu|Gln|Gly|Leu|Val|
|Gly|Pro 1970|His|Arg|Val|Asn 1975|Lys|Ala|Ala|Thr 1980|Ala|Asp|Asp|Ala|Glu|
|Ser|Leu 1985|Arg|Lys|Arg|Leu 1990|Gly|Arg|Leu|Pro 1995|Asp|Ala|Glu|Gln|His|
|Arg|Ile 2000|Leu|Leu|Asp|Leu 2005|Val|Arg|Met|His 2010|Val|Ala|Ala|Val|Leu|
|Gly|Phe 2015|Ala|Gly|Ser|Gln 2020|Glu|Ile|Thr|Ala 2025|Asp|Gly|Thr|Phe|Lys|
|Val|Leu 2030|Gly|Phe|Asp|Ser 2035|Leu|Thr|Val|Val 2040|Glu|Leu|Arg|Asn|Arg|
|Ile|Asn 2045|Gly|Ala|Thr|Gly 2050|Leu|Arg|Leu|Pro 2055|Ala|Thr|Leu|Val|Phe|
|Asn|Tyr 2060|Pro|Thr|Pro|Asp 2065|Ala|Leu|Ala|Ala 2070|His|Leu|Val|Thr|Ala|
|Leu|Ser 2075|Ala|Asp|Arg|Leu 2080|Ala|Gly|Thr|Phe 2085|Glu|Glu|Leu|Asp|Arg|
|Trp|Ala 2090|Ala|Asn|Leu|Pro 2095|Thr|Leu|Ala|Arg 2100|Asp|Glu|Ala|Thr|Arg|
|Ala|Gln 2105|Ile|Thr|Thr|Arg 2110|Leu|Gln|Ala|Ile 2115|Leu|Gln|Ser|Leu|Ala|
|Asp|Val 2120|Ser|Gly|Gly|Thr 2125|Gly|Gly|Gly|Ser 2130|Val|Pro|Asp|Arg|Leu|
|Arg|Ser 2135|Ala|Thr|Asp|Asp 2140|Glu|Leu|Phe|Gln 2145|Leu|Leu|Asp|Asn|Asp|
|Leu|Glu 2150|Leu|Pro| | | | | | | | | | | |

PRODUCING ADIPIC ACID AND RELATED COMPOUNDS USING HYBRID POLYKETIDE SYNTHASES

RELATED PATENT APPLICATIONS

The application claims priority as a continuation application to PCT International Patent Application No. PCT/US 16/41795, filed Jul. 11, 2016, which claims priority to U.S. Provisional Patent Application Ser. No. 62/191,283, filed Jul. 10, 2015; both of which are incorporated herein by reference.

STATEMENT OF GOVERNMENTAL SUPPORT

This invention was made with government support under Contract No. DE-AC02-05CH11231 awarded by the U.S. Department of Energy, and Grant Nos. EEC 0540879, DGE 1106400, and MCB 1341894 awarded by the National Science Foundation. The government has certain rights in the invention.

FIELD OF THE INVENTION

This invention relates generally to production of adipic acid and related compounds using polyketide synthases.

BACKGROUND OF THE INVENTION

Dicarboxylic acids (diacids) are important compounds that are used in the manufacture of commercial polymers (e.g. polyesters, polyurethanes). The diacid adipic acid [1] is used mainly as a monomer in the production of 6,6-nylon, a polyamide generated through the reaction of [1] with hexane-1,6-diamine. Polyesters (for use in fabrics and plastics of many compositions) are formed through the polymerization of terephthalic acid [3] and a dialcohol (diol) such as ethylene glycol (to make polyethylene terephthalate), propane diol (poly(1,3-propanediol terephthalate)) or butanediol (poly(1,4-butanediolphthalate). Adipic acid is also used in the synthesis of various polyesters. Currently adipic acid is synthesized via oxidation of cyclohexane and similar petrochemicals using traditional chemical synthesis.

The large scale worldwide use of nylons and polyesters requires the production of millions of metric tons of [1] and [3] annually. These diacids are themselves synthesized from starting materials extracted from petroleum. One means of reducing the large dependence on oil for the commercial production of polymers is to generate the diacids by a fermentation process involving the use of polyketide synthases.

The use of hybrid polyketide synthases to produce diacids with a carbon backbone with an odd number of carbon atoms is disclosed in International Patent Application No. PCT/US2009/038831, filed Mar. 30, 2009, which published as PCT publication no. WO 2009/121066 on Oct. 1, 2009. The use of hybrid polyketide synthases to produce diacids is disclosed in U.S. Patent Application Pub. No. 2013/0280766, now issued as U.S. Pat. No. 9,334,514.

The polyketides are one of the most diverse and chemically complicated classes of molecules known, its members frequently weighing in excess of 500 daltons and harboring numerous stereocenters. Partly owing to their antibacterial, immunosuppressive, and anti-cancer activities, much effort has been devoted to deciphering the mechanism by which polyketide synthases (PKSs) synthesize their products. PKSs perform Claisen condensation reactions between a loaded acyl-ACP intermediate and an α-substituted (H, $CH_3$, $C_2H_5$, etc.) malonyl-CoA extender unit analogous to fatty acid biosynthesis. This is then followed by varying degrees of β-reduction by accessory domains. This condensation-reduction cycle is repeated by subsequent downstream modules until the intermediate is liberated from the enzyme, most commonly by the activity of a thioesterase domain (reviewed in (Khosla, 2009)).

Engineering of type I modular PKSs has the potential to produce an enormous variety of novel, rationally-designed compounds. Yet, more than two decades after their modular nature was discovered (Donadio et al., 1991), there are currently no commercial applications of engineered PKSs.

SUMMARY OF THE INVENTION

The present invention provides for a polyketide synthase (PKS) capable of synthesizing a carboxylic acid, said PKS comprising a synthetic module comprising the S3c variant module, or a functional variant thereof, wherein the PKS is capable of synthesizing a carboxylic acid.

The present invention also provides for a polyketide synthase (PKS) capable of synthesizing a carboxylic acid, said PKS comprising a hybrid module comprising a BorA2 KS domain, or functional variant thereof, a BorA2 AT domain, or functional variant thereof, a DH described in Example 1, or functional variant thereof, a heterologous KR domain, a heterologous ER domain, and a BorA2 ACP domain, or functional variant thereof, wherein the PKS is capable of synthesizing a carboxylic acid.

The present invention provides for a recombinant nucleic acid that encodes a polyketide synthase (PKS) of the present invention. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the carboxylic acid or diacid.

The present invention provides for a host cell comprising any of the recombinant nucleic acid and/or PKS of the present invention. In some embodiments, the host cell, when cultured, is capable of producing a carboxylic acid or diacid.

The present invention provides a method of producing a carboxylic acid or diacid, comprising: providing a host cell of the present invention, and culturing said host cell in a suitable culture medium such that the carboxylic acid or diacid is produced.

The present invention provides for a composition comprising a carboxylic acid or diacid isolated from a host cell from which the carboxylic acid or diacid was produced, and trace residues and/or contaminants of the host cell. Such trace residues and/or contaminants include cellular material produced by the lysis of the host cell. In some embodiments, the trace residues and/or contaminants do not or essentially do not interfere or retard a polymerization reaction involving the carboxylic acid or diacid.

BRIEF DESCRIPTION OF THE DRAWINGS

The foregoing aspects and others will be readily appreciated by the skilled artisan from the following description of illustrative embodiments when read in conjunction with the accompanying drawings.

FIG. 7. Junctions for DH swap constructs. Arrows indicates crossover point. The amino acid sequence of *Streptomyces parvulus* BorA2 is SEQ ID NO:6. The amino acid sequence of *Streptomyces thioluteus* AurB is SEQ ID NO:7. The amino acid sequence of *Streptomyces antibioticus* IdmO is SEQ ID NO: 8. The amino acid sequence of *Saccharopolyspora spinosa* SpnB is SEQ ID NO:10.

FIG. 8. N-terminal junctions including junction 3. Arrows and lines indicate crossover points. The amino acid sequence of *Streptomyces parvulus* BorA2 is SEQ ID NO:6. The amino acid sequence of *Streptomyces thioluteus* AurB is SEQ ID NO:7. The amino acid sequence of *Saccharopolyspora spinosa* SpnB is SEQ ID NO:10.

DETAILED DESCRIPTION

Figure 1A:
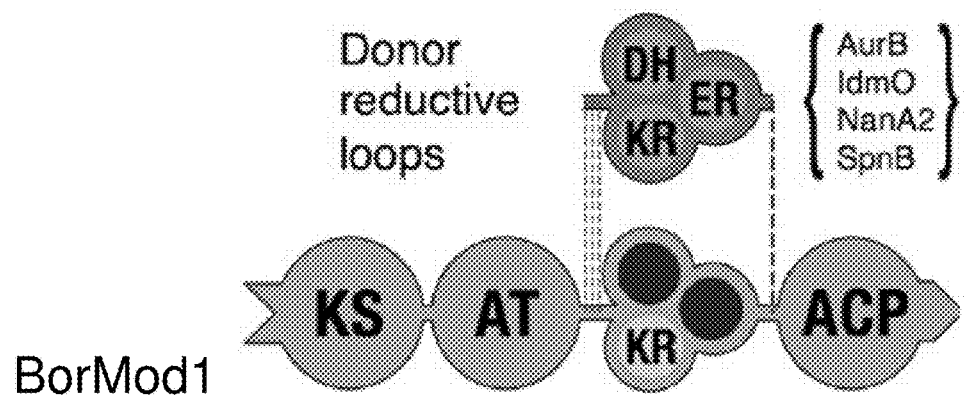
FIG. 1A shows loops were introduced combinatorially into BorMod1 using two alternative N-terminal and a single C-terminal splice sites to generate eight chimeras to be tested for adipoyl-ACP production. Abbreviations: KS: ketosynthase domain; AT: acyltransferase domain; KR: ketoreductase domain; DH: dehydratase domain; ER: enoylreductase domain; ACP: acyl carrier protein domain.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a diacid" includes a plurality of such diacids, and so forth.

The term "functional variant" describes an enzyme that has a polypeptide sequence that is at least 70%, 75%, 80%, 85%, 90%, 95% or 99% identical to any one of the enzymes described herein. The "functional variant" enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity as compared to the enzyme described herein. The "functional variant" enzyme has an enzymatic activity that is identical or essentially identical to the enzymatic activity of the enzyme described herein. The "functional variant" enzyme may be found in nature or be an engineered mutant thereof.

These and other objects, advantages, and features of the invention will become apparent to those persons skilled in the art upon reading the details of the invention as more fully described below.

This invention provides for an engineered enzyme capable of production of hexane 1,6-dicarboxylic acid ("adipic acid") when used in conjunction with its native loading module or provided a synthetic substrate. Successful production of adipic acid comprises one or more of the following: (1) selection of suitable reductive loop donors, (2) elucidating chimeric junction boundaries that result in high enzyme activity, (3) replacement of the dehydratase domain in the reductive loop, and (4) concatenation of a thioesterase domain.

In some embodiments, the enzyme is loaded with a succinic acid analog (presented as succinyl-acyl carrier protein ("succinyl-ACP") from the upstream loading module or as a synthetic succinyl-n-acetyl-cysteamine ("succinyl-SNAC"), which is then condensed with malonyl-coenzyme A ("malonyl-CoA") to produce 3-keto-adipic-acyl carrier protein ("3-keto-adipic-ACP"). The engineered "reductive loop" processively reduces this intermediate with NADPH to adipic-acyl-carrier protein ("adipic-ACP"), which is hydrolytically released from the enzyme by the action of the thioesterase ("TE") domain. An aspect of the invention is the replacement of the dehydratase domain in the reductive loop.

Polyketide Synthases (PKS)

In some embodiments, the synthetic module comprises one or more of the following domains: a BorA2 KS domain, or functional variant thereof, a BorA2 AT domain, or functional variant thereof, a DH described in Example 1, or functional variant thereof, a heterologous KR domain, a heterologous ER domain, and a BorA2 ACP domain, or functional variant thereof.

In some embodiments, the heterologous KR domain is a KR domain of AurB, IdmO, NanA2, or SpnB, or a functional variant thereof. In some embodiments, the heterologous ER domain is an ER domain of AurB, IdmO, NanA2, or SpnB, or a functional variant thereof.

In some embodiments, the PKS further comprises a second module comprising a BorA1 AT domain, or a functional variant thereof, and a BorA1 ACP domain, or a functional variant thereof.

Figure 10:
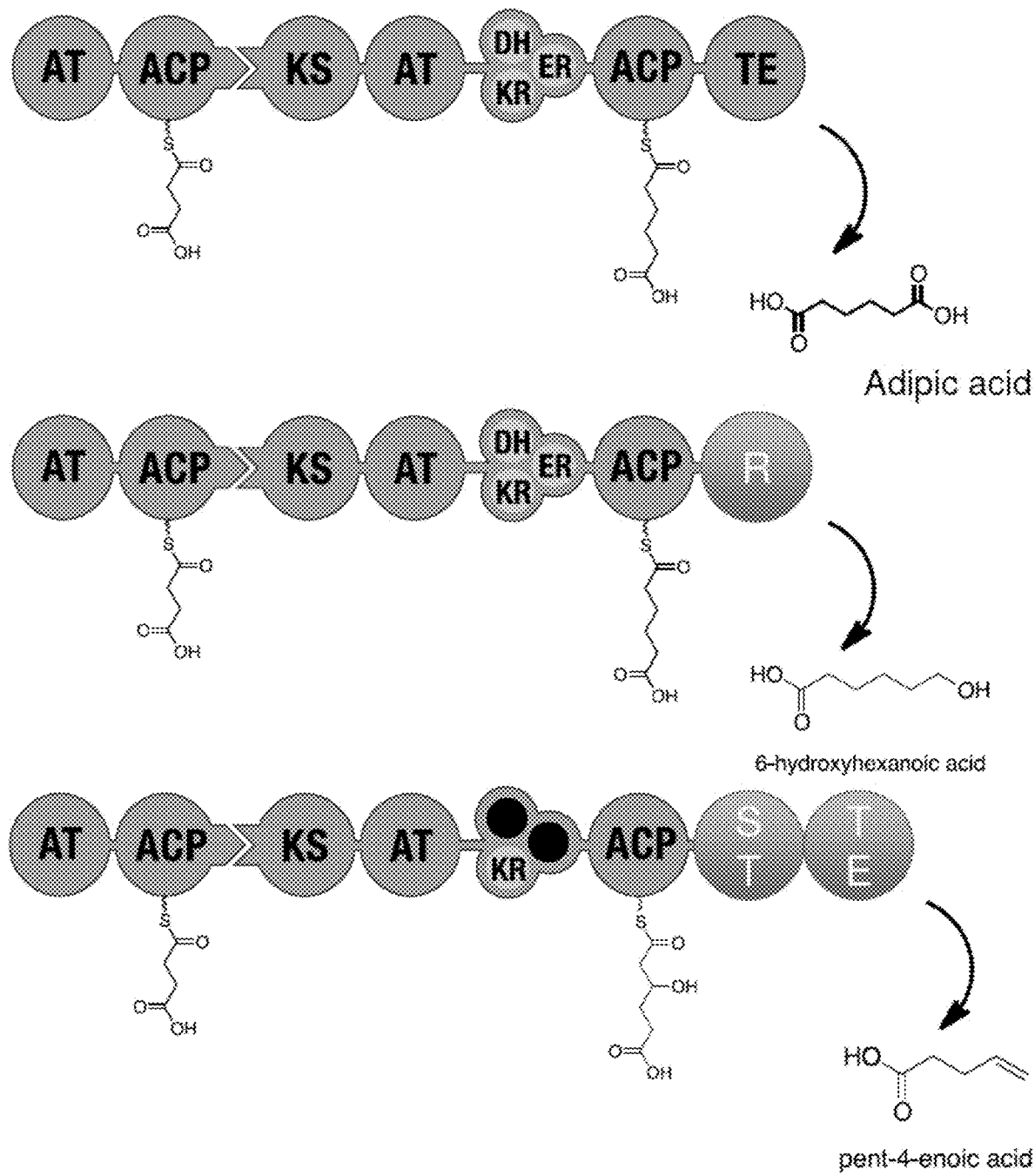
FIG. 10 shows different domains for terminating the synthesis of the compound. Abbreviations: KS: ketosynthase domain; AT: acyltransferase domain; KR: ketoreductase domain; DH: dehydratase domain; ER: enoylreductase domain; ACP: acyl carrier protein domain; TE: thioesterase.

In some embodiments, the PKS further comprises one or more extender modules or domains, and a thioesterase (TE) domain, such as ery TE, or an R domain. In some embodiments, the PKS is modified as shown in FIG. 10 wherein the PKS has the domains KR-ACP-ST-TE.

In some embodiments, the PKS further comprises one or more extender modules or domains between the synthetic module or hybrid module, and TE domain or R domain.

The amino acid sequence of the S3c variant is:

(SEQ ID NO: 1)
MAHEDKLRHLLKRVSAELDDTQRRVREMEESEREPIAIVGMSCRLPGGVN

SPGEFWSLLEAGTDAVSEFPRDRGWDVENLYDPDPDAPGRSYVREGGFLD

GAGQFDAAFFGISPREALAMDPQQRLLLECSWEAIERSRIDPKTLHGSRT

GVFAGSNWQDYNTLLLNAEERSQSYLATGASGSVLSGRVSYTLGMEGPAI

TVNTACSSSLVAVHLAARSLRAGECDLALAGAVTVMSTPQLPVAFSRQRG

LAPDGRSKAFAVSADGMGFGEGVGVLVLERLSVARRNGHRVLAVVRGSAV

NQDGASNGLTAPNGPSQQRVIRAALASAGLGPADVDVVEAHGTGTRLGDP

IEAQALLATYGRGRDAERPLWLGSVKSNIGHAQAAAGVAGVIKMVLAMEK

GRLPRTLHVDEPSGEVDWDSGAVRLLTEARDWPSEEGRLRRAGVSSFGIS

GTNAHVIIEEAPEEGEEPESDAGGVVPWVLSARTEGALQAQAVQLSEFVG

ESSPVDVGWSLVSTRAAFEHRAVVVGRGRDELVRGLSEVAQGRGVRGVAS

SASGGLAFVFAGQGSQRLGMGRGLYERFPVFAEAFDEVCGRVGPGVREVV

FGSDAGELDRTVWAQAGLFALEVALFRLLESWGVRPGCLIGHSVGELSAA

CVAGLWSLEDACRVVAARARLMQALPAGGVMVAVRAEAGELAGFLGEDVV

IASVNAPGQVVIAGPEGGVERVVAACGARSRRLAVSHAFHSPLVEPMLGE

FRRVVESVAFGVPSLRVVSNVTGAWVDPEEWGTPEYWVRQVREPVRFADG

VATLLDAGVRTFVELGPAGALTSMVSHCADATATSVTAVPTLRPDHDESR

TVLSAAASLYVQGHPVDWAPLFPRARTVDLPTYPFQHQHYWMMNTGSAAE

PAELGLGDARHPLLGSVVTVAGDDKVVFAGRLALRTHPWLADHTVLDAVL

LPATAFLELAVRAGEEVSCPVVHDLTLHRPLVVPERGAVQVQMAVGAPEA

DGRREVRVYSRPDDDAEHEWTLHAAGLLASAATAEPAVAAGAWPPPEAQA

VDLDGFYAGLAEHGYHYGPLFQGVRAAWRLGDDVLAEIVLPEAAGADAAR

YGMHPALLDAVLHAARLGAFRERSEEKYLPFAWEGVTLRTRGATAVRARI

SRAGTDAIRLDVTDTADRPVLTAESLVLRSAAARRTGARRQAHQARLYRL

SWPTVQLPTSAQPPSCVLLGTSEVSADIQVYPDLRSLTAALDAGAEPPGV

VIAPTPPGGGRTADVRETTRHALDLVQGWLSDQRLNESRLLLVTQGAVAV

EPGEPVTDLAQAALWGLLRSTQTEHPDRFVLVDVPEPAQLLPALPGVLAC

GEPQLALRRGGAHAPRLAGLGSDDVLPVPDGTGWRLEATRPGSLDGLALV

DEPTATAPLGDGEVRIAMRAAGVNFRDALIALGMYPGVASLGSEGAGVVV

ETGPGVTGLAPGDRVMGMIPKAFGPLAVADHRMVTRIPAGWSFARAASVP

IVFLTAYYALVDLAGLRPGESLLVHSAAGGVGMAAIQLARHLGAEVYATA

SEDKWQAVELSREHLASSRTCDFEQQFLGATGGRGVDVVLNSLAGEFADA

SLRMLPRGGRFLELGKTDVRDPVEVADAHPGVSYQAFDTVEAGPQRIGEM

LHELVELFEGRVLEPLPVTAWDVRQAPEALRHLSQARHVGKLVLTMPPVW

DAAGTVLVTGGTGALGAEVARHLVIERGVRNLVLVSRRGPAASGAAELVA

QLTAYGAEVSLQACDVADRETLAKVLASIPDEHPLTAVVHAAGVLDDGVS

ESLTVERLDQVLRPKVDGARNLLELIDPDVALVLFSSVSGVLGSGGQGNY

AAANSFLDALAQQRQSRGLPTRSLAWGPWAEHGMASTLREAEQDRLARSG

LLPISTEEGLSQFDAACGGAHTVVAPVRFSRLSDGNAIKFSVLQGLVGPH

```
RVNKAATADDAESLRKRLAALPEADRRRAVLDLVEELVLGVLGHETRAAI
GPDSSFHAIGFDSLTAVELRNLLTVRLGMKLPATLVYDHPTLSSLADHLH
EQLVIDGTPMTDTAADLLAELDALAARLAAVGLEPEARARIGRRLKDMQT
ACEPRSESSRDLKSASRTEVLDFLTNELGISR
```

The amino acid sequence of the S3c variant with ery TE is:

```
                                              (SEQ ID NO: 2)
MAHEDKLRHLLKRVSAELDDTQRRVREMEESEREPIAIVGMSCRLPGGVN
SPGEFWSLLEAGTDAVSEFPRDRGWDVENLYDPDPDAPGRSYVREGGFLD
GAGQFDAAFFGISPREALAMDPQQRLLLECSWEAIERSRIDPKTLHGSRT
GVFAGSNWQDYNTLLLNAEERSQSYLATGASGSVLSGRVSYTLGMEGPAI
TVNTACSSSLVAVHLAARSLRAGECDLALAGAVTVMSTPQLPVAFSRQRG
LAPDGRSKAFAVSADGMGFGEGVGVLVLERLSVARRNGHRVLAVVRGSAV
NQDGASNGLTAPNGPSQQRVIRAALASAGLGPADVDVVEAHGTGTRLGDP
IEAQALLATYGRGRDAERPLWLGSVKSNIGHAQAAAGVAGVIKMVLAMEK
GRLPRTLHVDEPSGEVDWDSGAVRLLTEARDWPSEEGRLRRAGVSSFGIS
GTNAHVIIEEAPEEGEEPESDAGGVVPWVLSARTEGALQAQAVQLSEFVG
ESSPVDVGWSLVSTRAAFEHRAVVVGRGRDELVRGLSEVAQGRGVRGVAS
SASGGLAFVFAGQGSQRLGMGRGLYERFPVFAEAFDEVCGRVGPGVREVV
FGSDAGELDRTVWAQAGLFALEVALFRLLESWGVRPGCLIGHSVGELSAA
CVAGLWSLEDACRVVAARARLMQALPAGGVMVAVRAEAGELAGFLGEDVV
IASVNAPGQVVIAGPEGGVERVVAACGARSRRLAVSHAFHSPLVEPMLGE
FRRVVESVAFGVPSLRVVSNVTGAWVDPEEWGTPEYWVRQVREPVRFADG
VATLLDAGVRTFVELGPAGALTSMVSHCADATATSVTAVPTLRPDHDESR
TVLSAAASLYVQGHPVDWAPLFPRARTVDLPTYPFQHQHYWMMNTGSAAE
PAELGLGDARHPLLGSVVTVAGDDKVVFAGRLALRTHPWLADHTVLDAVL
LPATAFLELAVRAGEEVSCPVVHDLTLHRPLVVPERGAVQVQMAVGAPEA
DGRREVRVYSRPDDDAEHEWTLHAAGLLASAATAEPAVAAGAWPPPEAQA
VDLDGFYAGLAEHGYHYGPLFQGVRAAWRLGDDVLAEIVLPEAAGADAAR
YGMHPALLDAVLHAARLGAFRERSEEKYLPFAWEGVTLRTRGATAVRARI
SRAGTDAIRLDVTDTADRPVLTAESLVLRSAAARRTGARRQAHQARLYRL
SWPTVQLPTSAQPPSCVLLGTSEVSADIQVYPDLRSLTAALDAGAEPPGV
VIAPTPPGGGRTADVRETTRHALDLVQGWLSDQRLNESRLLLVTQGAVAV
EPGEPVTDLAQAALWGLLRSTQTEHPDRFVLVDVPEPAQLLPALPGVLAC
GEPQLALRRGGAHAPRLAGLGSDDVLPVPDGTGWRLEATRPGSLDGLALV
DEPTATAPLGDGEVRIAMRAAGVNFRDALIALGMYPGVASLGSEGAGVVV
ETGPGVTGLAPGDRVMGMIPKAFGPLAVADHRMVTRIPAGWSFARAASVP
IVFLTAYYALVDLAGLRPGESLLVHSAAGGVGMAAIQLARHLGAEVYATA
SEDKWQAVELSREHLASSRTCDFEQQFLGATGGRGVDVVLNSLAGEFADA
SLRMLPRGGRFLELGKTDVRDPVEVADAHPGVSYQAFDTVEAGPQRIGEM
LHELVELFEGRVLEPLPVTAWDVRQAPEALRHLSQARHVGKLVLTMPPVW
DAAGTVLVTGGTGALGAEVARHLVIERGVRNLVLVSRRGPAASGAAELVA
QLTAYGAEVSLQACDVADRETLAKVLASIPDEHPLTAVVHAAGVLDDGVS
ESLTVERLDQVLRPKVDGARNLLELIDPDVALVLFSSVSGVLGSGGQGNY
AAANSFLDALAQQRQSRGLPTRSLAWGPWAEHGMASTLREAEQDRLARSG
LLPISTEEGLSQFDAACGGAHTVVAPVRFSRLDGNAIKFSVLQGLVGPH
RVNKAATADDAESLRKRLAALPEADRRRAVLDLVEELVLGVLGHETRAAI
GPDSSFHAIGFDSLTAVELRNLLTVRLGMKLPATLVYDHPTLSSLADHLH
EQLESGTPAREASSALRDGYRQAGVSGRVRSYLDLLAGLSDFREHFDGSD
GFSLDLVDMADGPGEVTVICCAGTAAISGPHEFTRLAGALRGIAPVRAVP
QPGYEEGEPLPSSMAAVAAVQADAVIRTQGDKPFVVAGHSAGALMAYALA
TELLDRGHPPRGVVLIDVYPPGHQDAMNAWLEELTATLFDRETVRMDDTR
LTALGAYDRLTGQWRPRETGLPTLLVSAGEPMGPWPDDSWKPTWPFEHDT
VAVPGDHFTMVQEHADAIARHIDAWLGGGNS*
```

The amino acid sequence of *Streptomyces parvulus* BorA1 is:

```
                                              (SEQ ID NO: 5)
         10         20         30         40         50
 MTGSAVSAPF LQPPEPVSGH SERKSDPVLL VGAGRRARMA DAVRAAGAQA 60         70         80         90        100
 GIDPAVLRRT RATLITAGSA GAAGRLAAAL RLTGATISLD TRETPTLLAL 110        120        130        140        150
 HLAAQALRAG DTSYAVVGAE LPDGNCALIL ARQSAATAEG AVPQAIVRTT 160        170        180        190        200
 TADRTTTADH APAPDDHGSP AREAPHATRT LSPGITQAPA EGFPGLLATL 210        220        230        240        250
 HDDTPLRPTA VTEHGSDATT VLVLLDQPQD AAPAAPLPWV VSAPHTRALR 260        270        280        290        300
 ATAATLAVHL DTTPAAPADV AHTLLTARPD RHRAAVVGAD RATLTDGLRA 310        320        330        340        350
 LATGGDAPHL VHGTATGSPR PVFVFPGQGS QWPGMAAELL ETSEPFHDSV
```

-continued

```
       360        370        380        390        400
HACADALAEF VDWSVLDVLR QAPDAPPLRR VDVLQPTLWA TMVSLAEVWR 410        420        430        440        450
SYGVEPAAVV GHCCGEIAAA QVAGALDMRD AARLLAHRSR AWLRLVGKGT 460        470        480        490        500
VISVATSGQD ITRRMAAWPD SVELAALNGP RSVALAGPPD VLDGIVNDLT 510        520        530        540        550
DQGIHAKRIP GVDTVGHCSQ VEVLRDHLLD VLRPVSPRPA AVPFYSTVDG 560        570        580        590        600
TERDTTTLDT DYWYLNTRSQ VRFHQAVRNL LAAGHRSFVE VSPHPLLGAS 610        620        630        640        650
IEDTAAEFGL DDVAAVGTLR RGQGGTRRVL TSVAEAYVHG IDIDFTPAFT 660        670        680        690        700
GTTPNRIDLP TVEDHGIEGH GDDGGETWTD RVRTLPDEQR EEALLDLVCR 710        720        730        740        750
TVAAVLEADP AGTADAVAPD TAFKEMGLGS LSAVRLRNGL REATGAHLPA 760        770        780        790        800
TIAYDHPTPA ALARHLAMTL FDATGAAPAV PAPSRDDEPI DAETAVLTAL 810        820        830        840        850
ERADEALERL RAPHARTPRQ ETGRRIDELL RSLTDKARRM RQADAVDDVD 860        870
DPATDRFAAA TDDEMFELLE KRFGIS
```

The amino acid sequence of *Streptomyces parvulus* BorA2 is:

```
                                                (SEQ ID NO: 6)
        10         20         30         40         50
MAHEDKLRHL LKRVSAELDD TQRRVREMEE SEREPIAIVG MSCRLPGGVN 60         70         80         90        100
SPGEFWSLLE AGTDAVSEFP RDRGWDVENL YDPDPDAPGR SYVREGGFLD 110        120        130        140        150
GAGQFDAAFF GISPREALAM DPQQRLLLEC SWEAIERSRI DPKTLHGSRT 160        170        180        190        200
GVFAGSNWQD YNTLLLNAEE RSQSYLATGA SGSVLSGRVS YTLGMEGPAI 210        220        230        240        250
TVNTACSSSL VAVHLAARSL RAGECDLALA GAVTVMSTPQ LPVAFSRQRG 260        270        280        290        300
LAPDGRSKAF AVSADGMGFG EGVGVLVLER LSVARRNGHR VLAVVRGSAV 310        320        330        340        350
NQDGASNGLT APNGPSQQRV IRAALASAGL GPADVDVVEA HGTGTRLGDP 360        370        380        390        400
IEAQALLATY GRGRDAERPL WLGSVKSNIG HAQAAAGVAG VIKMVLAMEK 410        420        430        440        450
GRLPRTLHVD EPSGEVDWDS GAVRLLTEAR DWPSEEGRLR RAGVSSFGIS 460        470        480        490        500
GTNAHVIIEE APEEGEEPES DAGGVVPWVL SARTEGALQA QAVQLSEFVG 510        520        530        540        550
ESSPVDVGWS LVSTRAAFEH RAVVVGRGRD ELVRGLSEVA QGRGVRGVAS 560        570        580        590        600
SASGGLAFVF AGQGSQRLGM GRGLYERFPV FAEAFDEVCG RVGPGVREVV 610        620        630        640        650
FGSDAGELDR TVWAQAGLFA LEVALFRLLE SWGVRPGCLI GHSVGELSAA 660        670        680        690        700
CVAGLWSLED ACRVVAARAR LMQALPAGGV MVAVRAEAGE LAGFLGEDVV
```

```
              710        720        730        740        750
         IASVNAPGQV VIAGPEGGVE RVVAACGARS RRLAVSHAFH SPLVEPMLGE 760        770        780        790        800
         FRRVVESVAF GVPSLRVVSN VTGAWVDPEE WGTPEYWVRQ VREPVRFADG 810        820        830        840        850
         VATLLDAGVR TFVELGPAGA LTSMVSHCAD ATATSVTAVP TLRPDHDESR 860        870        880        890        900
         TVLSAAASLY VQGHPVDWAP LFPRARTVDL PTYPFQHQHY WLDVPPLFTA 910        920        930        940        950
         SSAAQDGGWR YRIHWRRLGT RDSGDRLSGR WLLLVPESDG TEPWVEGAEK 960        970        980        990       1000
         MLAERGCEVV HVPIAATADR DAMVGAVRES VEDGRVDGVL SLLALDGRPH 1010       1020       1030       1040       1050
         PDAAAVPTGL VATAQVVQVS DELGIGPLWV ATRQAVSVDG ADEADGAGRT 1060       1070       1080       1090       1100
         RKADDPADVA QAAVWGLGRV AALEKPRLWG GLVDLPARAD ERMRDLVAQA 1110       1120       1130       1140       1150
         LTAPDAEDQL AVRADGIAVR RLVRSAASAP ADDWQPSGTV LVTGGTGGVG 1160       1170       1180       1190       1200
         ANVARWLVTQ DIQHLLLVSR RGPDAPGAAE LLAELSASGT SVTIEPCDVT 1210       1220       1230       1240       1250
         DADAVRRLIG AVPAERPLST VVHAAGVLDD CLIDALTPQR LAAALEVKAK 1260       1270       1280       1290       1300
         GALNLHEAAG EAHLVLFSSL AGTTGTKGQG NYAAANAYLD ALAERRRADG 1310       1320       1330       1340       1350
         LPATSVAWGA WQGAGMVADA AVAHRTRRYG LPLMSPDRAV ATLRQVMAEP 1360       1370       1380       1390       1400
         VATQVVADVD WQRFVADFTA VRPSRLLADL PEVRSLGEQR KDGPGGQGEE 1410       1420       1430       1440       1450
         DGLASKLAAL PEADRRRAVL DLVEELVLGV LGHETRAAIG PDSSFHAIGF 1460       1470       1480       1490       1500
         DSLTAVELRN LLTVRLGMKL PATLVYDHPT LSSLADHLHE QLVIDGTPMT 1510       1520       1530       1540       1550
         DTAADLLAEL DALAARLAAV GLEPEARARI GRRLKDMQTA CEPRSESSRD 1560       1570
         LKSASRTEVL DFLTNELGIS R
```

The amino acid sequence of *Streptomyces thioluteus* AurB is:

```
                                             (SEQ ID NO: 7)
              10         20         30         40         50
         MTNDAKTLEY LKRLTAELLE TRERLRTAEA ADQEPVAVVS MGCRYPGGVS 60         70         80         90        100
         SPEDLWRLVT DGTDAIAPFP ADRGWNVDDL FDPDPDRPGR TYTLEGGFVD 110        120        130        140        150
         GAAEFDADLF GISPREATAM DPQQRLLLET AWETFERAGT DPGSLRGRPV 160        170        180        190        200
         GVFVGSLFVA GGSGVGVAEG AEGYHMTGNA ASVLSGRLAY AFGLEGPAVT 210        220        230        240        250
         VDTACSASLV AVHQAVQALR QGECALALAG GSTVMTTPGV FTEFSRQRGL 260        270        280        290        300
         APDGRCKAFA TAADGTGFGE GVGLVLLEKL SDARKNGHPV LAVIRGSAVN 310        320        330        340        350
         QDGASNGLTA PNGPSQQRVI RQALAAARVS ADEVDVVEAH GTGTGLGDPV
```

-continued

```
           360        370        380        390        400
    EAQALLATYG QGRPDDRPLW LGSIKSNLGH TQGAAGVAGL IKMVMAVRHG 410        420        430        440        450
    VLPMTLHVDE PSAHVDWDSG AVRLLTGNHD WPETGRPRRA GVSSFGISGT 460        470        480        490        500
    NAHLILEQAP DAEESDAEPA SGAPARIPWV LAARGEEALR AQAERLLTEV 510        520        530        540        550
    RDRPELRPVD VGHALATSRA ALDQRAVVWA DGRDGLLAAL TALAEERPAP 560        570        580        590        600
    GVVHGTVADG RLAFLFSGQG SQRPGMGHEL TESFPVFAEK LDEVCGHLDR 610        620        630        640        650
    HLDRPLRELL FAAEGTPEAA LLEQTGYTQA ALFAHEVALH HLLTHWGITP 660        670        680        690        700
    DLLLGHSIGE LTAAHVAGVL SLEDACALVA ARGRLMQQLP GAGAMLSVQA 710        720        730        740        750
    TEAEVLPWVT EHAHEMSIAA VNGPRSVVVS GAESAVLEFA EHWKNEGRKT 760        770        780        790        800
    KRLRVSHAFH SPQMDGMLQE FARVAEKLAF HPPRIPVVSN VTGEVATAEQ 810        820        830        840        850
    LCSPAYWVRH AREAVRFHDG IRRLVAEGAH VFLEVGPSGV LTAMAQDCLA 860        870        880        890        900
    DEPGTVTAAV SRGGRPEADA ALAAVAEAYV HGVRVDWDRF FAGTGARRID 910        920        930        940        950
    LPTYAFRRRS FPWIQAAPDA DVTTAGLAGL GHPLLGASLE LADAQGAALS 960        970        980        990       1000
    GRLSARTESW LADHVVLGST LVPGTAVVEM AVRAGAETGC GRLAELTQEA 1010       1020       1030       1040       1050
    PLAVPERGAV HLQVRVGPAG EQGHRPVGVY SRPEDAEPDE PWACHARGVL 1060       1070       1080       1090       1100
    APEAAPVPAG TGGAWPPSGA EPVPLDGFYE RLAAEGFAYG PAFQGLTRAW 1110       1120       1130       1140       1150
    RLGDEVLAEI TLPEGACSGA DRYGVHPALL DAALHTALLK EEASDTSQVR 1160       1170       1180       1190       1200
    IPFAWHEVSF HGGSAPVLRA RLTPSGTDTV SLALWDEHGT PVASVGSLVS 1210       1220       1230       1240       1250
    RPVSARQLRA TRTHDTLFRL DWVETTITPA AARCAVLGDD ELAGALSVPA 1260       1270       1280       1290       1300
    FADLAALESA DPVPELVLYP CLGDDAEDDR ADAARSLTAR VLGVLQAWVA 1310       1320       1330       1340       1350
    DERWATTRLA LVTRGAMSVT DREQVTDLPA AAVWGLVRSA QAEHPGRFVL 1360       1370       1380       1390       1400
    ADLDGDTASA AALPGILAAS GDEPQLALRE GAVLVPRLAR GVPSGTLVPP 1410       1420       1430       1440       1450
    PGTRDWHLEL TGGGTVDDLA LTPFPEAAAP LAPGQVRVAV RAAGLNFRDV 1460       1470       1480       1490       1500
    VMALGMVDDR RALGGEIAGI VTEAGPGVTG FAPGDRVFGL ADGCIGPVAV 1510       1520       1530       1540       1550
    VDHRLIARIP EGWSFPQAAS VPVTFLTAYY GLVDLAGVRP GDRVLVHAAA 1560       1570       1580       1590       1600
    GGVGMAAVQL ARHLGAEVFA TAGPAKWDTV RALGIDDDHL ASSRTDEFET 1610       1620       1630       1640       1650
    RFAAEDGGRG IDVVLNSLAG EMADASLRLV RPGGRFIEMG KTDIRDADEV 1660       1670       1680       1690       1700
    AAAYEGVVYR AFDLMDGGAE CIARIFAELL ALFEGGKIQL VPVTTWDVRQ
```

```
                         -continued
      1710        1720        1730        1740        1750
  APEAFRYFAQ  ARHVGKIVLT  VPPAWDPEGT  VLVTGASGGV  AAHLVRHLVR 1760        1770        1780        1790        1800
  THDVRHLLLA  SRRGPDAEGM  DELIAELRES  GAHSVRAVAC  DCVDRTAVAD 1810        1820        1830        1840        1850
  LLASIPDEHP  LTAVVHTVGV  VDDGVLETMT  PERIDAVFRP  KADGAWHLHE 1860        1870        1880        1890        1900
  LTRDRDLAAF  AVCSSVAGTL  GSAAQANYAA  ANAFLDALAA  HRRDHGLPAT 1910        1920        1930        1940        1950
  SLAWGMWAGT  GGMAANLSRA  DLDRMQRSGI  SGLSTEEGLA  LFDAALAAGR 1960        1970        1980        1990        2000
  PVWLPARLDA  KALRTAAGGG  SLPAPLRGLV  HVPAADAGPL  PAADALRGRL 20 10       20 20       2030        2040        2050
  ASLAPEERHE  AVLDVVRAQV  AVVLGHGAPE  GIDPQRAFKD  LGFDSLTAVE 20 60       20 70       2080        2090        2100
  LRNRLNAAAG  LTLPATLVFD  HPTPAALTDH  IESVLLAGLG  SPADPLLARL 2110        2120        2130        2140        2150
  DDWAAGLAAT  ALDDDERERV  AARLRALAGQ  WGAPDDGATS  IADELDGATD

2160
  DEVLDFISNE  LGIS
```

The amino acid sequence of *Streptomyces antibioticus* IdmO is:

```
                                              (SEQ ID NO: 8)
        10         20         30         40         50
   MHMVGVEEKL RDYLRRVTGE LSETRQRLKE AEAESREPIA IVSMACRFPG 60         70         80         90        100
   GIESPQDYWR LLAEGRDAVA GFPDDRGWDL DNLFDPDPDA PGKSYAREGA 110        120        130        140        150
   FVHGASEFDA ELFGISPREA LSMDPQQRLL LEAAWEVFER AGLDPGALKG 160        170        180        190        200
   RDIGVFAGAA WSDYVSGSRK VPDSAEGYAI TGGSSSVLSG RVAYTFGLEG 210        220        230        240        250
   PAVTVDTACS SSLVAMHLAS QALRSGECSM ALAGGVSVLV SPYPFVGFSR 260        270        280        290        300
   QRGLAPDGRC KPFADRADGT GWGEGVGMLL LERLSDARRN GHEVLAVLRG 310        320        330        340        350
   SAVNQDGASS GLTAPNGPSQ QRVIRAALAN AGLTASDVDA VEAHGTGTSL 360        370        380        390        400
   GDPIEAQALL ATYGQGRPEG RPLWLGSVKS NIAHTQATAG AAGVIKMVLA 410        420        430        440        450
   MRHGLLPKSL HVDAPSTNVD WSAGAVELLT VAREWPEVDR PWRAGVSSFG 460        470        480        490        500
   VSGTNAHVIV EEAPESSADA VAESGVRVPV PVVPWVVSAR SAEGLAAQAE 510        520        530        540        550
   RLARFVGERS DQDPVDIGFS LVRSRSLLEH RAVVLGKGRD DLVAGLASLA 560        570        580        590        600
   SDGSATGVVS GVARGRARVA FGFSGQGAQR VGMGAELASV YPVFAEALAE 610        620        630        640        650
   VTGALGLDPE VFGDVDRLGR TEVTQAALFA FEVAVVRLLE SFGVRPDVLI 660        670        680        690        700
   GHSIGEIAAA YVAGVFSLGD AAALVGARGR LMQALPAGGV MVAVQAGEAE 710        720        730        740        750
   VVAALEGFAD RVSLAAVNGP SSVVVSGEAE AVEQVVARLG KVKSKRLRVS
```

```
            760        770        780        790        800
HAFHSPLMEP MLADFRQVAE QITYNEPQLP VVSNVSGRLA EPGELTTPDY 810        820        830        840        850
WVRHVREAVR FGDGVRALAA DGVGVLVEVG PDSVLTALAR ESLDGEDGLR 860        870        880        890        900
AVPLLRKDRP EPETLLTGVA QAFTHGVQVD WPALLPGGRR VELPTYAFQR 910        920        930        940        950
RRYWLEDADP TGGDPAALGL TAADHPLLGA AVPLAEDQGI VITSRLSLRT 960        970        980        990       1000
HPWLADHEIG GTVLLPGAGL VEIALRAGDE VGCGRVEELT LEIPLVVPQE 1010       1020       1030       1040       1050
GGVTVQIRVG APDESGWRPM TVHSRTDPEE EWTRHVSGVL SPDVPTERYD 1060       1070       1080       1090       1100
LGAWPPAGAT PVELDGFYEA YARLGYAYGP SFQGLRAAWR RGDEVFAEVS 1110       1120       1130       1140       1150
LPVEEQETAG RFTLHPALLD AALQSAGAGA FFDSGGSMRL PFAWSGVSVF 1160       1170       1180       1190       1200
AAGASTVRVR LSPAGPDAVT VALADPTGAP VALVERLLIP EMSPEQLERV 1210       1220       1230       1240       1250
RGEEKEAPYV LDWVPVEVPA DDLVRPERWT LLGGADAGVG LDVAGAFASL 1260       1270       1280       1290       1300
EPSDGAPEFV VLPCVPPTSP TRAADVRQST LQALTVLQNW VTDERHADSR 1310       1320       1330       1340       1350
LVLVTRRAVG VGAHDDVPDL THAALWGLVR SAQTENPGRF LLVDLDEGAE 1360       1370       1380       1390       1400
LAEVLPGALG SGESQVAVRA GRVLAARLAR SGSGGAELVP PAGAPWRLDT 1410       1420       1430       1440       1450
TSPGTLENLA LVPSAEEPLG PLDVRVSVRA AGLNFRDVLI ALGMYPGDAR 1460       1470       1480       1490       1500
MGGEGAGVVT DVGSEVTTLA PGDRVMGMLS SAFGPTAVSD HRALVRVPDD 1510       1520       1530       1540       1550
WSFEQAASVP TVFATAYYGL VDLAELRAGQ SVLVHAAAGG VGMAAVQLAR 1560       1570       1580       1590       1600
HLGAEVFGTA STGKWDSLRA GGLDAEHIAS SRTVEFEETF LAATAGRGVD 1610       1620       1630       1640       1650
VVLDSLAGEF VDASLRLLPR GGRFVEMGKA DIRDAERVAA DHPGVTYRSF 1660       1670       1680       1690       1700
DLLEAGLDRF QEILTEVVRL FERGVLRHLP VTAWDVRRAA EAFRFVSQAR 1710       1720       1730       1740       1750
HVGKNVLVMP RVWDRDGTVL ITGGTGALGA LVARHLVAEH GMRNVLLAGR 1760       1770       1780       1790       1800
RGVDAPGARE LLAELETAGA QVSVVACDVA DRDAVAELIA KVPVEHPLTA 1810       1820       1830       1840       1850
VVHTAGVVAD ATLTALDAER VDTVLRAKVD AVLHLHEATR GLDLAGFVLF 1860       1870       1880       1890       1900
SSASGIFGSP GQGNYAAANS FIDAFAHHRR AQGLPALSLA WGLWARTSGM 1910       1920       1930       1940       1950
AGQLGHDDVA RISRTGLAPI TDDQGMALLD AALGAGRPLL VPVRLDRAAL 1960       1970       1980       1990       2000
RSQATAGTLP PILRGLVRAT VRRAASTAAA QGPSLAERLA GLPVTEHERI 2010       2020       2030       2040       2050
VVELVRADLA AVLGHSSSAG IDPGRAFQDM GIDSLTAVEL RNRLNGATGL 2060       2070       2080       2090       2100
RLAASLVFDY PTPNALATHI LDELALDTAG AGAAGEPDGP APAPADEARF
```

-continued

```
        2110       2120       2130       2140       2150
     RRVINSIPLD RIRRAGLLDA LLGLAGTSAD TAASDDFDQE EDGPAIASMD 2160       2170
     VDDLVRIALG ESDTTADITE GTDRS
```

The amino acid sequence of *Streptomyces nanchangensis* NanA2 is:

```
                                              (SEQ ID NO: 9)
         10         20         30         40         50
     MVSEEKLVEY LRRVTTELHD ARTRLRELEE GEQEPVAVVG MACRFPGGVR 60         70         80         90        100
     SPEDLRRLVL SGGDAIGDFP TDRGWDLDGL FHPDPAHFGT SYVSQGGFLY 110        120        130        140        150
     DVDRFDAGFF GISPREALAM DPQQRLLLEL SWEALESAGV VPGALRASRT 160        170        180        190        200
     GVYVGVSSED YISGLPQIPE GFEGYATTGS LTSVISGRVA YTFGFEGPAV 210        220        230        240        250
     TVDTACSSSM VAIHLAGQAL RQGECSLALA GGVTVLSTPL MFTEFCRQRA 260        270        280        290        300
     LTPDARCKPF AAAADGTGFS EGAGLLLLER LSDARRNGHE VLAVLRGSAI 310        320        330        340        350
     NQDGASNGLT APNDVAQESV IRDALARAGL SGADVDMVEA HGTGTRLGDP 360        370        380        390        400
     IEAEALIATY GADRPADRPL YLGSIKSNIG HTHAAAGVAG AINTVMALRD 410        420        430        440        450
     GKLARTLHID EPTRHVDWSA GTVRLLTDPY DWPVADRPRR AAVSSFGVSG 460        470        480        490        500
     TNAHVILEQA PDAGAQQDAR QRGGDTFHGV VPWPVSGRTE AALRDQAARL 510        520        530        540        550
     GAFLTADGAT ANGAATGGVA DVGWSLAMRR TAFEHRAVVV GRDRSDLLAA 560        570        580        590        600
     LEGLAADEPG PAVVRGVAAD VGAGPVMVFP GQGSQWLGMG VELLDSSPVF 610        620        630        640        650
     AARIAACERA LAAHVDWSLT DVLRGARGAA DIGRVDVVQP VLWAVMVSLA 660        670        680        690        700
     AVWEAHGVRP SAVVGHSQGE IAAACVAGAM TLEDGARVVA LRARALRALA 710        720        730        740        750
     GYGAMASLGC GVEETERLTA VHAPDVAVAA VNGPSSTVVS GPSEQVEKLV 760        770        780        790        800
     AAVRADGLRA RAIDVDYASH GPQVDRIADE LADVLAGVSG AATDTAFYST 810        820        830        840        850
     VTGARMDASG LDAGYWFTNL RQPVRFAEAV QALLDADYRV FIEVSAHPVL 860        870        880        890        900
     LLGLQECFEA AGRPAVAIGT LRRDEGGPER LCRALAEAHV AGVAVDWASW 910        920        930        940        950
     YADGPAPAAV PLPAYAFQRE RYWLPAGAGS GPGDVAGAGL TAVGHALLPV 960        970        980        990       1000
     SVRLADGSLV LTGRLPEAAR AGWLAEHLVA DLPLLPGTVL VEWVLRAADE 1010       1020       1030       1040       1050
     AGCGGVEELA LQVPVALPVS GGLVIQVVVD AAEGDRRPV RVHSRPEEDS 1060       1070       1080       1090       1100
     GAPDAWVCHV SGTLLPGVAG PVPPSGPGGA WPPPGARPAA IDGFYERAEA 1110       1120       1130       1140       1150
     AGYGYGAFFR GLTNVWHDGE DTLAEVVLPK EAAEQAGGFG IHPALLDAAM
```

-continued

```
      1160       1170       1180       1190       1200
QPVLLAGQLR QCAAAAGADT ASGTVLLPFT WSGVRLWAGG ATRLRVRLSP 1210       1220       1230       1240       1250
RPEGLRVLLA DATGAPVLTA DAVALRETGV QQLRASSRVR GSHGLFAVEW 1260       1270       1280       1290       1300
VPPLSATAGG TAPATLAVLG DDAPDLADAD RYPDLDALFR AVADGAPAPD 1310       1320       1330       1340       1350
VVIASVRTGN DPAGSDTGLA TARRTLTLAQ EWLAGSGADG ARLAVVTRSA 1360       1370       1380       1390       1400
IRTGDDGQER VVPSAAAVWG LMRSAQTEHP GRFVLIDEDT DSTENILEAV 1410       1420       1430       1440       1450
RTDEPQLALR GGRALVPRMA RVDAEPELTA PSGERAWHVA AGKTGPDDLT 1460       1470       1480       1490       1500
AVPSPRASAP LAPGQVRIAV RAAGLNFRDA LIALDMYPDA SASIGSEGAG 1510       1520       1530       1540       1550
VVLEVSEGVA GVAVGDRVMG LFNDAFGPVA VADARMVAPV PDGWSFREAA 1560       1570       1580       1590       1600
AAPVAFLTAW YGLVDLGGLS SGETVVIHGA AGGVGMAAVQ VARHLGAEVF 1610       1620       1630       1640       1650
ATASPAKHPV LEGMGVDAAH RASSRDLGFE AAFSSATGGR GVDVVLNSLA 1660       1670       1680       1690       1700
GEFTDASLRL LAPGGRLIEM GKTDVRDPDQ VAREHSVAYR AFDLIADAGP 1710       1720       1730       1740       1750
ERIGQLLAAL GERFADGAFT PLPVTGWRLG QARQALRQLS QARHTGKLVL 1760       1770       1780       1790       1800
DVDPAPDPDG TVLITGGTGT LGGLIAEHLV RSRGVRHLLL LSRRGPDAPG 1810       1820       1830       1840       1850
AEELTARLTE LGARVRVAAV DVGDATALGE AVAGVDPAHP LTGVVHAAGV 1860       1870       1880       1890       1900
VADAMLPSQD DERLVAAWSA KAAAAARLHD ATAGLPLGMF VLFSSFASTL 1910       1920       1930       1940       1950
GTAGQANYAA ANAYCDALVE RRHAEGLPGV SVSWGLWSAA SGLTGGLTEA 1960       1970       1980       1990       2000
DVARIARQGI VPNSTEQGYD LFDAALGHGR PALLALNLDT RALAAQPVAA 2010       2020       2030       2040       2050
LPAPLRALAA DAQAAGARSG GAAARPTAAA AEEPADWAAR LRALAPAEQR 2060       2070       2080       2090       2100
RLLTDLVRRH AATVLGHADP EAVPADAAFK ELGFDSLTAV ELRNRVTAAT 2110       2120       2130       2140       2150
GLRLPATVIF DYPEPGALAE RLRTELAPEE GASATAPDLY APVLSRLTGL 2160       2170       2180       2190       2200
EETLAALASS GVNGGVNGGV ADPGAVTARL ESLLADWKAA HAPSRNGGTA 2210       2220
AERLEAATTD QVLDFIDKEL GVQ
```

The amino acid sequence of *Saccharopolyspora spinosa* SpnB is:

```
                                               (SEQ ID NO: 10)
        10         20         30         40         50
MTVTTSYEEV VEALRASLKE NERLRRGRDR FSAEKDDPIA IVAMSCRYPG 60         70         80         90        100
QVSSPEDLWQ LAAGGVDAIS EVPGDRGWDL DGVFVPDSDR PGTSYACAGG 110        120        130        140        150
FLQGVSEFDA GFFGISPREA LAMDPQQRLL LEVAWEVFER AGLEQRSTRG
```

-continued

```
        160        170        180        190        200
 SRVGVFVGTN GQDYASWLRT PPPAVAGHVL TGGAAAVLSG RVAYSFGFEG 210        220        230        240        250
 PAVTVDTACS SSLVALHLAG QALRAGECDL ALAGGVTVMS TPKVFLEFSR 260        270        280        290        300
 QRGLAPDGRC KSFAAGADGT GWGEGAGLLL LERLSDARRN GHEVLAVVRG 310        320        330        340        350
 SAVNQDGASN GLTAPNGSSQ QRVITQALAS AGLSVSDVDA VEAHGTGTRL 360        370        380        390        400
 GDPIEAQALI ATYGRDRDPG RPLWLGSVKS NIGHTQAAAG VAGVIKMVMA 410        420        430        440        450
 MRHGQLPRTL HVESPSPEVD WSAGTVQLLT ENTPWPRSGR VRRVGVSSFG 460        470        480        490        500
 ISGTNAHVIL EQPPGVPSQS AGPGSGSVVD VPVVPWMVSG KTPEALSAQA 510        520        530        540        550
 TALMTYLDER PDVSSLDVGY SLALTRSALD ERAVVLGSDR ETLLCGVKAL 560        570        580        590        600
 SAGHEASGLV TGSVGAGGRI GFVFSGQGGQ WLGMGRGLYR AFPVFAAAFD 610        620        630        640        650
 EACAELDAHL GQEIGVREVV SGSDAQLLDR TLWAQSGLFA LQVGLLKLLD 660        670        680        690        700
 SWGVRPSVVL GHSVGELAAA FAAGVVSLSG AARLVAGRAR LMQALPSGGG 710        720        730        740        750
 MLAVPAGEEL LWSLLADQGD RVGIAAVNAA GSVVLSGDRD VLDDLAGRLD 760        770        780        790        800
 GQGIRSRWLR VSHAFHSYRM DPMLAEFAEL ARTVDYRRCE VPIVSTLTGD 810        820        830        840        850
 LDDAGRMSGP DYWVRQVREP VRFADGVQAL VEHDVATVVE LGPDGALSAL 860        870        880        890        900
 IQECVAASDH AGRLSAVPAM RRNQDEAQKV MTALAHVHVR GGAVDWRSFF 910        920        930        940        950
 AGTGAKQIEL PTYAFQRQRY WLVPSDSGDV TGAGLAGAEH PLLGAVVPVA 960        970        980        990       1000
 GGDEVLLTGR ISVRTHPWLA EHRVLGEVIV AGTALLEIAL HAGERLGCER 1010       1020       1030       1040       1050
 VEELTLEAPL VLPERGAIQV QLRVGAPENS GRRPMALYSR PEGAAEHDWT 1060       1070       1080       1090       1100
 RHATGRLAPG RGEAAGDLAD WPAPGALPVD LDEFYRDLAE LGLEYGPIFQ 1110       1120       1130       1140       1150
 GLKAAWRQGD EVYAEAALPG TEDSGFGVHP ALLDAALHAT AVRDMDDARL 1160       1170       1180       1190       1200
 PFQWEGVSLH AKAAPALRVR VVPAGDDAKS LLVCDGTGRP VISVDRLVLR 1210       1220       1230       1240       1250
 SAAARRTGAR RQAHQARLYR LSWPTVQLPT SAQPPSCVLL GTSEVSADIQ 1260       1270       1280       1290       1300
 VYPDLRSLTA ALDAGAEPPG VVIAPTPPGG GRTADVRETT RHALDLVQGW 1310       1320       1330       1340       1350
 LSDQRLNESR LLLVTQGAVA VEPGEPVTDL AQAALWGLLR STQTEHPDRF 1360       1370       1380       1390       1400
 VLVDVPEPAQ LLPALPGVLA CGEPQLALRR GGAHAPRLAG LGSDDVLPVP 1410       1420       1430       1440       1450
 DGTGWRLEAT RPGSLDGLAL VDEPTATAPL GDGEVRIAMR AAGVNFRDAL 1460       1470       1480       1490       1500
 IALGMYPGVA SLGSEGAGVV VETGPGVTGL APGDRVMGMI PKAFGPLAVA
```

-continued

```
     1510       1520       1530       1540       1550
DHRMVTRIPA GWSFARAASV PIVFLTAYYA LVDLAGLRPG ESLLVHSAAG 1560       1570       1580       1590       1600
GVGMAAIQLA RHLGAEVYAT ASEDKWQAVE LSREHLASSR TCDFEQQFLG 1610       1620       1630       1640       1650
ATGGRGVDVV LNSLAGEFAD ASLRMLPRGG RFLELGKTDV RDPVEVADAH 1660       1670       1680       1690       1700
PGVSYQAFDT VEAGPQRIGE MLHELVELFE GRVLEPLPVT AWDVRQAPEA 1710       1720       1730       1740       1750
LRHLSQARHV GKLVLTMPPV WDAAGTVLVT GGTGALGAEV ARHLVIERGV 1760       1770       1780       1790       1800
RNLVLVSRRG PAASGAAELV AQLTAYGAEV SLQACDVADR ETLAKVLASI 1810       1820       1830       1840       1850
PDEHPLTAVV HAAGVLDDGV SESLTVERLD QVLRPKVDGA RNLLELIDPD 1860       1870       1880       1890       1900
VALVLFSSVS GVLGSGGQGN YAAANSFLDA LAQQRQSRGL PTRSLAWGPW 1910       1920       1930       1940       1950
AEHGMASTLR EAEQDRLARS GLLPISTEEG LSQFDAACGG AHTVVAPVRF 1960       1970       1980       1990       2000
SRLSDGNAIK FSVLQGLVGP HRVNKAATAD DAESLRKRLG RLPDAEQHRI 2010       2020       2030       2040       2050
LLDLVRMHVA AVLGFAGSQE ITADGTFKVL GFDSLTVVEL RNRINGATGL 2060       2070       2080       2090       2100
RLPATLVFNY PTPDALAAHL VTALSADRLA GTFEELDRWA ANLPTLARDE 2110       2120       2130       2140       2150
ATRAQITTRL QAILQSLADV SGGTGGGSVP DRLRSATDDE LFQLLDNDLE

LP
```

The present invention provides for a polyketide synthase (PKS) capable of synthesizing a carboxylic acid or diacid. The PKS is not a naturally occurring PKS. In some embodiments, the carboxylic acid or diacid is not a compound synthesized by a naturally occurring PKS. In some embodiments, the PKS is a hybrid PKS comprising modules, domains, and/or portions thereof from two or more PKSs. Such carboxylic acids or diacids include the diketides and triketides, and polyketides of more than three ketide units, such as 4, 5, or 6 or more ketide units. The carboxylic acid or diacid can further include one or more functional groups. Such functional groups include, but are not limited to, ethyl, methyl and hydroxyl side chains, and internal olefins and ketones.

In some embodiments, the diacid is adipic acid (or hexanedioc acid), suberic acid (or octanedioc acid), or sebacic acid (or decanedioc acid). In some embodiments, the diacid is a symmetrical compound, such as a fully reduced symmetrical aliphatic compound.

Adipic acid is a six carbon chain fully reduced symmetrical aliphatic compound with no side chains, hence no chiral centers. Side chains (methyl, allyl, hydroxyl) of the carboxylic acid or diacid may be incorporated or formed, depending on the modules employed.

Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases.

Figure 9:
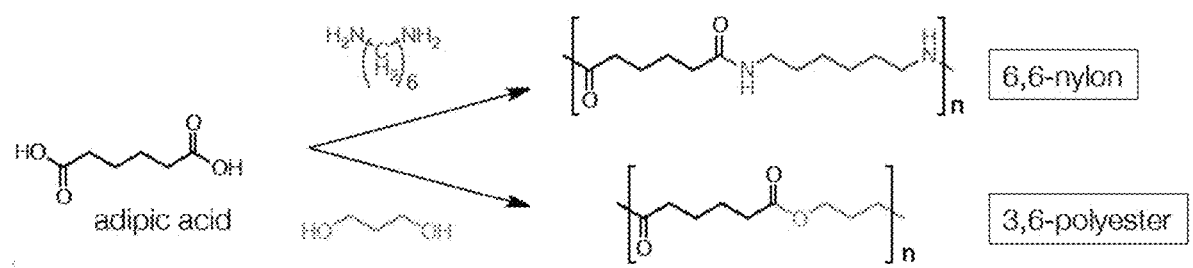
FIG. 9 shows a scheme for making novel polyamides or novel polyesters using diacids (using adipic acid as an example).
Figure 11:
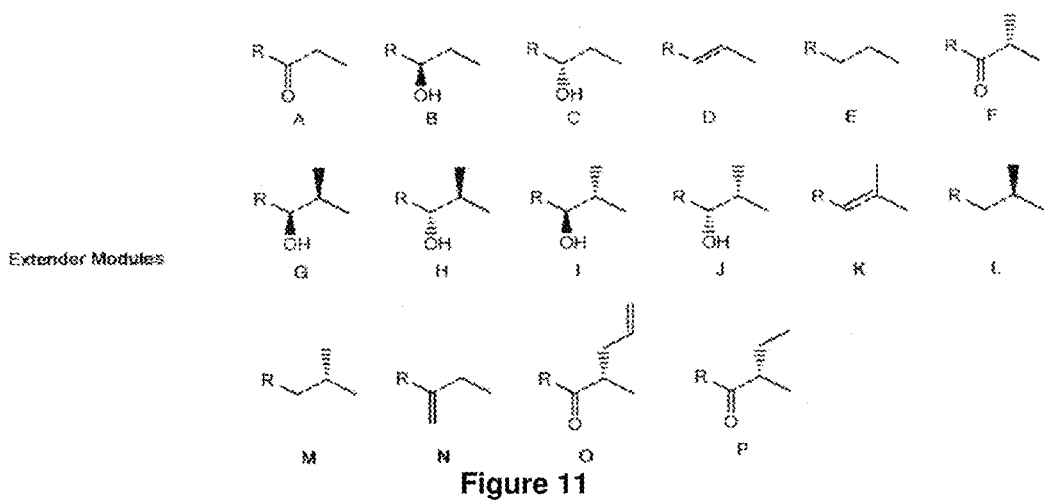
FIG. 11 shows different sides chains that can be added using different extenders.

Polyketide synthases (PKS) employ short chain fatty acyl CoAs in Claisen condensation reactions to produce polyketides. Unlike fatty acid synthases which utilize acetyl CoA as the starter and malonyl CoA as the extender units, and use a single module iteratively to produce the nascent acyl chains, PKSs are composed of discrete modules, each catalyzing the chain growth of a single step. Modules can differ from each other in composition so that overall, a number of different starters (e.g. acetyl CoA, propionyl CoA) and extenders, some of which contain stereospecific methyl (or ethyl) side chains can be incorporated. In addition, PKS modules do not always reduce the 3-carbonyl formed from condensation but may leave it either unreduced (ketone), partially reduced (hydroxyl, 2,3-ene) or fully reduced (3-methylene). In some cases the terminal carboxyl group is usually removed by a decarboxylase domain present at the N-terminus of the corresponding loading domain of the PKS. Because of the correspondence between use of modules in the synthesis and the structure of the polyketide produced, it is possible to program the synthesis to produce a compound of desired structure by selection and genetic manipulation of polyketide synthases. FIG. 9 shows a scheme for making novel polyamides or novel polyesters using diacids (using adipic acid as an example). FIG. 11 shows the various modules and the precursor utilized by each module for incorporation into the corresponding nascent acyl (polyketide) chain to give rise to the range of compounds of interest. Table 4 provides a PKS source for each module. Each PKS source is well-known to one skilled in the art is readily available. In addition, for each module taught in Table 4, there may be other modules from other PKS that can be used.

TABLE 4

PKS sources of the various modules.

| Module | PKS Source |
|---|---|
| A | Rifamycin PKS Module 2 |
| B | Oligomycin PKS Module 1 |
| C | Spiramycin PKS Module 1 |
| D | Pikromycin PKS Module 2 |
| E | Oligomycin PKS Module 3 |
| F | Erythromycin PKS Module 3 |
| G | Oligomycin PKS Module 5 |
| H | Primaricin PKS Module 7 |
| I | Tylosin PKS Module 1 |
| J | Erythromycin PKS Module 1 |
| K | Avermectin PKS Module 7 |
| L | Rapamycin PKS Module 1 |
| M | Erythromycin PKS Module 4 |
| N | Pederin Module 2 |
| O | Ascomycin Module 4 |
| P | FK506 Module 4 |

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to the cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl CoA, methylmalonyl CoA, etc.) incorporated. In addition, PKS modules do not always reduce the β-carbonyl formed from condensation but may leave it either unreduced (ketone), partially reduced (hydroxyl, 2,3-ene) or fully reduced (3-methylene). The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presence of functional reductive domains in the corresponding module. Less commonly, modules are found to contain an additional C-methylation domain (yielding an additional α-methyl side chain, as in epothilone). The makeup of the PKS, therefore, determines the choice of starter and extender acyl units incorporated, the extent of reduction at each condensation step, and the total number of units added to the chain. The wide diversity of structures of polyketides seen in nature is attributed to the diversity in PKS compositions.

A partial list of sources of PKS sequences that can be used in making the PKSs of the present invention, for illustration and not limitation, includes Ambruticin (U.S. Pat. No. 7,332,576); Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, Mol. Microbiol. 14: 163-72); Epothilone (U.S. Pat. No. 6,303,342); Erythromycin (WO 93/13663; U.S. Pat. No. 5,824,513; Donadio et al., 1991, Science 252:675-79; Cortes et al., 1990, Nature 348:176-8); FK506 (Motamedi et al., 1998, Eur. J. Biochem. 256:528-34; Motamedi et al., 1997, Eur. J. Biochem. 244:74-80); FK520 or ascomycin (U.S. Pat. No. 6,503,737; see also Nielsen et al., 1991, Biochem. 30:5789-96); Jerangolid (U.S. Pat. No. 7,285,405); Leptomycin (U.S. Pat. No. 7,288,396); Lovastatin (U.S. Pat. No. 5,744,350); Nemadectin (MacNeil et al., 1993, supra); Niddamycin (Kakavas et al., 1997, J. Bacteriol. 179:7515-22); Oleandomycin (Swan et al., 1994, Mol. Gen. Genet. 242:358-62; U.S. Pat. No. 6,388,099; Olano et al., 1998, Mol. Gen. Genet. 259:299-308); Pederin (PCT publication no. WO 2003/044186); Pikromycin (Xue et al., 2000, Gene 245:203-211); Pimaricin (PCT publication no. WO 2000/077222); Platenolide (EP Pat. App. 791,656); Rapamycin (Schwecke et al., 1995, Proc. Natl. Acad. Sci. USA 92:7839-43); Aparicio et al., 1996, Gene 169:9-16); Rifamycin (August et al., 1998, Chemistry & Biology, 5: 69-79); Soraphen (U.S. Pat. No. 5,716,849; Schupp et al., 1995, J. Bacteriology 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Of the more than thirty PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone (or synthesize) DNA sequences corresponding to desired modules and transfer them as fully functioning units to heterologous, otherwise non-polyketide producing hosts such as E. coli (B. A. Pfeifer, et al., Science 291, 1790 (2001)) and Streptomyces (C. M. Kao, et al., Science 265, 509 (1994)). Additional genes employed for polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in E. coli and other hosts (K. J. Weissman, et al., Chembiochem 5, 116 (2004)). It is also possible to re-program polyketide biosynthesis to produce a compound of desired structure by either genetic manipulation of a single PKS or by construction of a hybrid PKS composed of modules from two or more sources (K. J. Weissman, et al., Chembiochem 5, 116 (2004)).

Recombinant methods for manipulating modular PKS genes to make the PKSs of the present invention are described in U.S. Pat. Nos. 5,672,491; 5,843,718; 5,830,750; 5,712,146; and 6,303,342; and in PCT publication nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, Curr. Opin. Microbiol. 1:319-329, and Baltz, 1998, Trends Microbiol. 6:76-83; hereby incorporated by reference). In some embodiments, the components of the hybrid PKS are arranged onto polypeptides having inter-polypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication no. WO 00/47724, hereby incorporated by reference.

The vast number of polyketide pathways that have been elucidated provide a host of different options to produce these diacids as well as the large number of derivatives. While the products can be vastly different in size and functionality, all employ virtually the same strategy for biosynthesis. The exact interfaces between non-cognate enzyme partners will be determined on a case-by-case basis. ACP-linker-KS and ACP-linker-TE regions from the proteins of interest will be aligned to examine the least disruptive fusion point for the hybrid synthase. Genetic constructions will employ sequence and ligation independent cloning (SLIC) so as to eliminate the incorporation of genetic "scarring".

Nucleic Acids Encoding the PKS

The present invention provides for a recombinant nucleic acid that encodes a polyketide synthase (PKS) of the present invention. The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the carboxylic acid or diacid.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in suitable host cells, such as yeast and prokaryotic host cells, are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *S. coelicolor* CH999 and vectors described in PCT publication no. WO 96/40968 and similar strains of *S. lividans*. See U.S. Pat. Nos. 5,672,491; 5,830,750; 5,843,718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Host Cells Comprising the PKS

The present invention provides for a host cell comprising any of the recombinant nucleic acid and/or PKS of the present invention. In some embodiments, the host cell, when cultured, is capable of producing a carboxylic acid or diacid. The host cell can be a eukaryotic or a prokaryotic cell. In some embodiments, the host cell is a non-human cell. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include *Escherichia coli* or *Streptomyces* species.

The PKS can be in a host cell, or isolated or purified. The PKS can synthesize the carboxylic acid or diacid in vivo (in a host cell) or in vitro (in a cell extract or where all necessary chemical components or starting materials are provided). The present invention provides methods of producing the carboxylic acid or diacid using any of these in vivo or in vitro means.

Methods of Using the PKS

The present invention provides a method of producing a carboxylic acid or diacid, comprising: providing a host cell of the present invention, and culturing said host cell in a suitable culture medium such that the carboxylic acid or diacid is produced. The method can further comprise isolating said carboxylic acid or diacid from the host cell and the culture medium. The method can further comprise reacting the diacid with a diamine to produce a nylon. A suitable diamine is an alkane diamine, such as hexane-1,6-diamine. Alternatively, the method can further comprise reacting the diacid with a dialcohol to produce a polyester. A suitable dialcohol is an alkane diol, such as ethylene glycol, propane diol, or butanediol. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 2002/0192767 and 2002/0045220; hereby incorporated by reference.

The present invention provides for a composition comprising a carboxylic acid or diacid isolated from a host cell from which the carboxylic acid or diacid is produced, and trace residues and/or contaminants of the host cell. Such trace residues and/or contaminants include cellular material produced by the lysis of the host cell.

The diacids, such as adipic acid, provide for the production of "green" nylon, such as that used in Mohawk carpet fibers. Besides nylon production, the ability to manipulate the side chains of the diacids provides for the production of novel polymer precursors that would lead to polymers with a variety of properties. These products may also serve as adhesive, lubricants or precursors for pharmaceuticals or other more complicated compounds.

The present invention has one or more of the following advantages: (1) it reduces the dependence on oil for producing certain chemicals, and (2) it serves as a means of capture and sequestration of carbon from the atmosphere.

REFERENCES CITED

Alini, S., Basile, F., Blasioli, S., Rinaldi, C., and Vaccari, A. (2007). Development of new catalysts for N2O-decomposition from adipic acid plant. Appl. Catal. B Environ. 70, 323-329.

Aparicio, J. F., Caffrey, P., Marsden, A. F., Staunton, J., and Leadlay, P. F. (1994). Limited proteolysis and active-site studies of the first multienzyme component of the erythromycin-producing polyketide synthase. J. Biol. Chem. 269, 8524-8528.

Clomburg, J. M., Blankschien, M. D., Vick, J. E., Chou, A., Kim, S., and Gonzalez, R. (2015). Integrated engineering of β-oxidation reversal and co-oxidation pathways for the synthesis of medium chain ω-functionalized carboxylic acids. Metab. Eng. 28, 202-212.

Donadio, S., Staver, M. J., McAlpine, J. B., Swanson, S. J., and Katz, L. (1991). Modular organization of genes required for complex polyketide biosynthesis. Science 252, 675-679.

Donadio, S., McAlpine, J. B., Sheldon, P. J., Jackson, M., and Katz, L. (1993). An erythromycin analog produced by reprogramming of polyketide synthesis. Proc. Natl. Acad. Sci. 90, 7119-7123.

Dutta, S., Whicher, J. R., Hansen, D. A., Hale, W. A., Chemler, J. A., Congdon, G. R., Narayan, A. R. H., Håkansson, K., Sherman, D. H., Smith, J. L., et al. (2014). Structure of a modular polyketide synthase. Nature 510, 512-517.

Epstein, B. N. (1979). Tough thermoplastic nylon compositions (U.S. Pat. No. 4,174,358).

Gaisser, S., Kellenberger, L., Kaja, A. L., Weston, A. J., Lill, R. E., Wirtz, G., Kendrew, S. G., Low, L., Sheridan, R. M., Wilkinson, B., et al. (2003). Direct production of ivermectin-like drugs after domain exchange in the avermectin polyketide synthase of *Streptomyces avermitilis* ATCC31272. Org. Biomol. Chem. 1, 2840.

George, K. W., Chen, A., Jain, A., Batth, T. S., Baidoo, E. E. K., Wang, G., Adams, P. D., Petzold, C. J., Keasling, J. D., and Lee, T. S. (2014). Correlation analysis of targeted proteins and metabolites to assess and engineer microbial isopentenol production: Targeted Proteomics-Based Correlation Analysis. Biotechnol. Bioeng. 111, 1648-1658.

Hagen, A., Poust, S., de Rond, T., Yuzawa, S., Katz, L., Adams, P. D., Petzold, C. J., and Keasling, J. D. (2014). In Vitro Analysis of Carboxyacyl Substrate Tolerance in the Loading and First Extension Modules of Borrelidin Polyketide Synthase. Biochemistry (Mosc.) 53, 5975-5977.

Hong, H., Appleyard, A. N., Siskos, A. P., Garcia-Bernardo, J., Staunton, J., and Leadlay, P. F. (2005). Chain initiation on type I modular polyketide synthases revealed by limited proteolysis and ion-trap mass spectrometry: Limited proteolysis and MS of modular PKSs. FEBS J. 272, 2373-2387.

Kellenberger, L., Galloway, I. S., Sauter, G., Bihm, G., Hanefeld, U., Cortés, J., Staunton, J., and Leadlay, P. F. (2008). A Polylinker Approach to Reductive Loop Swaps in Modular Polyketide Synthases. ChemBioChem 9, 2740-2749.

Khosla, C. (2009). Structures and Mechanisms of Polyketide Synthases. J. Org. Chem. 74, 6416-6420.

McDaniel, R., Thamchaipenet, A., Gustafsson, C., Fu, H., Betlach, M., Betlach, M., and Ashley, G. (1999). Multiple genetic modifications of the erythromycin polyketide synthase to produce a library of novel "unnatural" natural products. Proc. Natl. Acad. Sci. 96, 1846-1851.

Meluzzi, D., Zheng, W. H., Hensler, M., Nizet, V., and Dorrestein, P. C. (2008). Top-down mass spectrometry on low-resolution instruments: characterization of phosphopantetheinylated carrier domains in polyketide and non-ribosomal biosynthetic pathways. Bioorg. Med. Chem. Lett. 18, 3107-3111.

Tang, Y., Kim, C.-Y., Mathews, I. I., Cane, D. E., and Khosla, C. (2006). The 2.7-Å crystal structure of a 194- kDa homodimeric fragment of the 6-deoxyerythronolide B synthase. Proc. Natl. Acad. Sci. 103, 11124-11129.

Vergnolle, O., Hahn, F., Baerga-Ortiz, A., Leadlay, P. F., and Andexer, J. N. (2011). Stereoselectivity of Isolated Dehydratase Domains of the Borrelidin Polyketide Synthase: Implications for cis Double Bond Formation. ChemBioChem 12, 1011-1014.

Williams, G. J. (2013). Engineering polyketide synthases and nonribosomal peptide synthetases. Curr. Opin. Struct. Biol. 23, 603-612.

Yoon, Y. J., Beck, B. J., Kim, B. S., Kang, H.-Y., Reynolds, K. A., and Sherman, D. H. (2002). Generation of Multiple Bioactive Macrolides by Hybrid Modular Polyketide Synthases in *Streptomyces venezuelae*. Chem. Biol. 9, 203-214.

Yu, J.-L., Xia, X.-X., Zhong, J.-J., and Qian, Z.-G. (2014). Direct biosynthesis of adipic acid from a synthetic pathway in recombinant *Escherichia coli*: Adipic Acid Production From a Synthetic Pathway. Biotechnol. Bioeng. 111, 2580-2586.

Zheng, J., Piasecki, S. K., and Keatinge-Clay, A. T. (2013). Structural Studies of an A2-Type Modular Polyketide Synthase Ketoreductase Reveal Features Controlling α-Substituent Stereochemistry. ACS Chem. Biol. 8, 1964-1971.

The invention having been described, the following examples are offered to illustrate the subject invention by way of illustration, not by way of limitation.

Example 1

Engineering a Polyketide Synthase for Production of Adipic Acid

Polyketides have enormous structural diversity, yet polyketide synthases (PKSs) have thus far been engineered to produce only derivatives of drugs or drug candidates. Thousands of other molecules, including commodity and specialty chemicals could be synthesized using PKSs if composing hybrid PKSs from well-characterized parts derived from natural PKSs was more efficient. Here, using modern proteomics techniques, we demonstrate construction of a chimeric PKS extension module capable of producing one of the most widely used commodity chemicals, adipic acid. To accomplish this, we introduced heterologous reductive domains from various PKS clusters into the borrelidin PKS' first extension module, which we previously showed produces a 3-hydroxy-adipoyl intermediate when co-incubated with the loading module and a succinyl-CoA starter unit. Acyl-ACP intermediate analysis revealed an unexpected bottleneck at the dehydration step which was overcome by introduction of a carboxyacyl-processing dehydratase domain from the second module of the borrelidin. Adipic acid was released from the synthase after appending the erythromycin thioesterase domain to the hybrid PKS.

The results demonstrate the following:
1. Demonstration of commodity chemical production by an engineered polyketide synthase.
2. Acyl-ACP intermediate analysis is used to identify unexpected catalytic bottlenecks.
3. Identification of previously unknown dehydratase domain selectivity.
4. Construction of a broad specificity, fully-reducing PKS module.

Using proteomics-based covalent intermediate analysis, Hagen et al engineered a chimeric polyketide synthase capable of producing adipic acid. In the process they revealed unexpected selectivity in the β-carbon reduction cycle.

Introduction

Here we demonstrate engineering a PKS to produce the commodity chemical adipic acid. Current production of adipic acid results in approximately 10% of anthropogenic emissions of $N_2O$—a potent greenhouse gas (Alini et al., 2007)); therefore, a biological route to adipic acid could be an important alternative.

Within the context of type I PKS-based biosynthesis, we proposed that adipic acid synthesis would most conveniently start from the four-carbon succinyl-CoA, undergo one round of extension with full reduction using a malonyl-CoA extender unit to produce the six carbon adipoyl-ACP intermediate. Adipic acid would then be released from adipoyl-ACP by the action of a thioesterase. Due to its important role in the TCA cycle, succinate/succinyl-CoA is readily available in organisms capable of aerobic respiration (e.g. common production hosts like *E. coli*, *Saccharomyces cerevisiae* and Actinobacteria), as is malonyl-CoA, which is used in fatty acid biosynthesis. Therefore production of adipic acid using a PKS and succinyl-CoA starter would be relatively host and feedstock agnostic, as minimal metabolic engineering would be necessary to ensure adequate precursor supply. Another advantage of using a PKS system is the extensibility inherent in its modular nature. For example, longer diacids could be generated by use of additional (or iterative) modules, and novel adipic acid analogs could be created with α-substitutions (e.g. methyl-, fluoro-, or allyl groups) that may yield polymers with useful attributes such as cross-linkable chemical handles (Epstein, 1979).

Figure 1B:
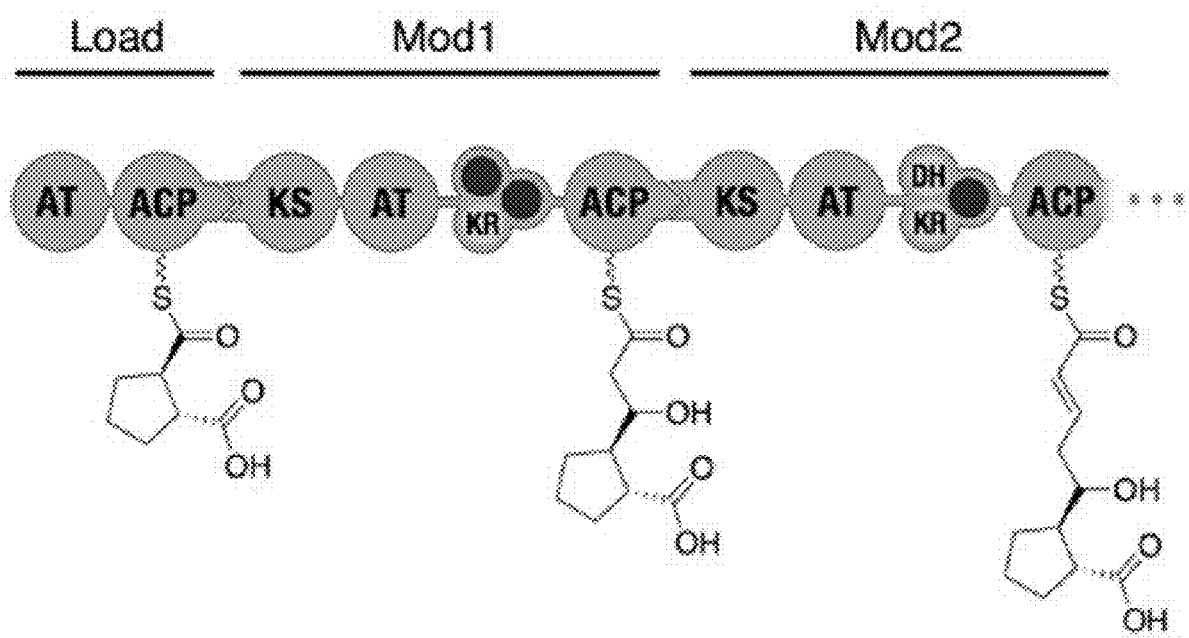
FIG. 1B shows the loading and first extension modules of the borrelidin PKS (hereafter referred to as "BorLM" and "BorMod1", respectively) are capable of producing a 3-hydroxy-adipoyl-ACP intermediate in vitro using succinyl-CoA as a starter substrate and the natural extender substrate, malonyl-CoA. Abbreviations: KS: ketosynthase domain; AT: acyltransferase domain; KR: ketoreductase domain; DH: dehydratase domain; ER: enoylreductase domain; ACP: acyl carrier protein domain.

Previous work in our lab demonstrated that the loading and first extension modules of the borrelidin PKS (hereafter referred to as "BorLM" and "BorMod1", respectively) are capable of producing a 3-hydroxy-adipoyl-ACP intermediate in vitro using succinyl-CoA as a starter substrate and the natural extender substrate, malonyl-CoA (Hagen et al., 2014) (FIG. 1B). To proceed from the 3-hydroxyadipoyl-ACP intermediate to adipic acid, additional β-carbonyl processing and hydrolytic chain release is required. We therefore sought to introduce additional reducing domains into BorMod1, and upon verification of complete reduction, append a thioesterase domain capable of releasing the linear product. "Reductive loop" swaps were among the earliest and most successful demonstrations of modularity in type I PKS systems (Donadio et al., 1993; Gaisser et al., 2003; McDaniel et al., 1999; Yoon et al., 2002). These findings along with limited proteolysis experiments and recent structural studies indicate that reductive loops function as integral units (Aparicio et al., 1994; Dutta et al., 2014; Hong et al., 2005). Despite these examples, no prescriptive rules have been developed to guide successful reductive loop swaps and the most extensive, combinatorial study of reductive loop swaps to date ultimately concluded, "no single donor [module] and no single pair of splice sites were found to be reliably optimal to effect a given alteration" (Kellenberger et al., 2008).

We selected donor reductive loops from the aureothin, indanomycin, nanchangmycin and spinosyn PKS clusters: AurB, IdmO, NanA2, SpnB, respectively, based on three criteria: (1) the loop contained the full complement of reducing domains (ketoreductase, dehydratase and enoyl reductase, hereafter referred to as "KR," "DH," and "ER," respectively), (2) the loop originated from a "standalone" module in which the open reading frame or "subunit" encodes just a single module, and (3) the module harboring the reductive loop naturally incorporates a malonate extender unit. Previous work has suggested a reduction in catalytic efficiency and relaxed stereoselectivity when KR domains are presented with an α-carbon differentially substituted than the KR's normal substrate (McDaniel et al., 1999; Zheng et al., 2013). These loops were introduced combinatorially into BorMod1 using two alternative N-terminal and a single C-terminal splice sites to generate eight chimeras to be tested for adipoyl-ACP production in vitro (FIG. 1A).

In the absence of a thioesterase, intermediates covalently attached to the PKS could be monitored using the "PPant ejection assay" (Meluzzi et al., 2008). This system allows us to identify bottlenecks in the biosynthesis. As PKSs are complex enzymes, determining the point of failure for engineered PKSs is challenging. Most PKS engineering efforts thus far have relied on the presence of the desired final product to determine success, however this approach does not provide information as to where the enzymatic assembly line has stalled if the product is not observed. As part of our efforts to produce the commodity chemical adipic acid, we demonstrate the utility of acyl-carrier protein (ACP) intermediate analysis (via the PPant ejection assay) to "debug" PKSs. Upon satisfactory production of adipoyl-ACP after several rounds of chimeragenesis, a thioesterase was introduced to produce adipic acid.

Results

Figure 2A:
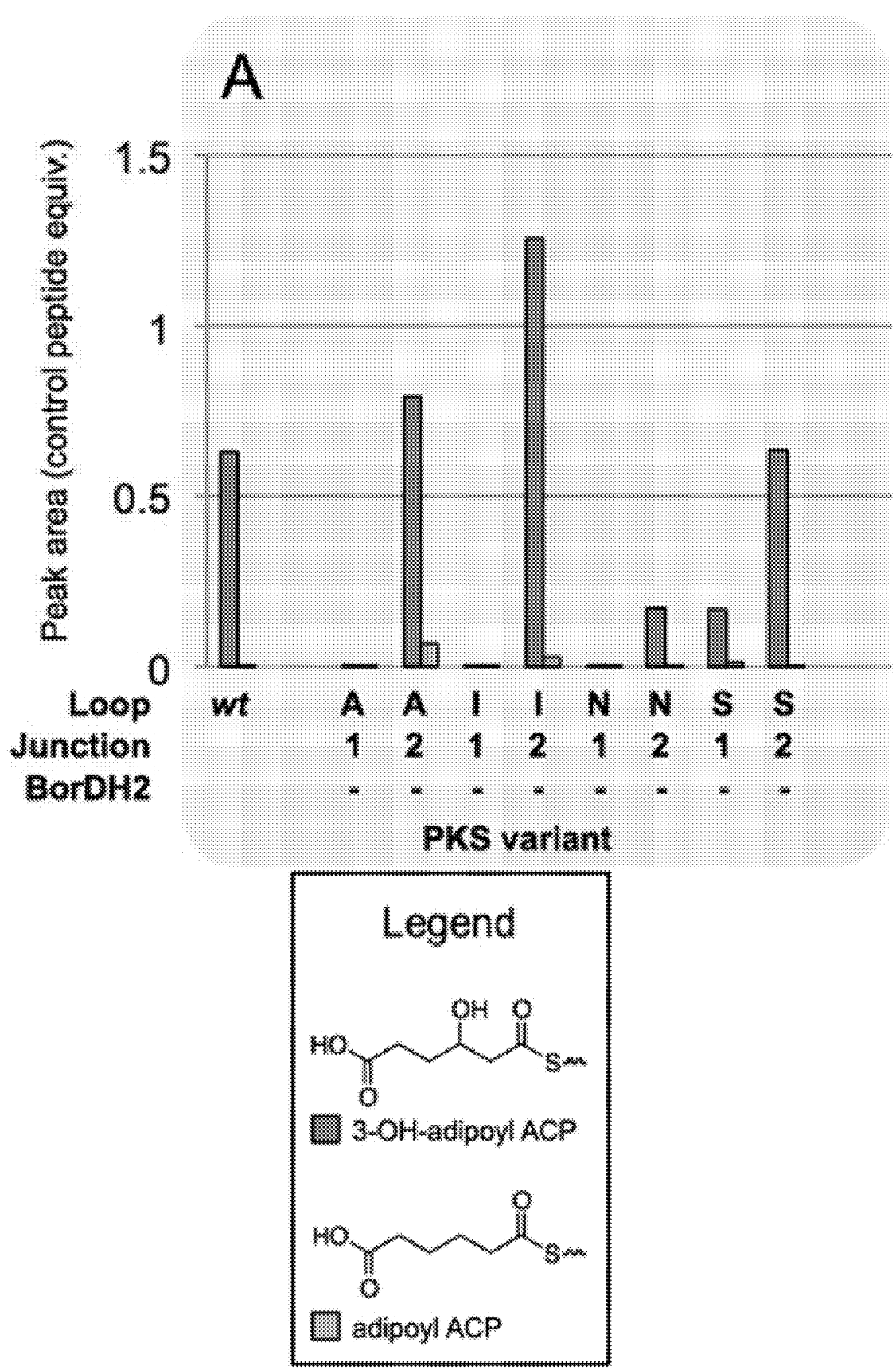
FIG. 2A shows extension intermediate analysis of Bor-Mod1 variants in an initial library. Variants designated by reductive loop source (A=AurB, I=IdmO, N=NanA2, S=SpnB); N-terminal junction (1, 2, 3) and BorDH2 presence (null=wildtype DH domain, t=in trans, c=in cis).

Beta-Carbonyl Processing Stalls at the Dehydration Step; is Alleviated by Provision of BorDH2 in Trans The initial engineered reductive loop BorMod1 library was incubated with the synthetic starter substrate succinyl-SNAC, along with malonyl-CoA and NADPH. Six out of eight constructs were catalytically active, but the primary acyl-ACP species, after introduction of the full reducing loop, remained the partially reduced 3-hydroxy-adipoyl-ACP intermediate; the 3-keto, 2,3-ene and fully reduced (adipoyl-ACP) products were not detected (see FIG. 2A), indicating that reductive processing was stalled at the dehydratase step.

Figure 2B:
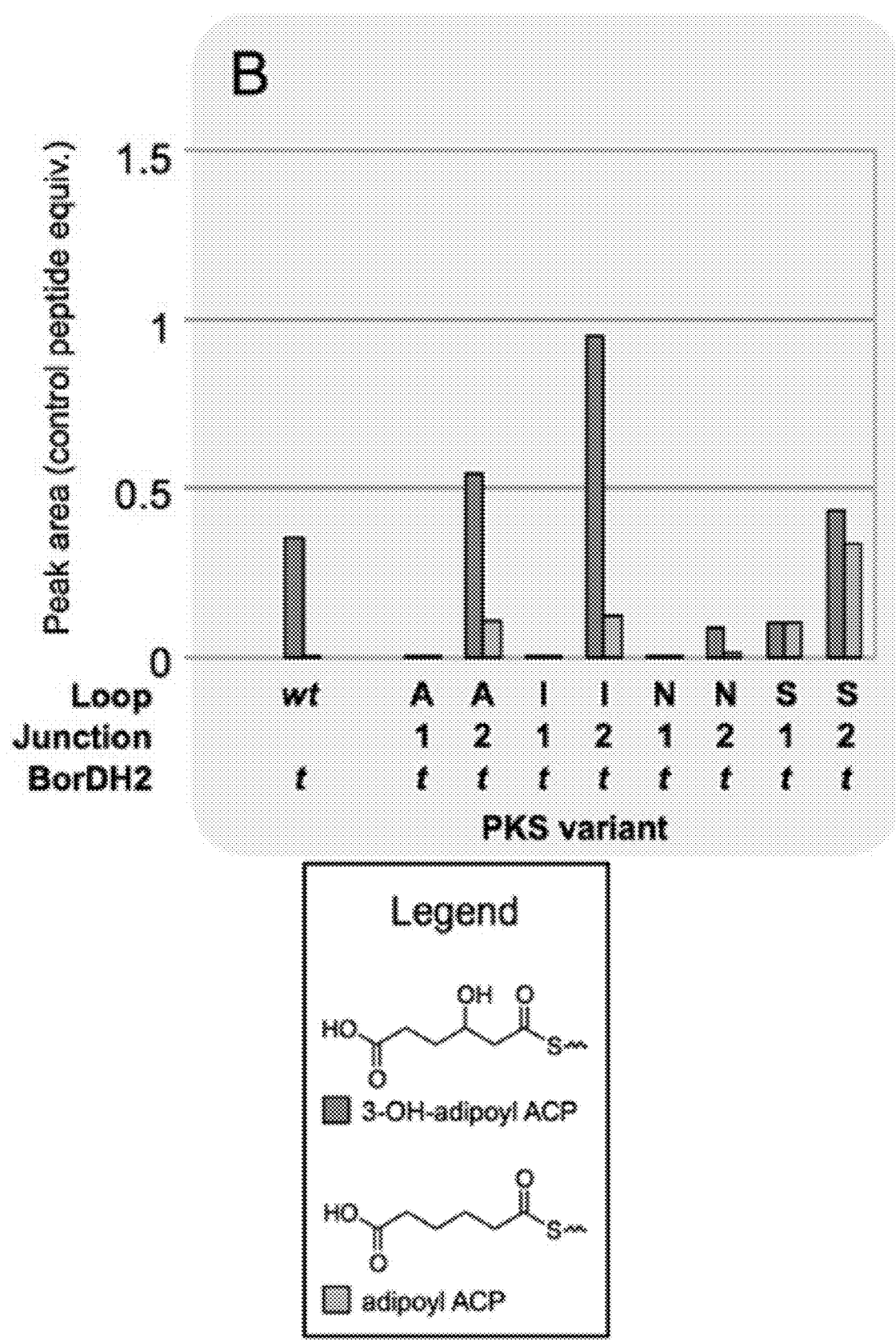
FIG. 2B shows the effect of BorDH2 in trans (indicated using t). Variants designated by reductive loop source (A=AurB, I=IdmO, N=NanA2, S=SpnB); N-terminal junction (1, 2, 3) and BorDH2 presence (null=wildtype DH domain, t=in trans, c=in cis).

We hypothesized the dehydratase domains from the reductive loop variants were not competent to dehydrate 3-hydroxyadipoyl-ACP and therefore sought to test the activity of a different dehydratase domain which processes a substrate carrying a terminal carboxyl group in its natural context. Because of its proximity to a terminal carboxyl group (see FIG. 1B), the first DH domain in the borrelidin cluster, BorDH2, was chosen and provided to the reductive loop library in trans in stoichiometric excess as previous work showed a low rate of DH activity in vitro (Vergnolle et al., 2011). As shown in FIG. 2B, provision of BorDH2 resulted in the production of higher levels of the adipoyl-ACP intermediate when compared to the constructs without BorDH2. A particularly interesting case is the comparison between S2 and S2t, where provision of the dehydratase in trans (S2t), increased adipoyl-ACP production from nearly undetectable levels to the highest level amongst all variants. No significant accumulation of the 2,3-ene-ACP intermediate was observed when BorDH2 was provided (data not shown). This, along with the observed production of adipoyl-ACP in all loop variants, indicates the 2,3-ene intermediate, the immediate product of the dehydration, was readily reduced by the enoyl reductase domains present in cis.

Figures 5, 6:
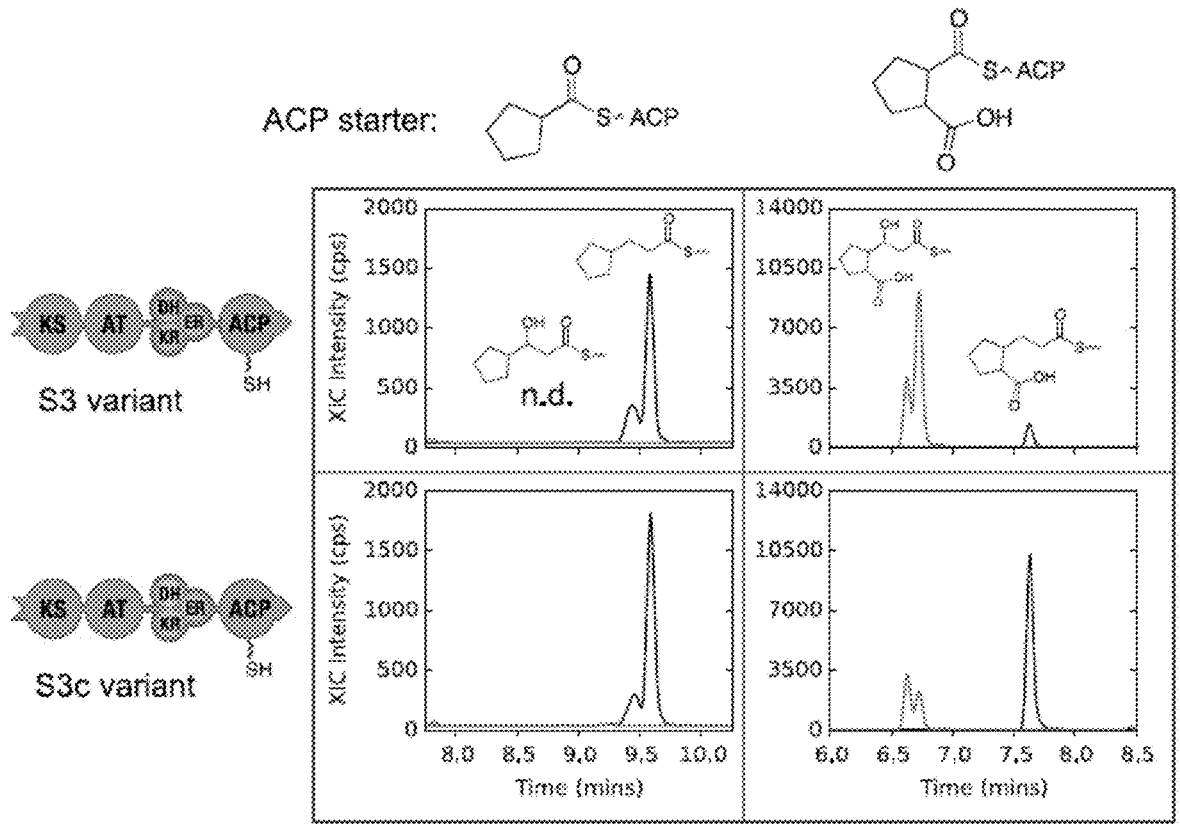
FIG. 5. LC-MS/MS chromatograms of extension reactions using different starter substrates (CPMA-, CPDA-ACP) and BorMod1 variants (S3, S3c). Identity of each peak indicated by molecule appearing above it (3-cyclopentyl-3-hydroxypropanoyl intermediate was not detected; small peak at RT approximately 9.5 mins is a contaminant found in all samples). Abbreviations: KS: ketosynthase domain; AT: acyltransferase domain; KR: ketoreductase domain; DH: dehydratase domain; ER: enoylreductase domain; ACP: acyl carrier protein domain; n.d.: not detected; mins: minutes.
FIG. 6. N- and C-terminal junctions for initial constructs. Arrows indicates crossover point. The amino acid sequence of *Streptomyces parvulus* BorA2 is SEQ ID NO:6. The amino acid sequence of *Streptomyces thioluteus* AurB is SEQ ID NO:7. The amino acid sequence of *Streptomyces antibioticus* IdmO is SEQ ID NO: 8. The amino acid sequence of *Streptomyces nanchangensis* NanA2 is SEQ ID NO:9. The amino acid sequence of *Saccharopolyspora spinosa* SpnB is SEQ ID NO:10.
Figures 7, 8:
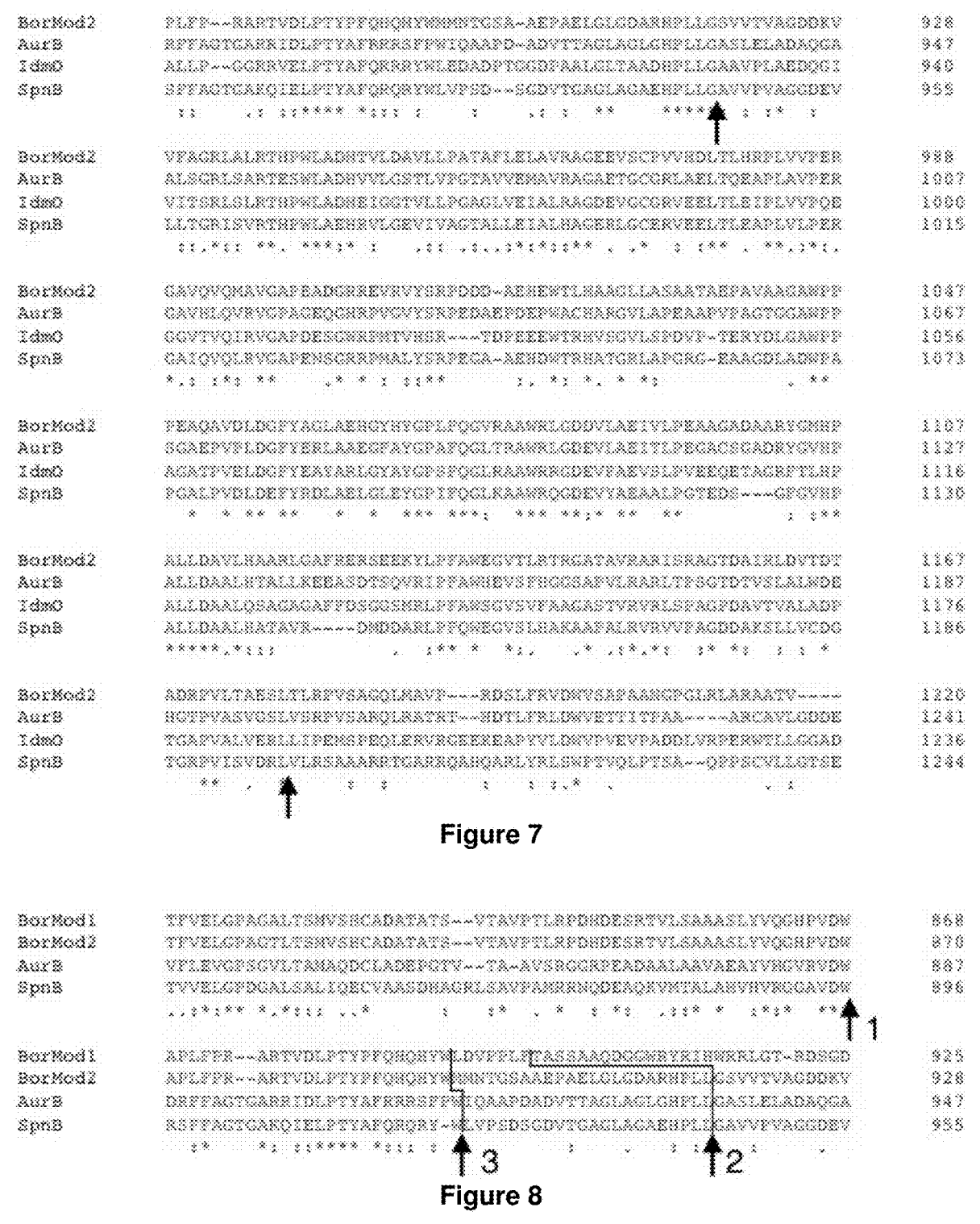

FIG. 6 shows the N- and C-terminal junctions for initial constructs. Arrows indicates crossover point. FIG. 7 shows the junctions for DH swap constructs. Arrows indicates crossover point. FIG. 8 shows the N-terminal junctions including junction 3.

BorDH2 in Cis Further Increases the Proportion of Adipoyl-ACP

Having demonstrated that BorDH2 provided in trans is capable of promoting adipoyl-ACP formation, we next asked whether this was a property unique to this particular dehydratase domain or simply because BorDH2 was provided in stoichiometric excess. To determine this, BorDH2 was swapped into a subset of the most active reductive loop library members in order to replace the native DH domain. After purification, these DH swapped variants were compared to previous constructs as before via intermediate analysis after extension of succinyl-SNAC.

Figure 2C:
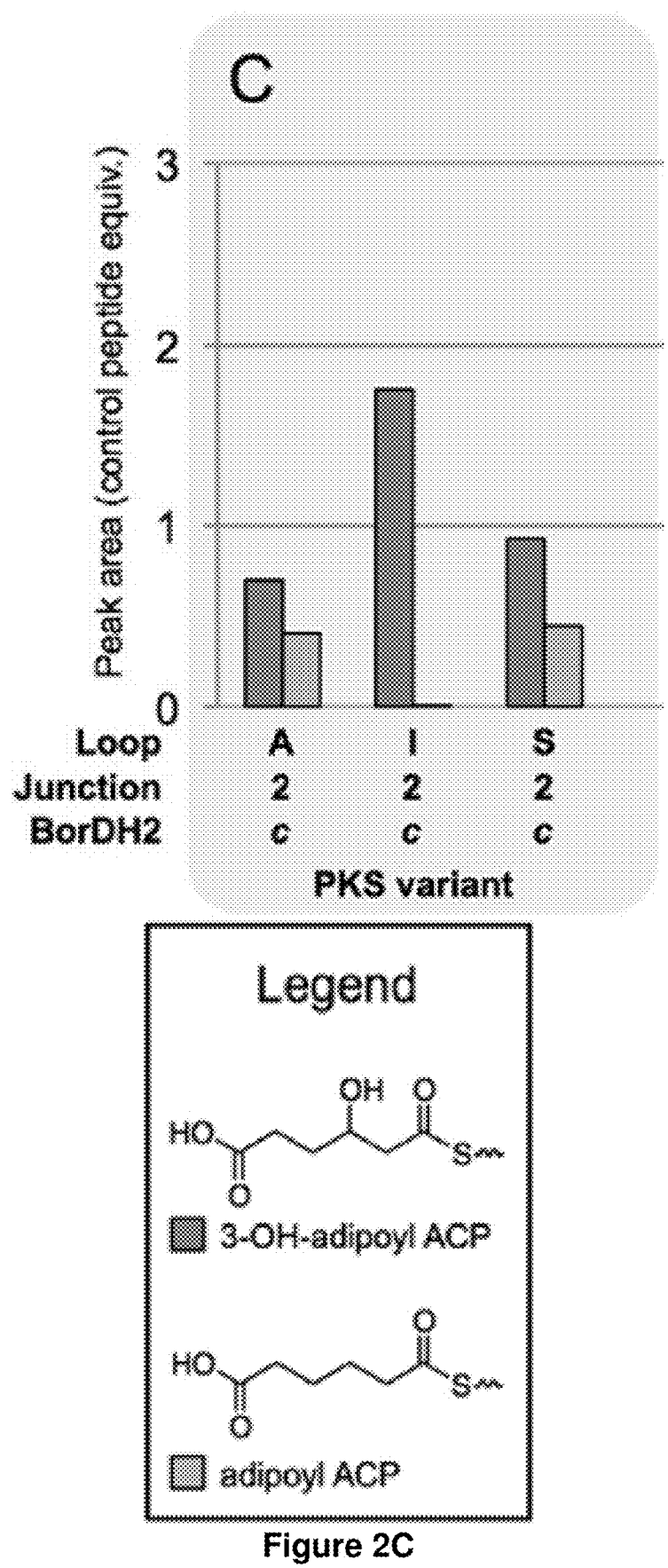
FIG. 2C shows the effect of BorDH2 in cis (indicated using c). Variants designated by reductive loop source (A=AurB, I=IdmO, N=NanA2, S=SpnB); N-terminal junction (1, 2, 3) and BorDH2 presence (null=wildtype DH domain, t=in trans, c=in cis).

As shown in FIG. 2C, DH swapped variants clearly promoted the formation of adipoyl-ACP (e.g. compare A2 (FIG. 2A) to A2c (FIG. 2C)) at levels comparable to where the DH was provided in trans at 50-fold stoichiometric excess (e.g. compare A2t (FIG. 2B) to A2c (FIG. 2C)). These data demonstrate that it is the unique identity of the BorDH2 domain which allows β-carbonyl processing and which is not required at stoichiometric excess for maximum activity.

Refined Chimeric Junction Further Promotes Proportion of Adipoyl-ACP

Despite junction 2 PKS variants generally showing higher production of adipoyl-ACP than junction 1 variants (especially when BorDH2 was included in cis), further sequence and structural analysis indicated that junction 2 constructs may be truncated by approximately 15 residues (depending on how domain boundaries are annotated) at the N-terminus of the dehydratase domain (see supplemental information). These residues are distal to the active site and ACP docking interface and are clearly not essential, however their influence on the overall tertiary structure and kinetics of PKS enzymes was unclear. Therefore, a new N-terminal junction was selected intermediary to junctions 1 and 2 (junction 3). Variants were created for a subset of the reductive loop library which included the best performing AurB and SpnB loop sources both with and without the BorDH2 swap. This location immediately follows the post-AT linker region which is believed to be important for proper KS-AT domain orientation (Tang et al., 2006) and also restores the missing segment in the DH domain N-terminal truncations.

Figure 2D:
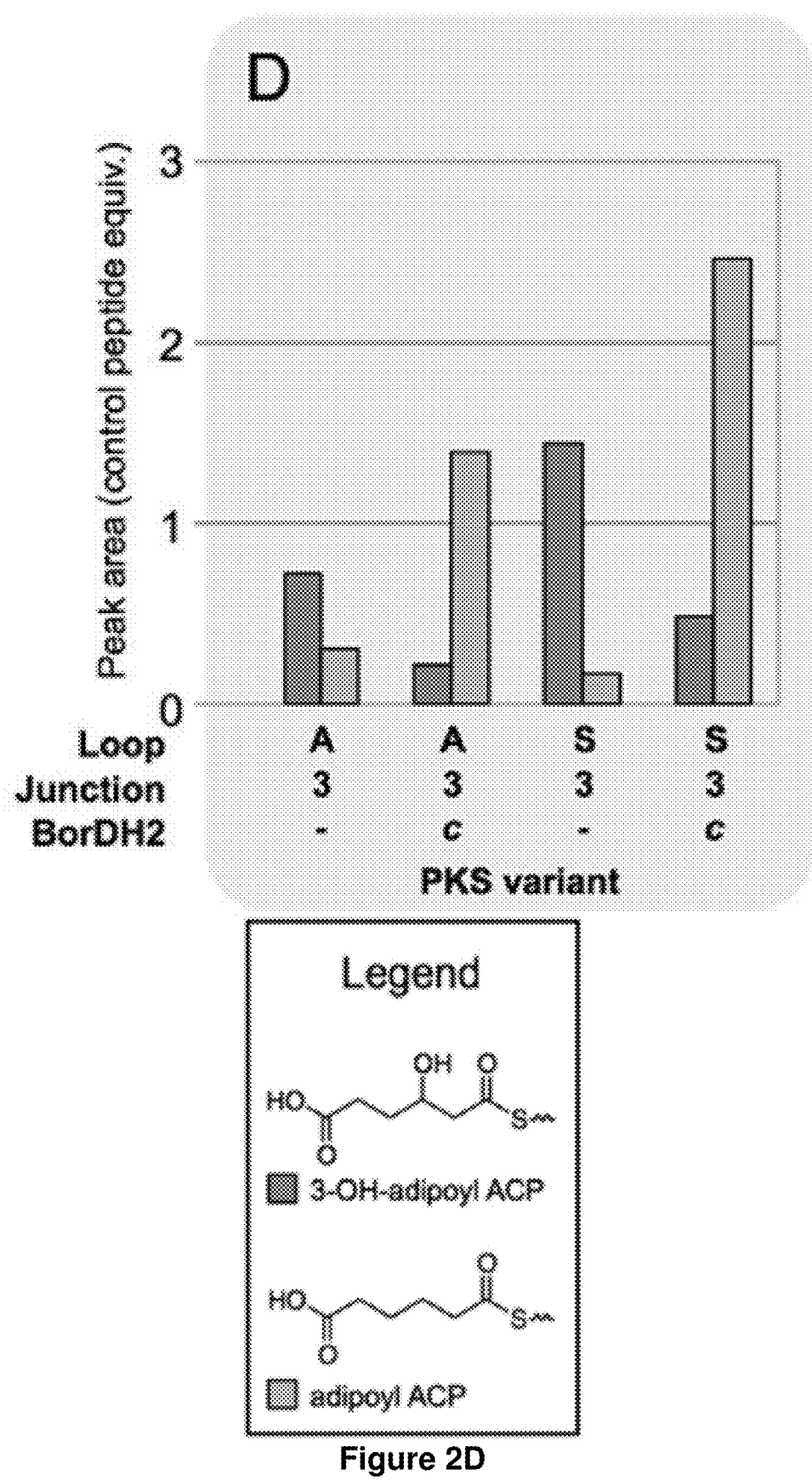
FIG. 2D shows the effect of junction 3 without and with BorDH2 in cis. Variants designated by reductive loop source (A=AurB, I=IdmO, N=NanA2, S=SpnB); N-terminal junction (1, 2, 3) and BorDH2 presence (null=wildtype DH domain, t=in trans, c=in cis).

As shown in FIG. 2D, junction 3 was found to be superior to junction 1 and junction 2 as gauged by total production of the adipoyl-ACP intermediate. Strikingly, the combination of the new junction with the BorDH2 swap displayed a synergistic effect as evidenced by the nearly complete intermediate conversion to adipoyl-ACP in the case of A3c and S3c constructs.

BorDH2 is Necessary Solely for Carboxy-Acyl Processing

Figure 3:
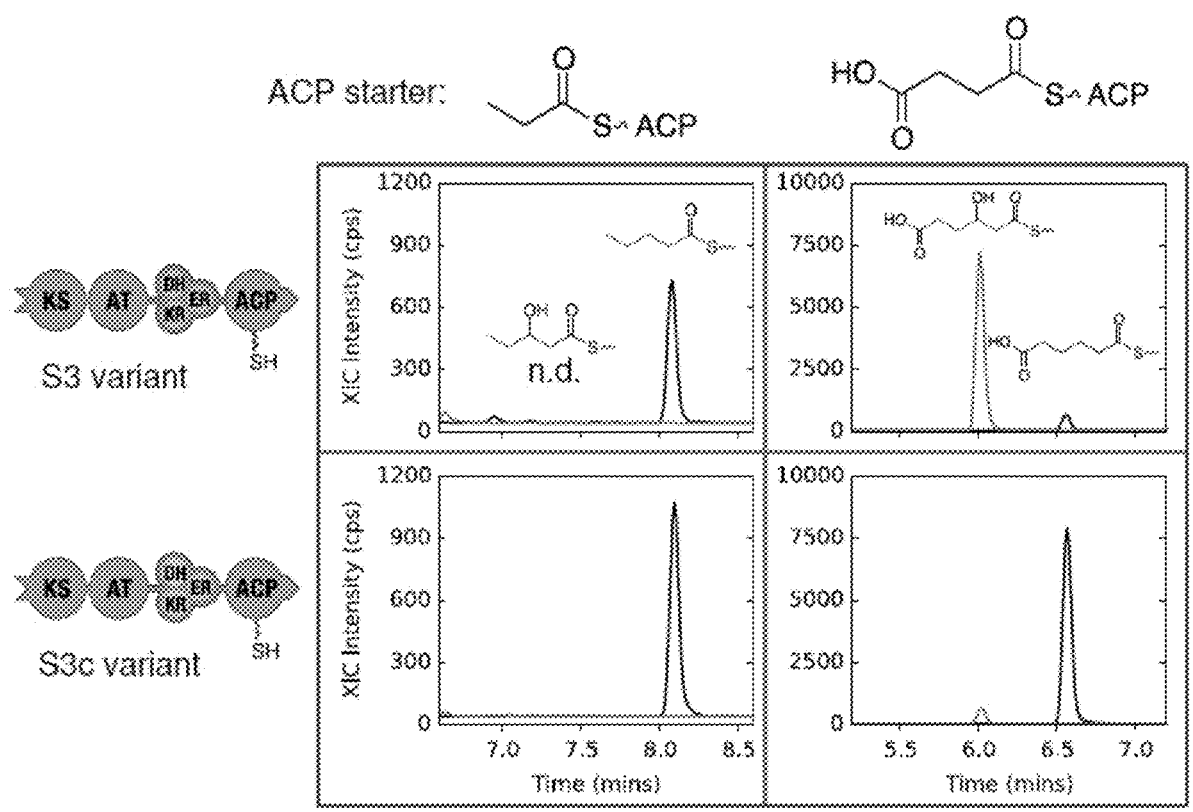
FIG. 3 shows the descarboxy substrates propionyl- and CPMA-ACP were extended and fully reduced to their respective products by both S3 and S3c protein variants. Abbreviations: KS: ketosynthase domain; AT: acyltransferase domain; KR: ketoreductase domain; DH: dehydratase domain; ER: enoylreductase domain; ACP: acyl carrier protein domain; n.d.: not detected; mins: minutes.

The aforementioned data suggest that dehydration of a carboxyacyl-ACP intermediate is a trait unique to BorDH2 and not shared by the four DH domains in the un-engineered reductive loops. The possibility, however, remains that the ACP in BorMod1 does not interact well with non-native DH domains, precluding the presentation of the 3-hydroxyadipoyl-ACP intermediate, whereas the ACP more readily associates with a DH domain from the same PKS cluster. To interrogate this possibility, we incubated the isolated ACP monodomain from BorLM (which naturally presents loaded substrates to BorMod1, FIG. 1B) acylated with a variety of carboxy and descarboxy-CoA substrates with BorDH2-swapped and unswapped version of the S3 variant to determine which substrates could be processed. The CoAs employed were succinyl-CoA and its descarboxy analog propionyl-CoA as well as the natural substrate 1,2-cyclopentanedicarboxyl-CoA (CPDA-CoA) and its respective descarboxy analog cyclopentanemonocarboxyl-CoA (CPMA-CoA). As shown in FIGS. 3 and 5, the descarboxy substrates propionyl- and CPMA-ACP were extended and fully reduced to their respective products by both S3 and S3c protein variants. In contrast, only the BorDH2 swapped variant converted a significant fraction of the 3-hydroxy intermediates to the fully reduced species when carboxylated substrates were provided. These results demonstrate unambiguously that the un-engineered reductive loop of SpnB is competent to perform full β-carbonyl processing of the more typical non-carboxylated intermediates, however BorDH2 is required for full β-carbonyl processing when the substrate contains a distal carboxy group.

Appending a Thioesterase Domain Allows for Production of Free Adipic Acid

Figure 4:
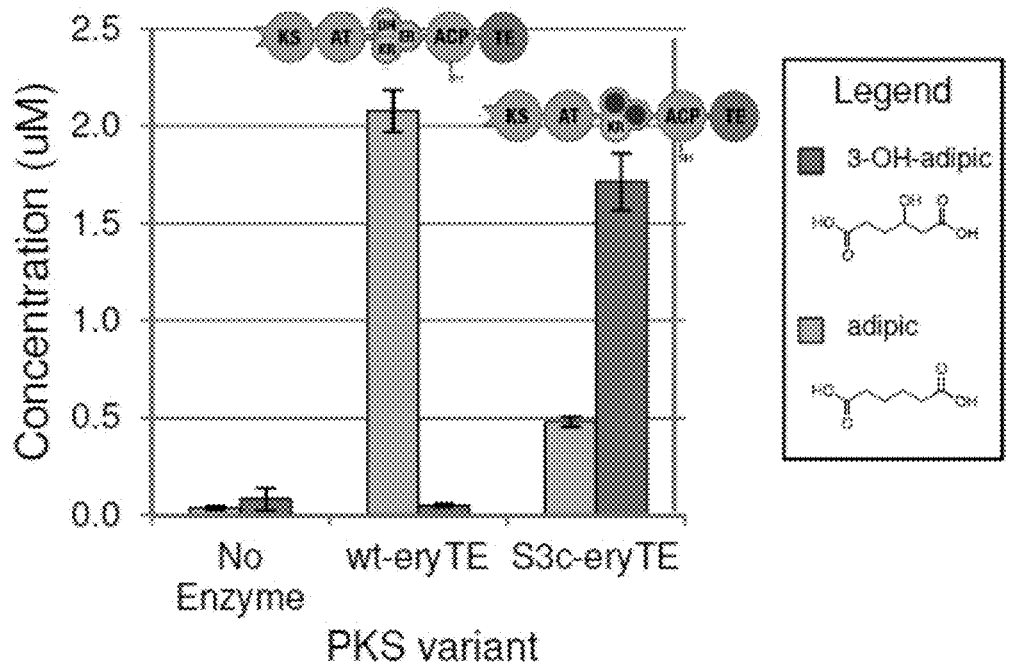
FIG. 4 shows the BorMod1-TE construct produced exclusively 3-hydroxy-adipic acid whereas S3c-TE produced a mixture of the partially and fully reduced adipic acid products. Abbreviations: KS: ketosynthase domain; AT: acyltransferase domain; KR: ketoreductase domain; DH: dehydratase domain; ER: enoylreductase domain; ACP: acyl carrier protein domain; TE: thioesterase.
Figure 4:
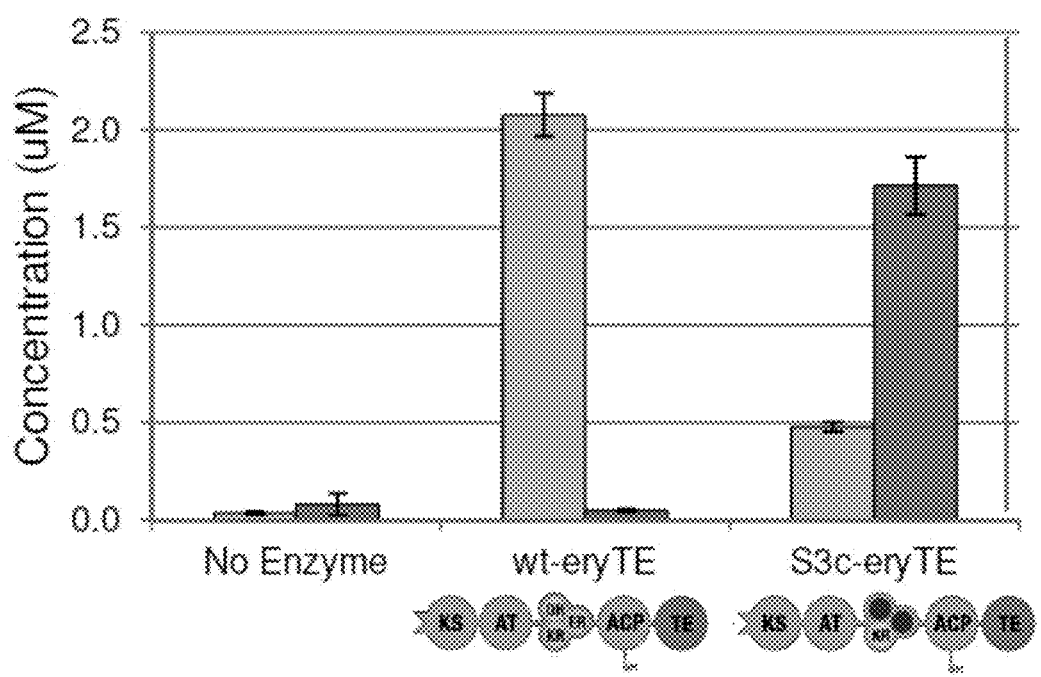

Having demonstrated the construction of a highly engineered extension module capable of producing adipoyl-ACP, we next sought to produce free adipic acid by the addition of a thioesterase (TE). The well-characterized TE domain from the erythromycin cluster was therefore appended to the best performing S3c variant in place of the C-terminal docking domain to create S3c-TE. In order to compare the activity and product profile of the engineered extension module with that of the wild type module, the TE was also appended to wild type BorMod1 to create BorMod1-TE. The proteins were purified and extension assays performed as before and titers were measured via LC-MS/MS by comparison to authentic standards (see materials and methods for synthesis of 3-hydroxy-adipic acid). FIG. 4 shows that as expected, the BorMod1-TE construct produced exclusively 3-hydroxy-adipic acid whereas S3c-TE produced a mixture of the partially and fully reduced adipic acid products. While titers are modest, it is noteworthy that the titers for the wildtype and engineered extension modules are similar. This would suggest that despite the introduction of five chimeric junctions and utilization of domains from three different PKS clusters, the overall kinetics of the engineered extension module are comparable to wildtype.

Discussion

In this study, using proteomics-based intermediate analysis to inform design iterations, we have demonstrated, for the first time, production of a commodity chemical by an engineered polyketide synthase. This was facilitated by prior identification of an extension module, BorMod1, which naturally accepts carboxyacyl substrates and extends with malonyl-CoA. Metabolomic analysis of intermediates in solution has been utilized for bottleneck determination and subsequent improvement of engineered pathways (George et al., 2014). Here, by analysis of the covalent intermediates on the PKS assembly line, we have demonstrated the utility of this methodology to pinpoint and alleviate unexpected catalytic bottlenecks.

Initial activity tests indicated that replacing the reductive loop from BorMod1 with a library of reductive loops from fully reducing modules does not compromise the catalytic competence of the module for the extension reaction. This lends further support to the idea that the reductive loop functions as an "integral unit" apart from the core catalytic activity of the acyltransferase and ketosynthase domains in the module, and that the chimeric junctions used in this study did not perturb the module's tertiary structure such that condensation is precluded.

Interestingly, intermediate analysis showed that dehydration activity on carboxylated 3-hydroxy-ACP intermediates was poor, whereas β-carbonyl processing proceeded uninterrupted using descarboxy substrate analogs, revealing a previously unknown biochemical incompatibility between carboxylated substrates and typical dehydratase domains. In contrast, BorDH2 which in its native context processes a carboxylated substrate, appears substrate agnostic, though more kinetic data would be required to determine whether it prefers one species over the other. It is interesting to note that BorDH2 normally processes a cyclic intermediate with a sterically constrained carboxy group at the 8 position (see FIG. 1B), rather than a linear 6-carboxy intermediate. Future bioinformatic and structural studies could reveal structural determinants of diacid tolerance and could enable engineering of diacid tolerance into typical reductive loops using precise amino acid substitutions of the dehydratase domain rather than chimeric domain swaps.

Addition of a thioesterase to the S3c PKS variant enabled production of free acids. Attenuating the TE activity or tuning its specificity towards the fully reduced product through mutagenesis could possibly shift the product profile further towards adipic acid. Alternatively, increasing the rate of β-carbonyl processing, perhaps through further refined chimeric boundary sampling (including at the C-terminus of the reductive loop) or selection of alternative reductive loops, would increase the proportion and possibly titer of adipic acid. Encouragingly, the overall activities of the wildtype BorMod1-TE and S3c-TE are within error indicating that despite extensive reductive loop engineering, the kinetics of the engineered PKS module was not significantly compromised. Further engineering of hosts for improved expression of heterologous PKSs will be required to improve the productivity of these enzymes.

In recent years a number of biological routes to adipic acid have been developed, typically dependent on reversal of beta-oxidation of dicarboxylic acids (Yu et al., 2014) or omega-oxidation of fatty acids (Clomburg et al., 2015). However, as demonstrated here, the ability to engineer diacid tolerance in a PKS system sets the stage for production of other valuable commodity chemicals (e.g. the eight carbon suberic acid) as well as branched diacids that are not readily accessible through conventional synthetic chemistry or the above biosynthetic routes.

Significance

Polyketide synthases have tremendous synthetic potential, yet have historically been used only for the production of drugs and their derivatives. We show PKSs can also be used for the production of commodity chemicals by engineering a PKS that produces adipic acid. In so doing, we have highlighted the utility of LC-MS/MS based acyl-intermediate analysis techniques which allowed for identification and alleviation of the dehydratase catalytic bottleneck and revealed an unexpected biochemical incompatibility between typical dehydratase domains and carboxylated intermediates. As type I PKSs are inherently modular, this work sets the stage for production of other valuable commodity chemicals such as branched diacids which are not readily accessible through conventional synthetic chemistry.

Experimental Procedures

For details of plasmid construction, protein purifications, chemical syntheses and LC-MS/MS methods, refer to supplemental information.

Intermediate Analysis of PKS Variants

For extensions with succinyl-SNAC, a master mix (final concentrations: 1 mM succinyl-SNAC, 0.2 mM malonyl-CoA, 1 mM NADPH, 2.5 mM TCEP in 100 mM phosphate buffer pH 6.8) was aliquoted to separate tubes, to which 5 uM final concentration of each respective PKS variant was added. For relevant experiments, 50 µM BorDH2 was provided in trans. For extensions using acyl-ACP reagents, ACPs were expressed in apo form and charged using Sfp and various acyl-CoAs as described in (Hagen et al., 2014). These were added to enzyme mixes containing either the S3 or S3c PKS variants and other reaction components at the same concentration as described above. Reactions were incubated at room temperature overnight (~16 hr). Samples were digested with 1:20 w/w porcine trypsin (Sigma-Aldrich) for 4-6 hours at 37 C prior to LC-MS/MS analysis.

Product Analysis of Thioesterase-Harboring Constructs

50 µl reactions were set up as described in intermediate analysis except the final concentration of malonyl-CoA was 0.5 mM. After incubation, samples were diluted with one volume of LC-MS grade water and filtered through 3K molecular weight cut off spin filters (Amicon) which were washed prior to use by filtration of 500 µl of LC-MS grade water. Samples were acidified by the addition of 1% formic acid prior to LC-MS/MS analysis. A dilution series of (3-hydroxy) adipic acid authentic standards was created and processed identically in parallel with samples to generate a concentration standard curve for quantification.

Experimental Procedures

Plasmid construction. Reductive loops were codon-optimized for E. coli and introduced into pARH100 (Hagen et al., 2014) via scarless Gibson assembly (see below for junction boundaries). The j5 algorithm and Device Editor graphical user interface were used to design oligonucleotides and DNA assembly strategies (Hillson et al., 2012).

Purification of PKS constructs. Plasmids were introduced into E. coli strain BAP1 (Pfeifer, 2001) and cultures (1L) were grown at 37° C. in terrific broth to an O.D. of approximately 1.0 and then 60 ng/ml anhydrotetracycline and 200 uM isopropyl-β-D-galactopyranoside (IPTG) were added to induce expression of PKS proteins and Sfp, respectively. Cultures continued incubation at 18 C for 20 hours after which cells were pelleted and stored at −20 C until further processing. Pellets were resuspended in lysis buffer (300 mM NaCl, 50 mM sodium phosphate, pH 6.8, 10 mM imidazole) supplemented with 0.1 mg/ml lysozyme. Suspensions were lysed by several passages through an EmulsiFlex C3 homogenizer (Avestin) and cellular debris was removed by centrifugation (15000 g, 30 minutes). Cobalt resin (2-3 ml) was added to the supernatant and mixed at 4 C for one hour before being applied to a fritted column. Resin was washed with lysozyme-free lysis buffer until flow-through resulted in no color change when mixed with Bradford reagent. Proteins were eluted with several resin volumes of elution buffer (300 mM NaCl, 50 mM phosphate, pH 6.8, 200 mM imidazole) and concentrated via spin filtration (Amicon, 100 kDa MWCO). Concentrated eluate was exchanged into storage buffer (50 mM phosphate, pH 6.8, 10% glycerol) using a PD-10 column (GE Life Sciences), and then further concentrated prior to being flash frozen in liquid nitrogen and stored at −80 C.

Purification of BorDH2. BorDH2 monodomain was purified as above with the exception that protein was concentrated with a 10 kDa MWCO filter and stored as a 50% glycerol solution at −20 C after buffer exchange.

Reagents and Chemicals. HisPur cobalt resin was purchased from Thermo Scientific, Bradford reagent was from Bio-Rad and SDS-PAGE gels from Life Technologies.

Chemical synthesis and NMR data. Solvents (hexanes, ethyl acetate, dichloromethane and methanol) were purchased from EDH; trans-β-hydromuconic acid was purchased from Alfa Aesar; all other reagents were purchased from Sigma-Aldrich or as indicated.

Column chromatography was performed on a Teledyne Isco Combiflash Rf, with RediSep Rf Gold normal phase silica columns.

Gas chromatography—electron impact mass spectrometry (GC-EIMS) was performed on a Agilent5973-HP6890 GC-MS using a 30 meter db5-ms column $^1$H NMR and $^{13}$C NMR were obtained on a Bruker AVB 400 MHz spectrometer and a Bruker AV 500 MHz spectrometer at the UC Berkeley College of Chemistry NMR facility, funded in part by NSF grant CHE-0130862. Chemical shifts are reported in ppm relative to residual solvent signal ($\delta^1$H=3.31 and $\delta^{13}$C=49.0 for Methanol-$d_4$, $\delta^1$H=2.05 and $\delta^{13}$C=29.84 for Acetone-$d_6$).

Succinyl-SNAC

A 100 ml round-bottom flask was charged with 1 g of succinic anhydride and dissolved in a minimal volume of dichloromethane (DCM). 1 eq. N-acetylcysteamine (1.07 ml) was added dropwise to the stirring solution. After overnight incubation at ambient temperature with stirring, the mixture was extracted several times with saturated aqueous sodium bicarbonate solution. The pH of this solution was lowered to approximately 6 with dropwise addition of 1 molar hydrochloric acid in order to protonate unreacted N-acetylcysteamine. The mixture was extracted several times with DCM to remove N-acetylcysteamine and then the pH of the aqueous solution was lowered to approximately 3, again with dropwise addition of IM HCl to protonate the title compound. This was extracted several times with ethyl acetate (EtOAc), dried with the addition of sodium sulfate and filtered into a round-bottom flask. The solution was concentrated in vacuo to afford a fluffy white powder (0.663 g, 3.02 mmol, 30.4% yield).

Synthesis of 3-Hydroxyadipic Acid Standard

Solvent-Free Synthesis of 2-(γ-butyrolactone)acetic acid 2-(γ-butyrolactone)acetic acid (systematic name: 2-(5-oxotetrahydrofuran-2-yl)acetic acid), InChI=1S/C6H8O4/c7-5(8)3-4-1-2-6(9) 10-4/h4H, 1-3H2,(H,7,8)

2 g of trans-β-hydromuconic acid (13.88 mmol) and 4 g of silica gel (60 Å-200 mesh) were mixed in a 50 mL round-bottom flask with stir bar. The free-flowing mixture was heated to 200° C. in a sand bath while gently stirring. The reaction was monitored by pipetting a few milligrams of the hot mixture into 1 mL of dichloromethane (DCM), of which 40 µL was treated with 10 µL of N,O-Bis(trimethylsilyl)trifluoroacetamide (BSTFA) and analyzed by gas chromatography-mass spectrometry (GC-MS). 3 hours into the reaction the mixture starts to turn yellow. After 24 hours, all starting material had been consumed. The mixture was cooled to room temperature and extracted with 50 mL DCM and filtered. The filtrant was extracted with another 50 mL of DCM. The light yellow filtrate was evaporated under reduced pressure and purified by flash chromatography (70:30 Ethyl acetate:Hexane) to afford the title compound as a viscous slightly yellow liquid that solidified upon standing (474 mg, 3.29 mmol, 24% yield)

$^1$H NMR (500 MHz, MeOD) δ 4.91 (p, J=6.5 Hz, 1H), 2.73 (d, J=6.4 Hz, 2H), 2.66-2.52 (m, 2H), 2.49-2.40 (m, 1H), 2.09-1.92 (m, 1H). $^{13}$C NMR (126 MHz, MeOD) δ 179.68, 173.35, 78.64, 49.00, 40.55, 29.35, 28.31.

EIMS (TMS derivative): 201 (7%, (M-Me)$^+$), 159 (27%), 157 (54%), 117 (11%), 101 (8%), 85 (17%), 76 (7%), 75 (100%), 73 (53%), 59 (9%)

Hydrolysis of 2-(7-butyrolactone)acetic acid to Yield 3-hydroxyadipic acid 3-hydroxyadipic acid (systematic name: 3-hydroxyhexanedioc acid) InChI=1S/C6H10O5/c7-4(3-6(10) 11)1-2-5(8)9/h4,7H,1-3H2(H,8,9)(H,10,11)

30 mg of 2-(7-butyrolactone)acetic (208 µmol) was dissolved in 10.4 mL 0.1 M aqueous potassium hydroxide (5 eq.), distributed among the wells of a 96-well PCR plate and heated to 99° C. for 3 hours in an Applied Biosciences Venti thermocycler with heated lid (105° C.). This was diluted into 100 mM sodium phosphate buffer (pH 6.8) to make standard curves. To acquire NMR data, the solution was consolidated and acidified to pH 3 using 6 M hydrochloric acid. The solution was flash frozen in liquid nitrogen and lyophilized to dryness (~24 h). The remaining powder was extracted with 2×2 mL acetone and filtered through a pipette filter (KCl has negligible solubility in acetone). At this point 1 µL of the solution was diluted down to a final volume of 40 µL and derivatized with 10 µL BSTFA to yield the GC-MS chromatogram below. The remaining solution was evaporated under reduced pressure at room temperature to yield the title compound as a white powder (26.7 mg, 165 µmol, 79% yield). Re-subjecting the product to GC-MS shows increasing amounts of 2-(γ-butyrolactone) acetic acid over time, suggesting that neat 3-hydroxyadipic acid spontaneously re-lactonizes at room temperature (unlike 3-hydroxyadipic acid solutions in phosphate buffer, which are stable and hence used for standard curves as described above). Hence, the NMR spectrum reported below shows 2-(γ-butyrolactone)acetic acid as an impurity.

$^1$H NMR (500 MHz, MeOD) δ 4.02 (tdd, J=8.6, 4.8, 3.9 Hz, 1H), 2.52-2.33 (m, 4H), 1.90-1.78 (m, 1H), 1.77-1.63 (m, 1H). $^{13}$C NMR (126 MHz, MeOD) δ 179.68, 173.35, 78.64, 49.00, 40.55, 29.35, 28.31.

EIMS (tris(TMS) derivative): 363 (32% (M-Me)$^+$), 247 (26%), 233 (11%), 203 (12%), 149 (14%), 147 (55%), 133 (10%), 129 (24%), 75 (27%), 73 (100%)

Synthesis of Acyl-CoAs

Synthesis of cyclopentanecarboxyl-CoA (CPMA-CoA) and cyclopentanedicarboxyl-CoA (CPDA-CoA) was previously reported (Hagen et al., 2014)

Construct Design and Plasmid Construction

AurB, IdmO, and SpnB DNA was generously provided by Ryan Phelan. Codon-optimization and synthesis of AurB was performed by Genscript; codon-optimization and synthesis of IdmO, and SpnB was performed by the Joint Genome Institute (JGI). NanA2 DNA was generously provided by Satoshi Yuzawa; codon-optimization and synthesis was performed by DNA2.0.

Amino acid sequences for various modules were aligned using the MUSCLE or Clustal Omega algorithms (Edgar, 2004; Sievers et al., 2014). All DNA pieces were amplified via PCR with either Q5 or Phusion polymerases (New England BioLabs) according to manufacturer's recommendations. Gel-extracted DNA was assembled via Gibson cloning using Gibson Assembly® master mix (New England BioLabs). In the case of construct A3 (pARH159), Gibson assembly failed and sequence was introduced by oligonucleotides using inverse PCR with pARH137 (A2) as a template. A similar strategy was used to create (A,S)3c constructs (pARH163, 164 respectively) starting from (A,S)2c constructs (pARH147, 149 respectively). A complete list of plasmids follows BorDH2 Monodomain BorDH2 domain boundaries were selected after (Vergnolle et al., 2011) and DNA was codon-optimized and synthesized as a gBlock (Integrated DNA Technologies) and ligated into the pET28a vector (Novagen) to yield an N-terminal hexahistidine tagged construct.

TABLE 1

Plasmids described in Example 1 herein. Strains may be accessed and requested through the website for public-registry.jbei.org.

| Strain ID | Alias | Summary |
|---|---|---|
| JBx_045172 | pARH136 | pBbS2k::6xHisMBP-BorA2eloopswap-A1 |
| JBx_045173 | pARH137 | pBbS2k::6xHisMBP-BorA2eloopswap-A2 |
| JBx_045174 | pARH138 | pBbS2k::6xHisMBP-BorA2eloopswap-I1 |
| JBx_045175 | pARH139 | pBbS2k::6xHisMBP-BorA2eloopswap-I2 |
| JBx_045176 | pARH140 | pBbS2k::6xHisMBP-BorA2eloopswap-N1 |
| JBx_045177 | pARH141 | pBbS2k::6xHisMBP-BorA2eloopswap-N2 |
| JBx_045178 | pARH142 | pBbS2k::6xHisMBP-BorA2eloopswap-S1 |
| JBx_045179 | pARH143 | pBbS2k::6xHisMBP-BorA2eloopswap-S2 |
| JBx_045183 | pARH147 | pBbS2k::6xHisMBP-BorA2eloopswap-A2c |
| JBx_045184 | pARH148 | pBbS2k::6xHisMBP-BorA2eloopswap-I2c |
| JBx_045202 | pARH149 | pBbS2k::6xHisMBP-BorA2eloopswap-S2c |
| JBx_045078 | pARH150 | pET28a::BorDH2 |
| JBx_045189 | pARH159 | pBbS2k::6xHisMBP-BorA2eloopswap-A3 |
| JBx_045190 | pARH162 | pBbS2k::6xHisMBP-BorA2eloopswap-S3 |
| JBx_045191 | pARH163 | pBbS2k::6xHisMBP-BorA2eloopswap-A3c |
| JBx_045192 | pARH164 | pBbS2k::6xHisMBP-BorA2eloopswap-S3c |
| JBx_045199 | pARH176 | pBbS2k::6xHisMBP-BorA2eloopswap-S3c-eryTE |

Intermediate Analysis of Succinyl-SNAC Extensions:

Samples were analyzed on an AB Sciex (Foster City, Calif.) 4000 Q-Trap mass spectrometer operating in MRM (SRM) mode coupled to an Agilent 1100 system. 1-2 µg of total peptide was injected onto a Sigma (St. Louis, Mich.) Ascentis Peptide Express C-18 column (2.1 mm×50 mm) via an autosampler. A 20.5-minute method was used with a flow-rate of 400 ul/min. The method begins with 95% Buffer A (water, 2% acetonitrile, 0.1% formic acid) and 5% buffer B (water, 98% acetonitrile, 0.1% formic acid) for 1.2 minutes followed by a rapid rise to 25% over 1 minute and then a very slow rise to 36% over 10 minutes. After the slow gradient step, buffer B was rapidly increased to 90%, held, and dropped back down to re-equilibrate the column as above. The peptides eluting from the column were ionized by a Turbo V Ion source (curtain gas flow: 20 l/min, temperature: 400 C, ion spray voltage: 4,800 V, ion source gas flow: 50 l/min, entrance potential: 10 V) operating in positive-ion mode.

TABLE 2

Mass spectrum parameters for intermediate analysis experiments.

| ID | Q1 | Q3 | Declustering potential | Collision energy |
|---|---|---|---|---|
| ACP1_ctrl | 680.38 | 846.48 (y8) | 125 | 40 |
| Holo-ACP1 | 905.76 | 261.12 | 50 | 44 |
| Keto-ADA-ACP1 | 953.11 | 403.15 | 50 | 44 |
| hydroxy-ADA-ACP1 | 953.77 | 405.16 | 50 | 44 |
| 2,3-ene-ADA-ACP1 | 947.78 | 387.16 | 50 | 44 |
| ADA-ACP1 | 948.45 | 389.17 | 50 | 44 |

Intermediate Analysis of Various Acyl-ACP$_{LM}$ Extensions

Samples were analyzed on an Agilent 6460QQQ mass spectrometer operating in MRM (SRM) mode as previously reported (Dahl et al., 2013). Briefly, 1-2 ug of total peptide was injected on a Sigma Ascentis Peptide Express C-18 column (2.1 mm×50 mm) via an autosampler and separated at 400 ul/min. Liquid chromatography conditions used were as described above. Peptides eluting from the column were ionized using an Agilent Jet Stream source (sheath gas flow: 11 l/min, sheath gas temperature: 350 c, nozzle voltage: 1,000 v, nebulizing pressure: 30 psi, chamber voltage: 4,500 V) operating in positive-ion mode For all experiments, transitions were monitored using a collision cell exit potential of 10 V.

```
                                         (SEQ ID NO: 3)
ACP1_ctrl peptide: VVESVAFGVPSLR (SEQ ID NO: 4)
ACP1 peptide: AAIGPDSSFHAIGFDSLTAVELR
```

(site of phosphopantetheinylation underlined)

Methods for SNAC extensions were designed and data collected in Analyst 3.1 and data was quantified in Multi-Quant 2.1 (AB Sciex). Methods for acyl-ACP extension were designed in Skyline (MacLean et al., 2010) and data collected in MassHunter (Agilent)

Data Analysis

Raw data for each transition was normalized by dividing a transition's peak area by that of a control peptide present in BorMod1, but which does not participate in catalysis and should therefore be invariant across samples ("ACP1_ctrl") to generate values in "control peptide equivalents."

Adipic Acid Analytical Methods

Adipic acid (commercially available) and 3-hydroxy-adipic acid were directly infused into the mass spectrometer operating in negative mode and a scan was conducted to identify product ions during adjustment of relevant acquisition parameters.

(3-Hydroxy) Adipic Acid Production

Samples were analyzed on an AB Sciex (Foster City, Calif.) 4000 Q-Trap mass spectrometer operating in MRM (SRM) mode coupled to an Agilent 1100 system. 15 ul of each reaction was injected onto a Phenomenex (Torrance, Calif.) Kinetex XB C-18 column (3 mm×100 mm, 1.7 u) via an autosampler. A 24 minute method was used with a flow-rate of 200 ul/min and started with 97.5% Buffer A (water, 0.1% formic acid) and 2.5% Buffer B (acetonitrile, 0.1% formic acid) for 3 minutes followed by a rise to 90% buffer B over 10 minutes where it was held for 2 minutes and then a return to 2.5% Buffer B for 9 minutes to re-equilibrate the column. Analytes eluted from column were ionized using a Turbo V Ion source (curtain gas flow: 20 l/min, temperature: 400 C, ion spray voltage: −4,500 V, ion source gas flow: 60 l/min, entrance potential: −10 V) operating in negative-ion mode.

TABLE 3

Mass spectrum parameters for adipic acid and 3-OH-adipic acid detection

| ID | Q1 | Q3 | Declustering potential | Collision energy |
|---|---|---|---|---|
| 3-hydroxy | 161 | 99 | −45 | −18 |
| Adipic | 145 | 101 | −45 | −18 |

FURTHER REFERENCES CITED

Dahl, R. H., Zhang, F., Alonso-Gutierrez, J., Baidoo, E., Batth, T. S., Redding-Johanson, A. M., Petzold, C. J., Mukhopadhyay, A., Lee, T. S., Adams, P. D., et al. (2013). Engineering dynamic pathway regulation using stress-response promoters. Nat. Biotechnol. 31, 1039-1046.

Edgar, R. C. (2004). MUSCLE: multiple sequence alignment with high accuracy and high throughput. Nucleic Acids Res. 32, 1792-1797.

Hagen, A., Poust, S., de Rond, T., Yuzawa, S., Katz, L., Adams, P. D., Petzold, C. J., and Keasling, J. D. (2014). In Vitro Analysis of Carboxyacyl Substrate Tolerance in the Loading and First Extension Modules of Borrelidin Polyketide Synthase. Biochemistry (Mosc.) 53, 5975-5977.

Hillson, N. J., Rosengarten, R. D., and Keasling, J. D. (2012). j5 DNA Assembly Design Automation Software. ACS Synth. Biol. 1, 14-21.

MacLean, B., Tomazela, D. M., Abbatiello, S. E., Zhang, S., Whiteaker, J. R., Paulovich, A. G., Carr, S. A., and MacCoss, M. J. (2010). Effect of Collision Energy Optimization on the Measurement of Peptides by Selected Reaction Monitoring (SRM) Mass Spectrometry. Anal. Chem. 82, 10116-10124.

Sievers, F., Wilm, A., Dineen, D., Gibson, T. J., Karplus, K., Li, W., Lopez, R., McWilliam, H., Remmert, M., Soding, J., et al. (2014). Fast, scalable generation of high-quality protein multiple sequence alignments using Clustal Omega. Mol. Syst. Biol. 7, 539-539.

Vergnolle, O., Hahn, F., Baerga-Ortiz, A., Leadlay, P. F., and Andexer, J. N. (2011). Stereoselectivity of Isolated Dehydratase Domains of the Borrelidin Polyketide Synthase: Implications for cis Double Bond Formation. ChemBioChem 12, 1011-1014.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A polyketide synthase (PKS) capable of synthesizing a carboxylic acid, said PKS comprising a synthetic module comprising SEQ ID NO:1 or SEQ ID NO:2, or a functional variant thereof comprising (i) an amino acid sequence at least 95% identical to SEQ ID NO:1 or SEQ ID NO:2, and (ii) the amino acid residues from position 1 to position 892 of SEQ ID NO:1, wherein the PKS is capable of synthesizing a carboxylic acid.

2. The PKS of claim 1, wherein the functional variant thereof comprises an amino acid sequence at least 99% identical to SEQ ID NO:1 or SEQ ID NO:2.

3. The PKS of claim 2, wherein the synthetic module comprises SEQ ID NO:1.

4. The PKS of claim 2, wherein the synthetic module comprises SEQ ID NO:2.

5. The PKS of claim 1, wherein the carboxylic acid is adipic acid.

* * * * *